US009950081B2

(12) United States Patent
Williams

(10) Patent No.: US 9,950,081 B2
(45) Date of Patent: Apr. 24, 2018

(54) VECTORS AND METHODS FOR GENETIC IMMUNIZATION

(71) Applicant: Nature Technology Corporation, Lincoln, NE (US)

(72) Inventor: James A. Williams, Lincoln, NE (US)

(73) Assignee: Nature Technology Corporation, Lincoln, NE (US)

( * ) Notice: Subject to any disclaimer, the term of this patent is extended or adjusted under 35 U.S.C. 154(b) by 20 days.

(21) Appl. No.: 14/753,438

(22) Filed: Jun. 29, 2015

(65) Prior Publication Data

US 2016/0008488 A1 Jan. 14, 2016

Related U.S. Application Data

(62) Division of application No. 12/601,970, filed as application No. PCT/US2008/006554 on May 22, 2008, now Pat. No. 9,109,012.

(60) Provisional application No. 60/932,160, filed on May 29, 2007.

(51) Int. Cl.
| | |
|---|---|
| *A61K 39/00* | (2006.01) |
| *A61K 39/12* | (2006.01) |
| *A61K 39/145* | (2006.01) |
| *A61K 48/00* | (2006.01) |
| *C07K 14/005* | (2006.01) |
| *C12N 15/113* | (2010.01) |
| *C12N 15/11* | (2006.01) |
| *C12N 15/117* | (2010.01) |
| *C12N 15/85* | (2006.01) |

(52) U.S. Cl.
CPC .......... *A61K 48/0066* (2013.01); *A61K 39/12* (2013.01); *A61K 39/145* (2013.01); *C07K 14/005* (2013.01); *C12N 15/111* (2013.01); *C12N 15/113* (2013.01); *C12N 15/117* (2013.01); *C12N 15/85* (2013.01); *A61K 48/00* (2013.01); *A61K 2039/53* (2013.01); *A61K 2039/55561* (2013.01); *C12N 2310/11* (2013.01); *C12N 2310/111* (2013.01); *C12N 2310/17* (2013.01); *C12N 2310/532* (2013.01); *C12N 2320/30* (2013.01); *C12N 2320/50* (2013.01); *C12N 2710/10322* (2013.01); *C12N 2760/16122* (2013.01); *C12N 2760/16134* (2013.01); *C12N 2800/106* (2013.01); *C12N 2800/107* (2013.01); *C12N 2830/00* (2013.01)

(58) Field of Classification Search
CPC . C12N 15/111; C12N 15/113; C12N 2310/11; C12N 15/907; C12N 9/22
See application file for complete search history.

(56) References Cited

U.S. PATENT DOCUMENTS

| 5,922,583 A | 7/1999 | Morsey |
| 6,500,432 B1 | 12/2002 | Dalemans et al. |
| 6,852,535 B1 | 2/2005 | Thompson |
| 2004/0024140 A1 | 2/2004 | Fujita et al. ............... 525/418 |
| 2004/0096462 A1 | 5/2004 | Rangarajan et al. |
| 2004/0234543 A1 | 11/2004 | Carrera et al. |
| 2004/0241140 A1 | 12/2004 | Pavlakis et al. |
| 2005/0130184 A1 | 6/2005 | Xu et al. |
| 2006/0057564 A1 | 3/2006 | Wang ........................ 435/6.11 |
| 2006/0063232 A1 | 3/2006 | Grabherr et al. |
| 2006/0275897 A1 | 12/2006 | Nabel et al. ............. 435/320.1 |

FOREIGN PATENT DOCUMENTS

| WO | 0061770 A2 | 10/2000 |
| WO | 0219968 A2 | 3/2002 |
| WO | 2005052167 A2 | 6/2005 |
| WO | 2005094415 A2 | 10/2005 |
| WO | WO2005094415 | * 10/2005 |
| WO | 2006023546 A2 | 3/2006 |
| WO | WO 2006/029985 | 3/2006 |
| WO | WO2006/042548 | 4/2006 |
| WO | 2006078979 A2 | 7/2006 |
| WO | WO2006078979 | * 7/2006 |

OTHER PUBLICATIONS

Lee and Schmidt "Characterization of the in Vivo RNA Product of the Pout Promoter of Is10r." *J Bacteriol*, 164(2):556-562 (1985).
Mairhofer, et al., "A Novel Antibiotic Free Plasmid Selection System: Advances in Safe and Efficient DNA Therapy." *Biotechnol J*, 3(1):83-89 (2008).
Brantl "Regulatory Mechanisms Employed by Cis-Encoded Antisense RNAs." *Curr Opin Microbiol*, 10(2):102-109 (2007).
Luke, et al., "Improved Antibiotic-Free DNA Vaccine Vectors Utilizing a Novel RNA Based Plasmid Selection System." *Vaccine*, 27(46):6454-6459 (2009).
Marques et al. "A Structural Basis for Discriminating Between Self and Nonself Double-Stranded RNAs in Mammalian Cells", Nature Biotechnology May 2006, vol. 24, No. 5, p. 559-565.
Matsumoto et al. "Analysis of Double-Stranded RNA-Induced Apoptosis Pathways Using Interferon-Response Noninducible Small Interfering RNA Expression Vector Library", The Journal of Biological Chemistry Jul. 2005, vol. 280, No. 27, p. 25687-25696.
Melchjorsen et al. "Activation of Innate Defense Against a Paramyxovirus Is Mediated by RIG-I and TLR7 and TLR8 in a Cell-Type-Specific Manner", Journal of Virology Oct. 2005, vol. 79, No. 20, p. 12944-12951.

(Continued)

Primary Examiner — Janet L Andres
Assistant Examiner — Barry A Chestnut
(74) *Attorney, Agent, or Firm* — Medlen & Carroll, LLP

(57) ABSTRACT

Improved DNA vaccine plasmids are disclosed that contain novel immunostimulatory RNA compositions. The improved plasmids eliminate all extraneous sequences, incorporate a novel antibiotic free short RNA based selectable marker, increase eukaryotic expression using a novel chimeric promoter, improve yield and stability during bacterial production, and improve immunostimulation. These vectors are utilized in immunization to elicit improved immune responses or therapy to induce type 1 interferon production.

12 Claims, 23 Drawing Sheets

(56) References Cited

OTHER PUBLICATIONS

Figure 1:
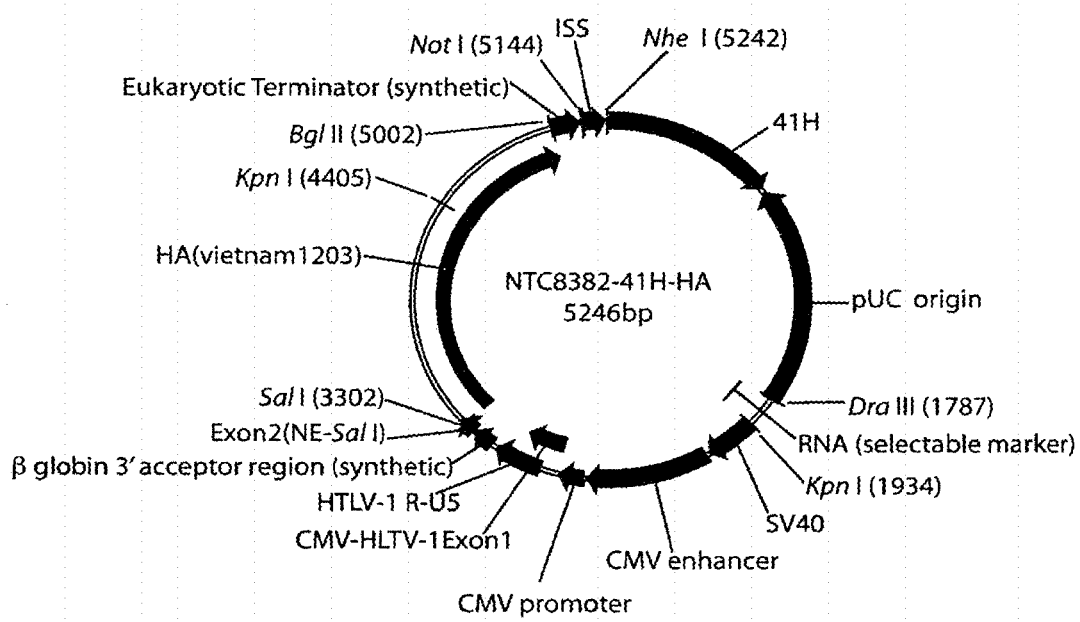

Moller et al. "Spot 42 RNA Mediates Discoordinate Expression of the E. coli Galactose Operon", Genes and Development 2002, vol. 16, p. 1696-1706.
Nociari et al. "Sensing Infection by Adenovirus: Toll-Like Receptor—Independent Viral DNA Recognition Signals Activation of the Interferon Regulatory Factor 3 Master Regulator", Journal of Virology Apr. 2007, vol. 81, No. 8, p. 4145-4157.
Operschall et al. "Mechanism of Protection Against Influenza A Virus by DNA Vaccine Encoding the Hemagglutinin Gene", Intervirology 2000, vol. 43, p. 322-330.
Opitz et al. "IFNβ Induction by Influenza A Virus is Mediated by RIG-I Which is Regulated by the Viral NS1 Protein", Cellular Microbiology 2007, vol. 9, No. 4, p. 930-938.
Parry et al. "Positive and Negative Functional Interactions Between Promoter Elements from Different Classes of RNA Polymerase III-Transcribed Genes", The EMBO Journal 1990, vol. 9, No. 4, p. 1097-1104.
Pepe et al. "Decay of the IS 10 Antisense RNA by 3' Exoribonucleases: Evidence that RNase II Stabilizes RNA-OUT Against PNPase Attack", Molecular Microbiology 1994, vol. 13, No. 6, p. 113-1142.
Pichlmair et al. "RIG-I-Mediated Antiviral Responses to Single-Stranded RNA Bearing 5'—Phosphates", Science Nov. 2006, vol. 314, p. 997-1001.
Plumet et al, "Cytosolic 5'—Triphosphate Ended Viral Leader Transcript of Measles Virus as Activator of the RIG I-Mediated Interferon Response", PLoS ONE Mar. 2007, Issue 3, E279, p. 1-11.
Reyrat et al. "Counterselectable Markers: Untapped Tools for Bacterial Genetics and Pathogenesis", Infection and Immunity Sep. 1998, vol. 66, No. 9, p. 4011-4017.
Rodriguez et al. "Nuclear Export of RNA", Biology of the Cell 2004, vol. 96, p. 639-655.
Saito et al. "Regulation of Innate Antiviral Defenses Through a Shared Repressor Domain in RIG-I and LGP2", PNAS Jan. 2007, vol. 104, No. 2, p. 582-587.
Samanta et al. "EB Virus-Encoded RNAs are Recognized by RIG-I and Activate Signaling to Induce Type I IFN", The EMBO Journal 2006, vol. 25, No. 18. p. 4207-4214.
Sasaki et al. "Apoptosis-Mediated Enhancement of DNA-Raised Immune Responses by Mutant Caspases", Nature Biotechnology Jun. 2001, vol. 19, p. 543-547.
Schroder et al. "TLR3 in Antiviral Immunity: Key Player or Bystander?", TRENDS in Immunology Sep. 2005, vol. 26, No. 9, p. 462-468.
Sewards et al. "Apparent Functional Independence of the Mitochondrial and Nuclear Transcription Systems in Cultured Human Cells", Mol. Gen. Genet. 1994, vol. 245, p. 760-768.
Singh et al. "γ-Monomethyl Phosphate: A Cap Structure in Spliceosomal U6 Small Nuclear RNA", Proc. Natl. Acad. Sci. Nov. 1989, vol. 86, p. 8280-8283.
Singh et al. "Capping of Mammalian U6 Small Nuclear RNA in Vitro is Directed by a Conserved Stem-Loop and AUAUAC Sequence: Conversion of a Noncapped RNA into a Capped RNA", Molecular and Cellular Biology Mar. 1990, vol. 10, No. 3, p. 939-946.
Smulevitch et al. "RTE and CTE mRNA Export Elements Synergistically Increase Expression of Unstable, Rev-Dependent HIV and SIV mRNAs", Retrovirology 2006, vol. 3, 9 pages.
Strat et al. "Specific and nontoxic Silencing in Mammalian Cells with Expressed Long dsRNAs", Nucleic Acids Research 2006, vol. 34, No. 13, p. 3803-3810.
Sugiyama et al. "CpG RNA: Identification of Navol Single-Stranded RNA that Stimulates Human CD14+CD11c+ Monocytes", The Journal of Immunology 2005, vol. 174, p. 2273-2279.
Sumpter et al. "Regulating Intracellular Antiviral Defense and Permissiveness to Hepatitis C Virus RNA Replication Through a Cellular RNA Helicase, RIG-I", Journal of Virology Mar. 2005, vol. 79, No. 5, p. 2689-2699.
Szafranski et al. "A new Approach for Containment of Microorganisms: Dual Control of Streptavidin Expression by Antisense RNA and the T7 Transcription System", Proc. Natl. Acad. Sci. Feb. 1997, vol. 94, p. 1059-1063.
Toka et al. "Molecular Adjuvants for Mucosal Immunity", Immunological Reviews 2004, vol. 199, p. 100-112.
Vyas et al. "Inhibition of the Protein Kinase PKR by the Internal Ribosome Entry site of the Hepatitis C Virus Genomic RNA", RNA RNA 2003, vol. 9, No. 7, p. 858-870.
Wang et al. "Effects of Length and Location on the Cellular Response to Double-Stranded RNA", Microbiology and Molecular Biology Reviews Sep. 2004, vol. 68, No. 3, p. 432-452.
Weber et al. "Induction of Interferon Synthesis by the PKR-Inhibitory VA RNAs of Adenoviruses", Journal of Interferon and Cytokine Research 2006, vol. 26, p. 1-7.
Whitmore et al. "Synergistic Activation of Innate Immunity by Double-Stranded RNA and CpG DNA Promotes Enhanced Antitumor Activity", Cancer Research Aug. 2004, vol. 64, p. 5850-5860.
Winkelman et al. "Proton Suicide: General Method for Direct Selection of Sugar Transport- and Fermentation-Defective Mutants", Journal of Bacteriology Nov. 1984, vol. 160, No. 2, p. 687-690.
Yoon et al. "Efficient Cloning and Engineering of Entire Mitochondrial Genomes in Escherichia coli and Transfer into Transcriptionally Active Mitochondria", Nucleic Acids Research 2003, vol. 31, No. 5, p. 1407-1415.
Zuker et al. "Mfold Web Server for Nucleic Acid Folding and Hybridization Prediction", Nucleic Acids Research 2003, vol. 31, No. 13, p. 3406-3415.
Ma et al. "Secondary and Tertiary Structure in the Central Domain of Adenovirus Type 2 VA RNA", RNA 1996, vol. 2, p. 937-955.
Schramm et al. "Recruitment of RNA Polymerase III to its Target Promoters", Genes and Development 2002, vol. 16, p. 2593-2620.
Lamb et al. "The Gene Structure and Replication of Influenza Virus", Ann. Rev. Biochem. 1983, vol. 52, p. 467-506.
Rahman et al. "Effect of Single-Base Substitutions in the Central Domain of Virus-Associated RNA I on Its Function", Journal of Virology Jul. 1995, vol. 69, No. 7, p. 4299-4307.
Lu et al. "Adenovirus VA1 Noncoding RNA Can Inhibit Small Interfering RNA and MicroRNA Biogenesis", Journal of Virology Dec. 2004, vol. 78, No. 23, p. 12868-12876.
Andersson et al. "Suppression of RNA Interference by Adenovirus Virus-Associated RNA", Journal of Virology Aug. 2005, vol. 79, No. 15, p. 9556-9565.
Applequist et al. "Activation of Innate Immunity, Inflammation, and Potentiation of DNA Vaccination Through Mammalian Expression of the TLR5 Agonist Flagellin" The Journal of Immunology 2005, vol. 175, p. 3882-3891.
Barchet et al. "Dendritic Cells Respond to Influenza Virus Through TLR7- and PKR-Independent Pathways", European Journal of Immunology 2005, vol. 35, p. 236-242.
Barouch et al. "A Human T-Cell Leukemia Virus Type 1 Regulatory Element Enhances the Immunogenicity of Human Immunodeficiency Virus Type 1 DNA Vaccines in Mice and Nonhuman Primates" Journal of Virology Jul. 2005, vol. 79, No. 14, p. 8828-8834.
Berglund et al. "Enhancing Immune Responses Using Suicidal DNA Vaccines", Nature Biotechnology Jun. 1998, vol. 16, p. 562-565.
Bowie et al. "RIG-I: tri-ing to Discriminate Between Self and Non-Self RNA", Trends in Immunology, vol. 28, No. 4, p. 147-150.
Buchan et al. "Electroporation as a "Prime/Boost" Strategy for Naked DNA Vaccination Against a Tumor Antigen", The Journal of Immunology 2005, vol. 174, p. 6292-6298.
Buzan et al. "Preference of Human Mitochondrial RNA Polymerase for Superhelical Templates with Mitochondrial Promoters", Biochemical and Biophysical Research Communications Apr. 1988, vol. 152, No. 1, p. 22-29.
Cardon et al. "Pervasive CpG Suppression in Animal Mitochondrial Genomes", Proc. Natl. Acad. Sci. Apr. 1994, vol. 91, p. 3799-3803.
Chang et al. "Flavivirus Induces Interferon-Beta Gene Expression Through a Pathway Involving RIG-I-Dependent IRF-3 and PI3K-Dependent NF-kB Activation", Microbes and Infection 2006, vol. 8, p. 157-171.

(56) References Cited

OTHER PUBLICATIONS

Chang et al. "Enhanced Expression and HIV-1 Inhibition of Chimeric tRNA Lys3-Ribozymes Under Dual U6 snRNA and tRNA Promoters", Molecular Therapy Oct. 2002, vol. 6, No. 4, p. 481-489.
Chattergoon et al. "Co-Immunization with Plasmid IL-12 Generates a Strong T-cell Memory Response in Mice", Vaccine 2004, vol. 22, p. 1744-1750.
Collombet et al. "Introduction of Plasmid DNA into Isolated Mitochondria by Electroporation", The Journal of Biological Chemistry 1997, vol. 272, No. 8, p. 5342-5347.
Dean et al. "Sequence Requirements for Plasmid Nuclear Import", Experimental Cell Research 1999, vol. 253, p. 713-722.
Desai et al. "Activation of Interferon-Inducible 2'-5' Oligoadenylate Sythetase by Adenoviral VAI RNA", The Journal of Biological Chemistry 1995, vol. 270, No. 7, p. 3454-3461.
Diebold et al. "Innate Antiviral Responses by Means of TLR7-Mediated Recognition of Single-Stranded RNA", Science Mar. 2004, vol. 303, p. 1529-1531.
Fang et al. "Synthetic Influenza Viral Double-Stranded RNA Induces an Acute-Phase Response in Rabbits", Journal of Medical Virology 1999, vol. 57, p. 198-203.
Gantier et al. "The Response of Mammalian Cells to Double-Stranded RNA", Cytokine Growth Factor Rev. 2007, vol. 18, p. 363-371.
Garg et al. "The Hybrid Cytomegalovirus Enhancer / Chicken β-Actin Promoter Along with Woodchuck Hepatitis Virus Post-transcriptional Regulatory Element Enhances the Protective Efficacy of DNA Vaccines", The Journal of Immunology 2002, vol. 173, p. 550-558.
Gaspari et al. "The Mitochondrial RNA Polymerase Contributes Critically to Promoter Specificity in Mammalian Cells", The EMBO Journal 2004, vol. 23, No. 23, p. 4606-4614.
Gitlin et al. "Essential Role of mda-5 in Type I IFN Responses to Polyriboinosinic: Polyribocytidylic Acid and Encephalomyocarditis Picornavirus", PNAS 2006, vol. 103, No. 22, p. 8459-8464.
Groskreutz et al. "Increased Gene Expression in Mammalian Cell Lines Using pAdVAntage (TM) DNA as a Co-Transfectant", Promega Notes Magazine 1994, vol. 48, p. 8-13.
Gurunathan et al. "DNA Vaccines: Immunology, Application, and Optimization", Annu. Rev. Immunol. 2000, vol. 18, p. 927-974.
Haldimann et al. "Conditional-Replication, Integration, Excision, and Retrieval Plasmid—Host Systems for Gene Structure—Function Studies of Bacteria", Journal of Bacteriology Nov. 2001, vol. 183, No. 21, p. 6384-6393.
Hassani et al. "A Hybrid CMV-H1 Construct Improves Efficiency of PEI- Delivered shRNA in the Mouse Brain", Nucleic Acids Research 2007, vol. 35, No. 9, p. 1-9.
Heil et al. "Species-Specific Recognition of Single-Stranded RNA via Toll-Like Receptor 7 and 8", Science Mar. 2004, vol. 303, p. 1526-1529.
Hornung et al. Sequence-Specific Potent Induction of IFN—a by Short Interfering RNA in Plasmacytoid Dendritic Cells Through TLR7, Nature Medicine Mar. 2005, vol. 11, No. 3, p. 263-270.
Hornung et al. "5'-Triphosphate RNA Is the Ligand for RIG-I", Science Nov. 2006, vol. 314, p. 994-997.
Jaenecke et al. "A Stringently Controlled Expression System for Analysing Lateral Gene Transfer Between Bacteria", Molecular Microbiology 1996, vol. 21, p. 293-300.

Jarczak et al. "Hairpin Ribozymes in Combination with siRNAs Against Highly Conserved Hepatitis C Virus Sequence Inhibit RNA Replication and Protein Translation from Hepatitis C Virus Subgenomic Replicons", FEBS Journal 2005, vol. 272, p. 5910-5922.
Kato et al. "Differential Roles of MDA5 and RIG-I Helicases in the Recognition of RNA Viruses", Nature 2006, vol. 441, p. 101-105.
Kawai et al. "IPS-1, an Adaptor Triggering RIG-I- and Mda5-Mediated Type I Interferon Induction", Nature Immunology Oct. 2005, vol. 6, No. 10, p. 981-988.
Kim et al. "Enhancement of Suicidal DNA Vaccine Potency by Delaying Suicidal DNA-Induced Cell Death", Gene Therapy 2004, vol. 11, p. 336-342.
Koulintchenko et al. "Natural Competence of Mammalian Mitochondria Allows the Molecular Investigation of Mitochondrial Gene Expression", Human Molecular Genetics 2006, vol. 15, No. 1, p. 143-154.
Kutzler et al. "Coimmunization with an Optimized IL-15 Plasmid Results in Enhanced Function and Longevity of CD8 T Cells That are Partially Independent of CD4 T Cell Help", The Journal of Immunology 2005, vol. 175, p. 112-123.
Kuwabara et al. "Significantly Higher Activity of a Cytoplasmic Hammerhead Ribozyme than a Corresponding Nuclear Counterpart: Engineered tRNAs with an Extended 3' end can be Exported Efficiently and Specifically to the cytoplasm in Mammalian Cells", Nucleic Acids Research 2001, vol. 29, No. 13, p. 2780-2788.
Lavigueur et al. "A Splicing Enhancer in the Human Fibronectin Alternate ED1 Exon Interacts with SR Proteins and Stimulates U2 snRNP Binding", Genes and Development 1993, vol. 7, p. 2405-2417.
Lee et al. "Immuno-Stimulatory Effects of Bacterial-Derived Plasmids Depend on the Nature of the Antigen in Intramuscular DNA Inoculations", Immunology 1998, vol. 94, p. 285-289.
Lei et al. "Adenovirus VAI RNA Antagonizes the RNA-Editing Activity of the ADAR Adenosine Deaminase", Virology 1998, vol. 245, p. 188-196.
Leitner et al. "Enhancement of Tumor-Specific Immune Response with Plasmid DNA Replicon Vectors", Cancer Research Jan. 2000, vol. 60, p. 51-55.
Leitner et al. "Apoptosis is Essential for the Increased Efficacy of Alphaviral Replicase-Based DNA Vaccines", Vaccine 2004, vol. 22, p. 1537-1544.
Leitner et al. "Alphavirus-Based DNA Vaccine Breaks Immunological Tolerance by Activating Innate Antiviral Pathways", Nature Medicine Jan. 2003, vol. 9, No. 1, p. 33-39.
Leitner et al. "DNA Vaccines and Apoptosis: to Kill or not to Kill?", The Journal of Clinical Investigation Jul. 2003, vol. 112, No. 1, p. 22-24.
Lemieux, "Technological Advances to Increase Immunogenicity of DNA Vaccines", Expert Rev. Vaccines 2002, vol. 1, p. 85-93.
Lopez et al. "Toll-Like Receptor-Independent Triggering of Dendritic Cells Maturation by Viruses", Journal of Virology Apr. 2006, vol. 80, No. 7, p. 3128-3134.
Manoj et al. "Approaches to Enhance the Efficacy of DNA Vaccines", Critical Reviews in Clinical Laboratory Sciences 2004, vol. 41, p. 1-39.

* cited by examiner

Figure 4 eRNA1i: tRNA-INFdsDNA-U6 (recessed 5' PPP, U6 A start)

tRNA-linker-AACGTTAAAAACAGGTCCTCCCCATAACTCTTTCATTGTACACCGCAAGCTCGACACATCGGATTGAAGCATTGTCGCACACAGGATCAGTACCTG TTTTGTCCAGGAGGGGTAATGAGAAGTAACATGTGCCGTTCGAGCTTGTTAGTAGCCTAACTTCGTAACAGCCGTTCTGTAGAAGGTGTGTCCTAGTCATGGAC

CTTTCGCTAACCAAGGCTTTT-OH

GAAAGCGA-PPP ◄ U6 Promoter eRNA11A: (blunt 5' PPP, U6 A start)

tRNA-linker-AACGTTAAAAACAGGTCCTCCCCATAACTCTTTCATTGTACACCGCAAGCTCGACACATCGGATTGAAGCATTGTCGCACACAGGATCAGTACCTG TTTTGTCCAGGAGGGGTAATGAGAAGTAACATGTGCCGTTCGAGCTTGTTAGTAGCCTAACTTCGTAACAGCCGTTCTGTAGAAGGTGTGTCCTAGTCATGGAC

CTTTCGCTTTT-OH

GAAAGCGAAAA-PPP ◄ U6 Promoter eRNA11B: (recessed 5' PPP, U6 G start)

tRNA-linker-AACGTTAAAAACAGGTCCTCCCCATAGCTCTTTCATTGTACACCGCAAGCTCGACACATCGGATTGAAGCATTGTCGCACACAGGATCAGTACCTG TTTTGTCCAGGAGGGTATGAGAAGTAACATGTGCCGTTCGAGCTGTTAGTAGCCTAACTTCGTAACAGCCGTTCTGTAGAAGGTGTGTCCTAGTCATGGAC

CTTTCGGAATTCACCAAGGCTTTT-OH

GAAAGCCTTAAG-PPP ◄ U6 Promoter eRNA41i: (protruding 5' PPP, U6 A start)

tRNA-linker-AACGTTAAAAACAGGTCCTCCCCATAACTCTTTCATTGTACACCGCAAGCTCGACACATCGGATTGAAGCATTGTCGCACACAGGATCAGTACCTG TTTTGTCCAGGAGGGGTATAGAAGTAACATGTGCGGTTCGAGCTTGTTAGTAGCCTAACTTCGTAACAGCCGTTCTGTAGAAGGTGTGTCCTAGTCATGGAC

CTTTT-OH

GAAAGCGA-PPP ◄ U6 Promoter

Figure 21

RNAout DraIII to KpnI selectable marker cacgttgtggtagaattggtaaagagagtcgtgtaaaatatcgagttcgcacatcttgttgtctgattattgattttggcgaaaccatttgat
catatgacaagatgtgtatctaccttaacttaatgattttgataaaaatcattaggtacc

VECTORS AND METHODS FOR GENETIC IMMUNIZATION

This application claims the benefit of Provisional Patent Application Ser. No. U.S. 60/932,160 filed 29 May 2007

STATEMENT REGARDING FEDERALLY SPONSORED RESEARCH OR DEVELOPMENT

This invention was made in part with government support under Grant Numbers 2 R44 GM072141-02, 1 R43 GM080768-01, and 1 R43 AI071660-01A1 awarded by the National Institutes of Health. The government has certain rights in this invention.

FIELD OF THE INVENTION

The present invention relates to a family of eukaryotic expression plasmids useful for gene therapy, obtaining improved genetic immunization, natural interferon production, and more particularly, for improving the immune response to plasmid encoded antigens.

BACKGROUND OF THE INVENTION

The present invention is a family of eukaryotic expression plasmids useful for gene therapy, genetic immunization or interferon therapy. Such molecules and methods for use are useful in biotechnology, gene therapy, cancer and agriculture.

With the invention in mind, a search of the prior art was conducted. DNA vaccines (genetic vaccines) are a potential disruptive technology, that offer the promise of a new way to immunize humans (or animals) with materials that are entirely gene-based and expressed by the organism's own cells, making an ideal mimic of intracellular antigens.

Methods to improve immune responses to DNA vaccine plasmids are described in the art. For example, the efficacy of a DNA vaccine can be further improved, or tailored for systemic or mucosal immunity, or cancer, allergy, bacterial, intracellular parasite or viral targets, by: coimmunization with costimulatory plasmids (e.g. IL12) to modulate the type of response ($T_H1$ versus $T_H2$ bias); cell death inhibitors or enhancers; or optimization of delivery (e.g. electroporation versus gene gun). Some such methods and molecules are described in, Lemieux, P. 2002 *Expert Rev. Vaccines* 1: 85-93; Toka F N, Pack C D, Rouse B T. 2004 *Immunological reviews* 199: 100-112; and Gurunathan S, Klinman D M, Seder R A. 2000 *Annu. Rev. Immunol.* 18: 927-974, and are included herein by reference. DNA vaccination could also involve utilizing different delivery systems in the prime and the boost, as taught by Buchan S, Gronevik E. Mathiesen I, King C, Stevenson F K, Rice J. 2005 *Immunol.* 174: 6292-6298 or different injection sites, as taught by Pavlakis G N, Gragerov A, Felber B K. 2004 US Patent Application US20040241140.

DNA vaccination is ideal for rapid deployment vaccines since development times for DNA vaccines are significantly shorter than those for protein or viral vector systems.

Current Obstacles
Regulatory:

Regulatory issues for use of plasmid DNA in humans have been addressed in several recent World Heath Organization (WHO), US Food and Drug Administration (FDA), or European Agency for the Evaluation of Medicinal Products (EMEA) regulatory draft guidances. A key issue is that antibiotic resistance markers, typically kanamycin resistance, are the most commonly utilized selectable markers. The EMEA guidance [European Medicines Agency, 2001. Note for guidance on the quality, preclinical and clinical aspects of gene transfer medicinal products. CPMP/BWP/3088/99] with regard to DNA vaccine plasmids states: "The use of certain selection markers, such as resistance to antibiotics, which may adversely impact on other clinical therapies in the target population," and "Consideration should be given to avoiding their use, where feasible". Alternative selection strategies to address this concern are needed.

Efficacy:

Protective immunity in humans and other primates has not been broadly obtained using DNA only vaccination. Primate efficacy has been obtained utilizing DNA vaccines in combination with heterologous protein, inactivated organism, or viral vector boosting. Enhanced immune responses have also been reported when plasmid DNA and purified protein (corresponding to the protein encoded in the plasmid) (Dalemans W., Van Mechelen M V, Bruck C, Friede M. 2003 U.S. Pat. No. 6,500,432; Carrera S D, Grillo J M, de Leon LALP, Lasa A M, Feyt R P, Rodriguez A V, Obregon J C A, Rivero N A Donato G M 2004 US Patent Application US20040234543), or inactivated virus, (Rangarajan P N, Srinivasan V A, Biswas L, Reddy G S. 2004 US Patent Application US20040096462) are mixed and coinjected.

However, using plasmids in combination with inactivated organisms, proteins or viral vectors in a vaccine (either as a mixture, or sequentially in a prime boost) eliminates most of the benefits of DNA vaccination, including improved safety, reduced cost, and rapid deployment.

DNA vaccines may be incrementally improved by the following methodologies:

Antigen Expression:

The art teaches that one of the limitations of DNA vaccination is that antigen expression is generally very low. Vector modifications that improve antigen expression (e.g. codon optimization of the gene, inclusion of an intron, use of the strong constitutive CMV or CAGG promoters versus weaker or cell line specific promoter) are highly correlative with improved immune responses (reviewed in Manoj S, Babiuk L A, Drunen S V, en Hurk L V. 2004 *Critical Rev Clin Lab Sci* 41: 1-39). A hybrid CMV promoter (CMV/R), which increased antigen expression, also improved cellular immune responses to HIV DNA vaccines in mice and nonhuman primates (Barouch D H, Yang Z Y, Kong W P, Korioth-Schmitz B, Sumida S M, Truitt D M, Kishko M G, Arthur J C, Miura A, Mascola J R, Letvin N L, Nabel G J. 2005 *J Virol.* 79: 8828-8834). A plasmid containing the woodchuck hepatitis virus posttranscriptional regulatory element (a 600 bp element that increases stability and extranuclear transport of RNA resulting in enhanced levels of mRNA for translation) enhanced antigen expression and protective immunity to influenza hemagglutinin (HA) in mice (Garg S, Oran A E, Hon H, Jacob J. 2002 *J Immunol.* 173: 550-558). These studies teach that improvement in expression beyond that of current CMV based vectors may generally improve immunogenicity.

The art teaches that plasmid entry into the nucleus is a limiting factor in obtaining antigen expression. Increasing nuclear localization of a plasmid through inclusion of NFκB binding sites or a SV40 enhancer improves antigen expression in vitro and in vivo; this is presumed due to binding of NFκB which then piggybacks the plasmid to the nucleus (Dean D A, Dean B S, Muller S, Smith L C. 1999 *Experimental Cell Research* 253: 713-722). However, NFκB is generally localized in the cytoplasm, and transfer to the nucleus is limited, tissue-specific, and dependent on stimulatory signals. This limits the utility of NFκB nuclear targeting to improve DNA vaccination.

$T_H1$ or $T_H2$ Bias:

The art teaches that shifting immune response to DNA vaccine expressed viral or other antigens from $T_H2$ to $T_H1$ is desirable: to elevate humoral and cellular responses; and for other applications, such as allergy or instances where IgG1 ($T_H2$) provide superior protection to IgG2a ($T_H1$) a $T_H2$ biased response is considered optimal. For example, CpG sequences (which promote $T_H1$ response) improved antibody and cytotoxic T lymphocyte (CTL) responses to influenza HA, and CTL responses to influenza nucleoprotein DNA vaccines injected IM (Lee S W, Sung Y C. 1998 *Immunology* 94: 285-289). Coimmunization with IL12 or IL15 $T_H1$ adjuvants improves T cell responses to influenza HA (Chattergoon M A, Saulino V, Shames J P, Stein J, Montaner L J, Weiner D B. 2004 *Vaccine* 22: 1744-1750; Kutzler M A, Robinson T M, Chattergoon M A, Choo D K, Choo A Y, Choe P Y, Ramamathan M P, Parkinson R, Kudchodkar S, Tamura Y, Sidhu M, Roopchand V, Kim J J, Pavlakis G N, Felber B K, Waldmann T A, Boyer J D, Weiner D B. 2005 *J Immunol* 175: 112-123) and antibody mediated protection (Operschall E, Pavlovic J, Nawrath M, Molting K. 2000 *Intervirol* 43: 322-330).

Immunostimulatory Adjuvants:

A number of microbial-specific motifs have been identified that activate innate immunity through Toll like receptor (TLR) binding, for example, Tri-acyl lipopeptides (TLR1/TLR2) peptidoglycan (TLR2), dsRNA (TLR3), bacterial HSP60 or Lipopolysaccharide (LPS; TLR4), flagellin (TLR5), Di-acyl lipopeptide (TLR6), ssRNA (TLR7, TLR8), unmethylated CpG DNA (TLR9). U-rich or U/G rich ssRNA TLR7/8 agonists have been identified that induce interferon responses (Heil F, Hemmi H, Hochrein H, Ampenberger F, Kirschning C, Akira S, Lipford G, Wagner H, Bauer S. 2004 *Science* 303: 1526-1529; Diebold S S, Kaisho T, Hemmi H, Akira S, e Sousa C R. 2004 *Science* 303: 1529-1531; Barchet W, Krug A, Cella M, Newby C, Fischer J A A, Dzionek A, Pekosz A, Colonna M. 2005 *Eur. J. Immunol*. 35: 236-242) as well as a sequence specific siRNA that induces interferon production from human and mice plasmacytoid dendritic cells through TLR7 (Hornung V, Guenthner-Biller M, Bourquin C, Ablasser A, Schlee M, Uematsu S, Noronha A, Manoharan M, Akira S, de Fougerolles A, Endres S, Hartmann G. 2005 *Nature Med.* 11: 263-270). A novel class of immunostimulatory nucleic acid, single stranded CpG RNA which does not require TLR3, 7, 8 or 9 has also been identified (Sugiyama T, Gursel M, Takeshita F, Coban C, Conover J, Kaisho T, Akira S, Klinman D M, Ishii K J. 2005 *J Immunol*. 174: 2273-2279).

These molecules can be utilized as adjuvants to improve DNA vaccination through interferon production. However, exogenously applied adjuvant adds expense, complicates regulatory approval (an additional investigational entity in the vaccine) and requires high dosages since the adjuvant is not targeted (i.e. affects multiple cells in addition to cells containing the DNA vaccine); the high dose of untargeted adjuvant also presents special safety concerns (e.g. autoimmunity, inflammation, sepsis).

Unmethylated CpG is present in the vector backbone of microbial produced plasmids and augmentation (CpG enriched plasmids) can be used to stimulate $T_H1$ responsive innate immune signals through TLR9. Unfortunately, these effects are observed only with high dosages, and CpG effects are minimal with advanced delivery methods which use economically low amounts of antigen (e.g. gene gun) as reflected by a $T_H2$ biased response. As well, the overall poor immunological response to DNA vaccines in humans has been attributed, in part, to significantly reduced expression of TLR9 in humans compared to mice.

Vector encoded protein TLR agonists potentially would induce the innate immune system at low dose, since the signal from these elements is "amplified" from the vector (rather than a fixed vector component such as CpG). Incorporation of a flagellin producing gene into the vector backbone activates innate immune responses and potentiated $T_H1$ bias and cellular immune response to an antigen delivered by Gene Gun. This demonstrates the potential for utilization of amplifiable TLR agonists to potentiate low dose DNA vaccination (Applequist S E, Rollman E, Wareing M D, Liden M, Rozell B, Hinkula J, Ljunggren H G. 2005 *J Immunol.* 175: 3882-3891). However, for inclusion of an innate immunity inducer in a DNA vaccine vector backbone, there should be no associated adaptive immune response since this would limit repeat usage and generate variable results in a population due to attenuated responses in individuals with prior exposure (preexisting immunity). Vectors such as alphaviral replicons (which produce dsRNA adjuvant) or the flagellin producing vector described above contain one or more proteins that can induce adaptive immunity to vector components and are unsuitable for repeat application.

Cell Death:

The art teaches that cell death can augment immune responses to antigens. IM injection of influenza HA and nucleoprotein (N P) DNA vaccines codelivered with mutant caspases that promote slow cell death enhanced T cell responses and cellular immunity (Sasaki S, Amara R R, Oran A E, Smith J M, Robinson H L. 2001 *Nature Biotechnol* 19: 543-547). The immune response to influenza HA and N P is also dramatically enhanced (compared to DNA vaccines) utilizing Semliki forest alphavirus replicon (suicide) vaccines (Berglund P, Smerdou C, Fleeton M N, Tubulekas I, Liljestrom P. 1998 *Nature Biotechnol* 16: 562-565) that induce apoptosis; cell death is critical for the improved immune response. Replicon vectors contain multiple viral replication proteins; immune response against these proteins may limit repeat usage. Apoptotic cell death has also been accomplished by coadministering Fas or mutated caspases 2 or 3, which enhances CTL responses to intramuscularly (IM) administered DNA vaccines. Coadministered caspases also improves immune responses to influenza HA DNA vaccine by Gene Gun (Sasaki et al, Supra 2001). The optimal condition may be to selectively kill muscle or keratinocyte cells (but not immune cells) for a source of antigen for dendritic or langerhans cells (Reviewed in Leitner W W, Restifo N P. 2003 *J Clin invest* 112: 22-24). This is not possible utilizing constitutive cell death promoting agents. Inhibition of apoptosis can also improve immune responses, wherein coadministering antiapoptotic Bcl-XL strongly enhanced T cell response after Gene Gun administration. This may reflect a benefit of prolonging dendritic cell lifespan. However, the use of cell death inhibitors may predispose cells to transformation (in the case of integrated plasmids) and increase cancer risk.

Cytoplasmic dsRNA activates PKR, ADAR, OAS, RIG-I and MDA5, which collectively induce interferon production, inhibit protein synthesis and edit or degrade RNA, thus reducing antigen production eventually leading to apoptotic cell death (reviewed in Wang Q, Carmichael G G. 2004 *Microb. Molec. Biol. Rev.* 68: 432-452). Cell death releases the dsRNA, which can then be taken up by cells, and further induce innate immune response by binding and stimulating endosomalty localized TLR3 (Reviewed in Schroder M, Bowie A G. 2005 *Trends Immunol.* 26: 462-468). The art teaches that this type of dsRNA stimulation occurs with alphavirus replicon (suicide) vaccines. Alphavirus replicon (suicide) vaccines induce enhanced immune responses with 100-1000 fold less antigen compared to standard DNA vaccines (by IM injection). These vectors induce apoptosis, presumed through formation of dsRNA which activates antiviral pathways and eventually leads to apoptotic cell death (Leitner W W, Ying H, Driver D A, Dubensky T W, Restifo N P. 2000 *Cancer Research* 60: 51-55). Cell death is required for improved vaccine efficacy and is mediated by cytoplasmic replicon dsRNA; it is possible that dsRNA in apoptotic elements are phagocytosed by APCs, and induce innate immunity through the endosomal TLR3 dsRNA recognition pathway. Co-delivery of antiapoptotic gene (Bcl-XL) reduced protection, despite increasing antigen production (Leitner W W, Hwang L N, Bergmann-Leitner E S, Finkelstein S E, Frank S, Restifo N P. 2004 *Vaccine* 22: 1537-1544; Leitner W W, Hwang L N, DeVeer M J, Zhou A, Silverman R H, Williams B R G, Dubensky T W, Ying H, Restifo N P. 2003 *Nature Med* 9: 33-39; Matsumoto S, Miyagishi M, Akashi H, Nagai R, Taira K. 2005 *J Biol Chem* 280: 25687-25696). However, a delivery dependent balance between cell death signals and optimal production of antigen is required, since suicide DNA vaccines are not effective with Gene Gun delivery (which transfect dendritic cells) unless an anti-apoptosis gene is included (Kim T W, Hung C F, Juang J, He L, Hardwick J M, Wu T C. 2004 *Gene Ther* 11: 336-342).

Hone, D, Lewis, G, Fouts, T, Bagley, K, Boyson, M, Obriecht, C, Shata, M T, Agwale, S., 2003 World Patent Application WO0219968 disclose DNA vaccines that coexpress antigens in combination with biologically-active components, such as adjuvants, immunoregulatory agents, antisense RNAs, and/or catalytic RNAs. Immunoregulatory agents are defined as peptides or proteins, and use of immunostimulatory RNA is not disclosed or contemplated by the inventors.

Polio, J M, Dubensky, T W, Belli, B A, Perri, S, Fong, T. 2000 World Patent Application WO0061770 disclose expression cassettes comprising a promoter operably linked to a nucleic acid molecule which, when transcribed in vivo, forms double-stranded RNA (dsRNA) that induces the production of interferon. Compositions and methods were provided for the expression of noncoding dsRNA in the context of expression of a desired antigen with the object to enhance the overall robustness of antigen-specific immune responses. The authors teach that induction of Type I and II interferon's as a result of the intracellularly produced dsRNA in turn induces the synthesis of protein kinase R (PKR), and 2'-5 oligoadenylate synthetase (OAS), causing apoptosis and protein expression inhibition. A mechanism for induction of interferons by dsRNA is not disclosed. The authors do not teach activation of interferon production utilizing MDA5 or RIG-I signaling.

Williams J A 2006 World Patent Application WO2006078979 teach expression of immunostimulatory RNA from the vector may be used to activate cytoplasmic RNA pattern receptors such as PKR, RIG-I or MDA5, or, after cell death, TLR3 (dsRNA) or TLR7/8 (ssRNA) through uptake by bystander cells.

Even in view of the prior art, there remains a need for improved DNA vaccine vectors that are minimized to eliminate extraneous DNA, do not require antibiotic selection, are organized to ensure high quality bacterial plasmid productivity and improved in vivo expression, and induce improved innate and adaptive immune responses to the target antigen (but not the vector backbone), such that this technology can be utilized to meet the efficacy threshold in humans and other mammals, birds or fish with a wide range of target antigens.

DISCLOSURE OF THE INVENTION

The invention relates to a family of eukaryotic expression plasmids useful for gene therapy, genetic immunization and or interferon therapy.

Improved vectors encoding expressed RNA sequences (RNA elements, eRNA), in addition to the protein antigen expression element are disclosed. These expressed RNA sequences add additional functionality to the vector to improve expression and enhance immune responses. The RNA elements induce interferon production through activation of cellular RNA receptors, including but not limited to RIG-I and MDA5. Preferred RNA element compositions for activating RIG-I and MDA5 cytoplasmic RNA receptors without activating PKR are disclosed. Due to the small size of an RNA expression element (100-500 bp), multiple elements can be included within a single plasmid. Composite RNA elements comprising two dissimilar RNA elements that synergistically activate RIG-I and increase protein antigen expression are disclosed. Plasmid encoded adenoviral VARNAI is disclosed as a potent MDA5 activator. Since RNA does not induce adaptive immune responses against itself, the response to RNA containing vectors is not dependent on prior exposure of the patient, and can therefore be utilized repeatedly, without inducing immune responses to the vector backbone.

Improved vectors that utilize a novel RNA based non antibiotic selectable marker are also disclosed.

Improved vectors that utilize a novel chimeric promoter that improves antigen expression are also disclosed.

BRIEF SUMMARY OF THE INVENTION

It is a purpose and/or objective of the present invention to provide DNA vaccine plasmids for inducing immune responses through DNA vaccination. It is a purpose and/or objective of the present invention to provide expression plasmids for gene therapy. Another disclosure is improved DNA vaccine plasmid compositions that, compared to plasmids defined in the art such as VR1012, pVAX1, pVC0396, pCMVkm2, pITR, pPJV7563, pWG4303, or pCOR vectors, or their derivatives, are improved by: increased eukaryotic expression of target antigen by incorporation of a chimeric CMV promoter-HTLV R-U5-synthetic rabbit β globin 3' intron acceptor; and smaller size by elimination of all extraneous sequences such as additional sequences flanking the prokaryotic origin or antibiotic resistance genes as a consequence of using the nearest useful restriction sites for vector construction. This includes: removal of potentially recombinogenic transposon termini present in other vectors, for example VR1012; smaller size by incorporation of a chimeric HTLV R-U5-synthetic rabbit β globin 3' intron acceptor in place of the larger CMV intron; smaller size by incorporation of a short synthetic eukaryotic transcription terminator to replace the large bovine Growth hormone terminator or native rabbit β globin terminator; improved plasmid yield and integrity during bacterial production by inclusion of a transcriptional terminator downstream of the prokaryotic replication origin to protect against target antigen expression; improved plasmid integrity during bacterial production by removal of additional sequences, such as polyG polyC tails, used in construction of VR1012, that may promote dimer or concatamer formation during bacterial propagation; improved plasmid yield and integrity during bacterial production by optimization of the selectable marker gene, origin of replication orientation; reduced size and improved safety, vaccination consistency between patient populations, and regulatory compliance by elimination of potentially expressed antigenic peptide fragments by elimination of extraneous sequences between the stop codon of the gene of interest and the transcriptional terminator, such as a fragment of SIVnef (present immediately downstream of the stop codon in pWG4303 and derivatives) or a 178 amino acid fragment of the hepatitis C virus (HCV) polymerase gene (present immediately downstream of the stop codon in pPJV7563 and derivatives); and reduced size and improved safety and regulatory compliance by replacement of the kanamycin resistance gene with a small RNA based non-antibiotic selectable marker.

Yet another objective and/or purpose of the invention are new compositions to improve the efficacy of DNA vaccination. The vectors of the current invention are used to improve the effectiveness of DNA vaccines by increasing target gene expression compared to DNA vaccine plasmids defined in the art. Novel compositions of expressed RNA-containing DNA vaccine vector backbones that improve the immunogenicity of DNA vaccination are disclosed. The vector backbones of the current invention encode novel, expressed immunostimulatory RNA compositions, in addition to the optimized protein antigen expression element. These expressed RNA sequences activate interferon production and innate immune response through cellular RNA receptors. Yet another objective and/or purpose of the invention are RNA element compositions that induce natural interferon production in an individual. Due to the small size of an RNA expression element (typically 100-500 bp), multiple elements can be included within a single plasmid; in the case of multiple plasmid immunization, different RNA elements may be included on each plasmid. Yet another objective and/or purpose of the invention are to further increase immunostimulation by utilization of composite RNA elements comprising two dissimilar RNA elements. These composite RNA elements unexpectedly synergistically activate cytoplasmic RNA receptor RIG-I. Since RNA does not induce adaptive immune responses to itself, the response to RNA containing vectors is not dependent on prior exposure of the immunized individual, and can therefore be utilized repeatedly, without inducing immune responses to the vector backbone.

In summary, the vectors combine reduced size, sequence content, and antibiotic free selection (which improves regulatory compliance and potency), with improved plasmid production yield, plasmid production integrity, eukaryotic gene expression, genome recombination propensity (safety), and regulation of innate immune responses by RNA elements.

Further objects and advantages of the invention will become apparent from a consideration of the drawings and ensuing description.

BRIEF DESCRIPTION OF THE DRAWING FIGURES

FIG. 1. Immunostimulatory pDNAVACCultra plasmid NTC8382-41H-HA

Figure 2:
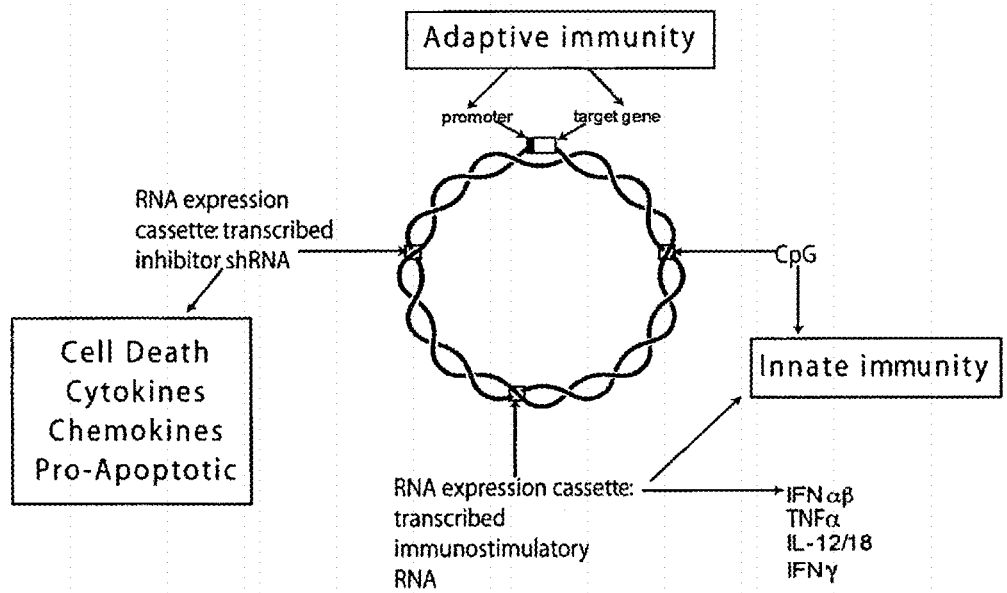

FIG. 2. Action of vector incorporated immunostimulatory RNA elements

Figure 3:
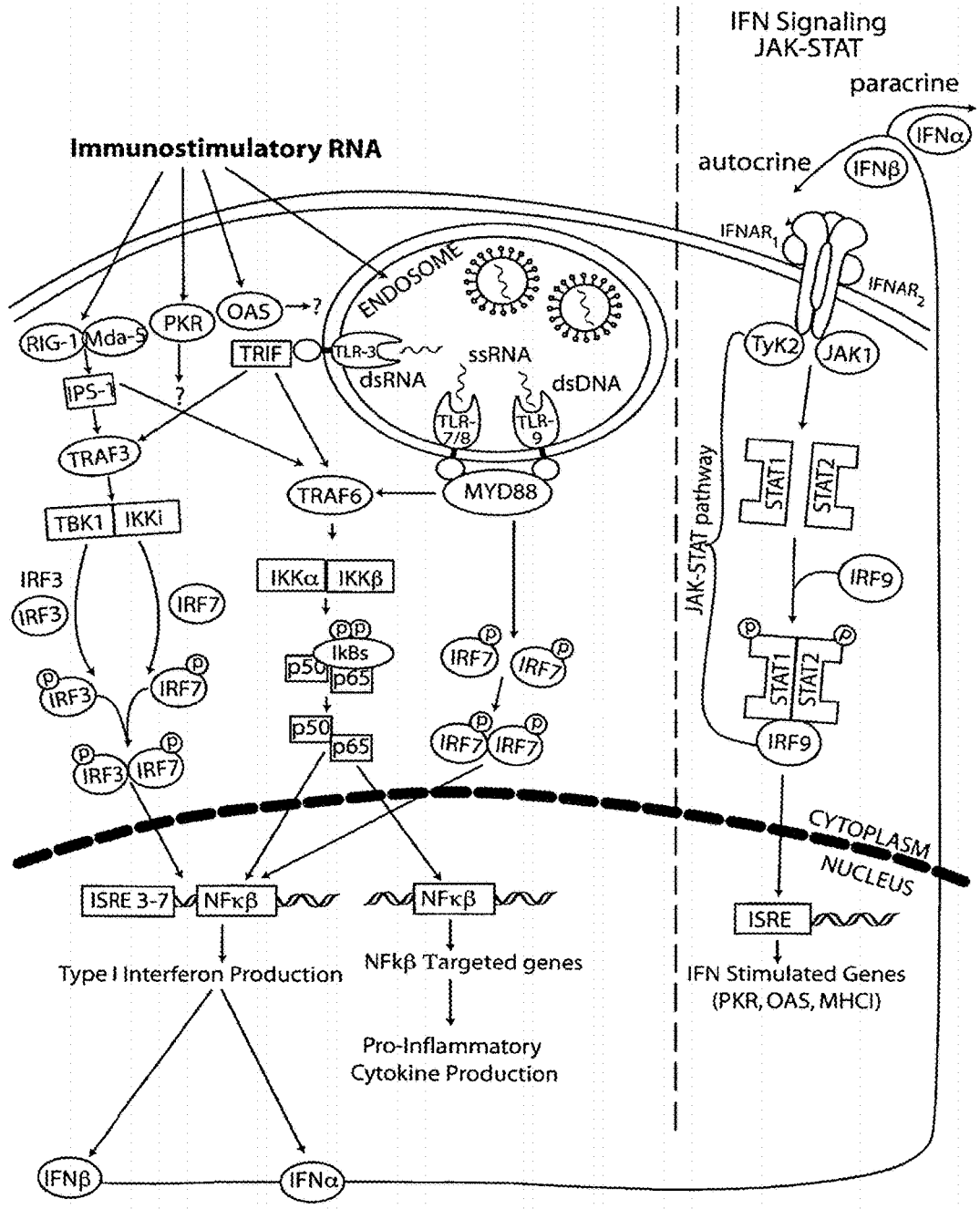

FIG. 3. Immunostimulatory RNA activation pathways

FIG. 4. eRNA11 derivatives, with blunt, recessed, or protruding 5' ends

Figure 5:
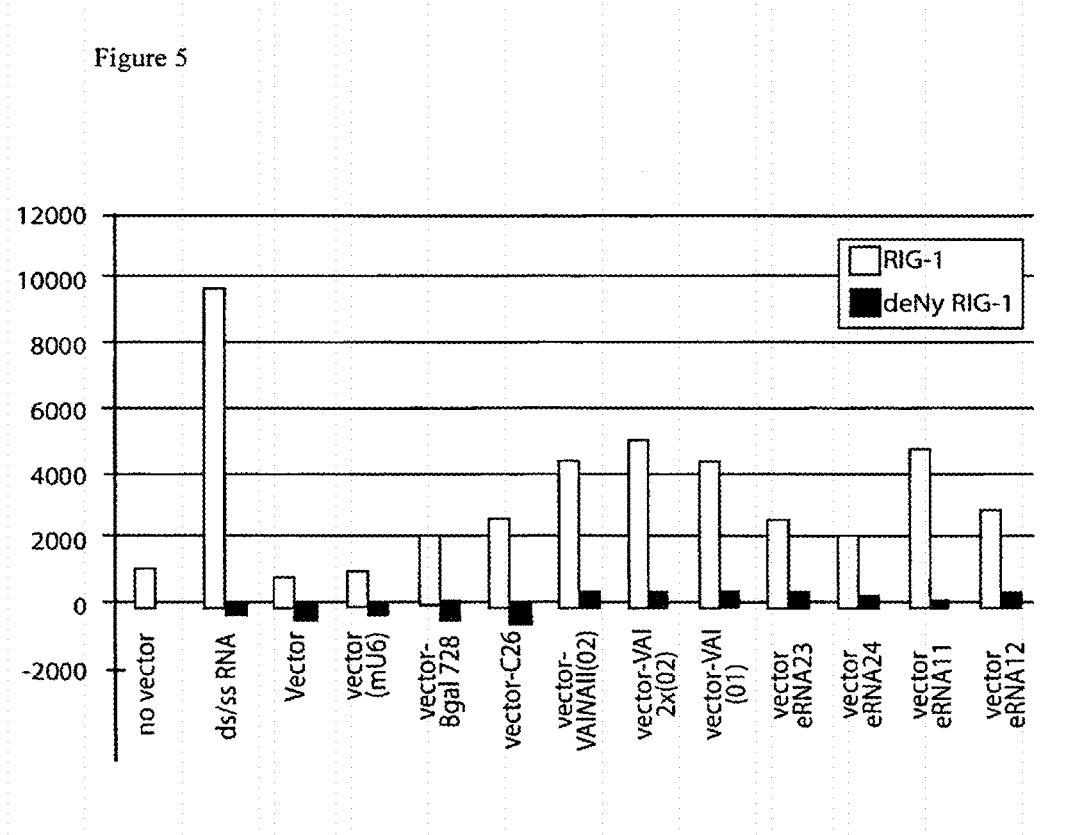

FIG. 5. Activation of the Interferon β promoter by eRNA plasmids

Figure 6:
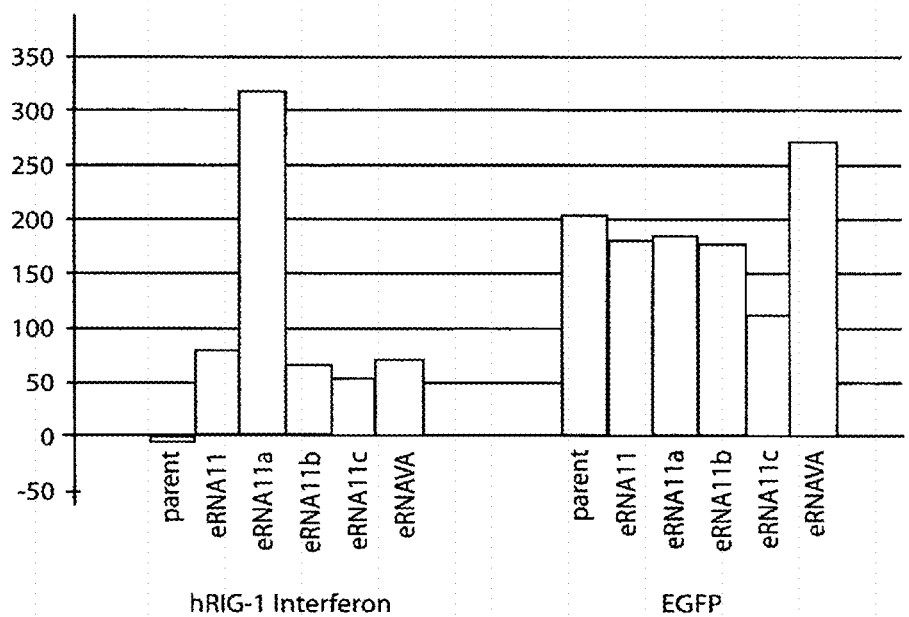

FIG. 6. Optimization of eRNA11: blunt 5' end (11a) is optimal

Figure 7:
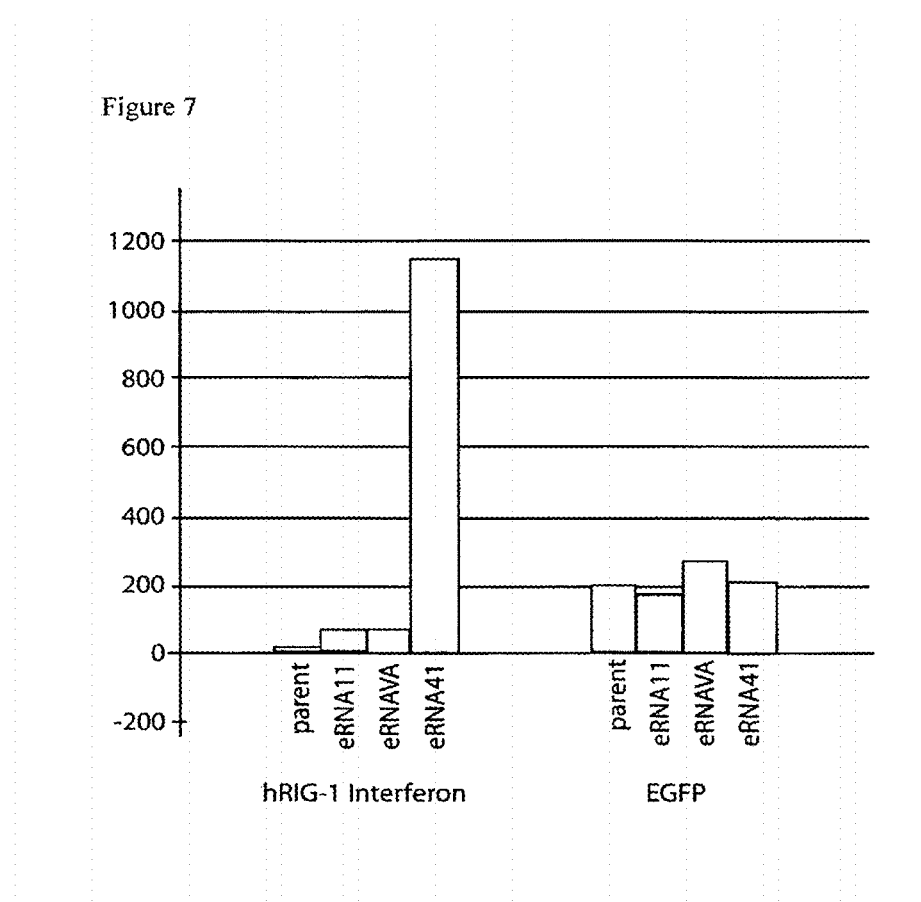

FIG. 7. Synergistic RIG-I activation with composite eRNA41 (11+VARNAI)

Figure 8:
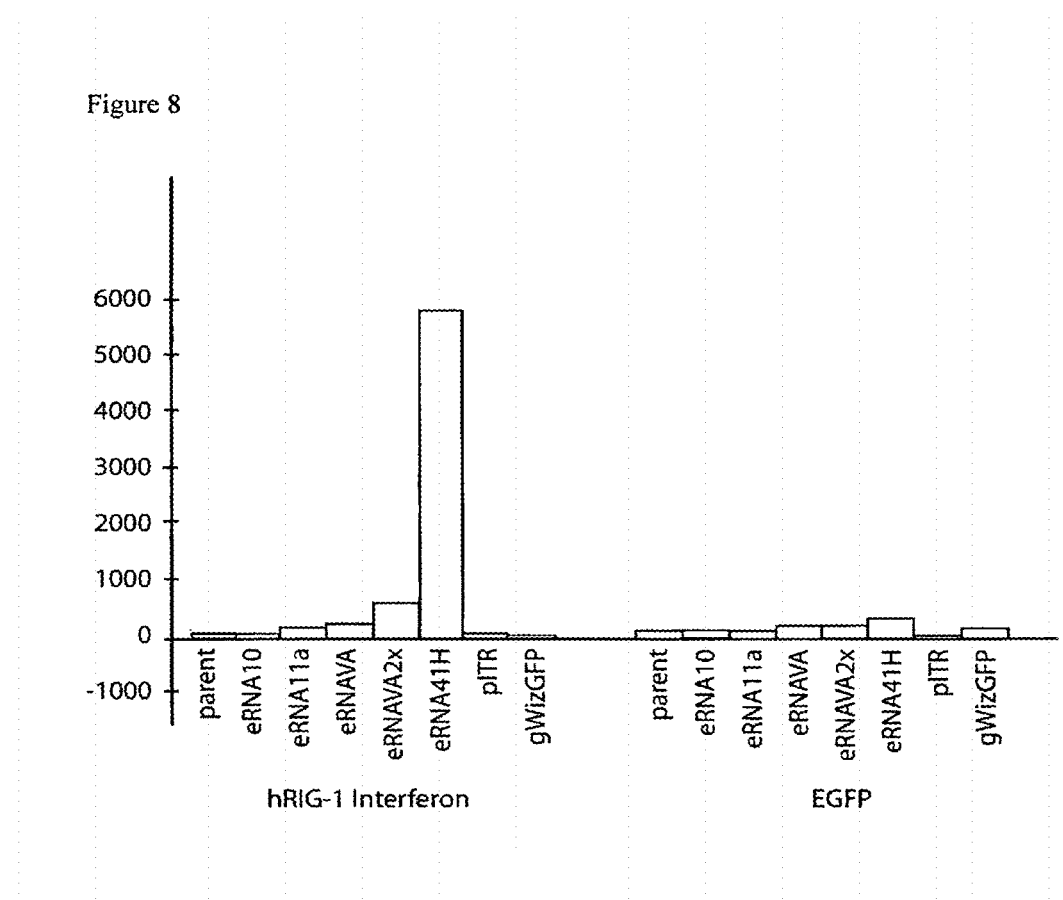

FIG. 8. Synergistic RIG-I activation with composite eRNA41H (11a+VARNAI)

Figure 9:
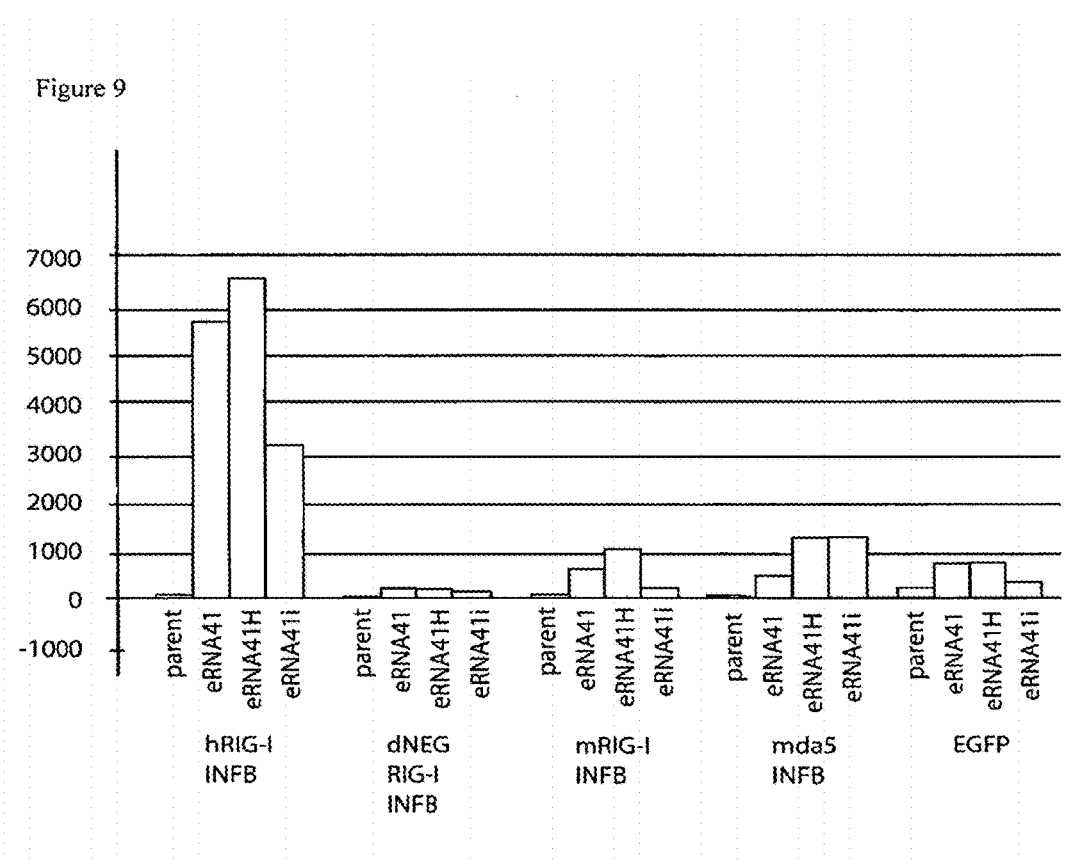

FIG. 9. Blunt 5' end (41H) is a stronger RIG-I activator than recessed (41) or extended (41i)

Figure 10:
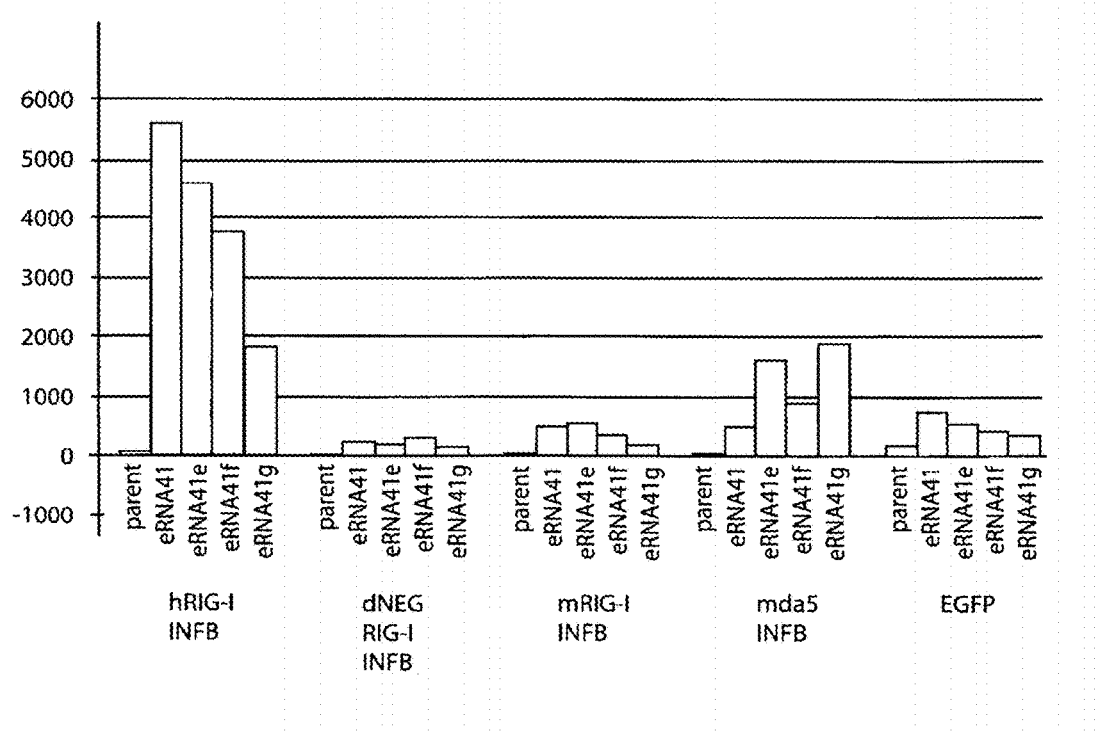

FIG. 10. eRNA41 optimization: Orientation independence

Figure 11:
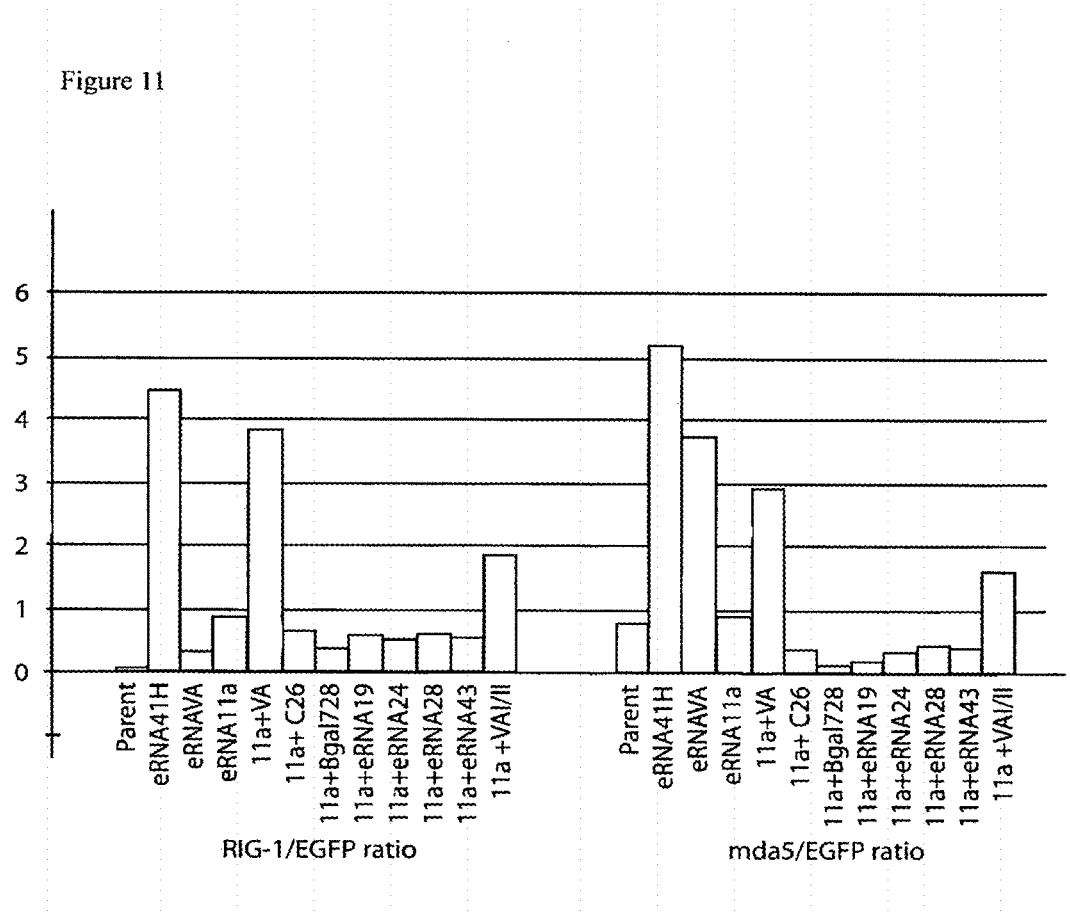

FIG. 11. RIG-I and MDA5 activation by VARNAI component of eRNA41H

Figure 12:
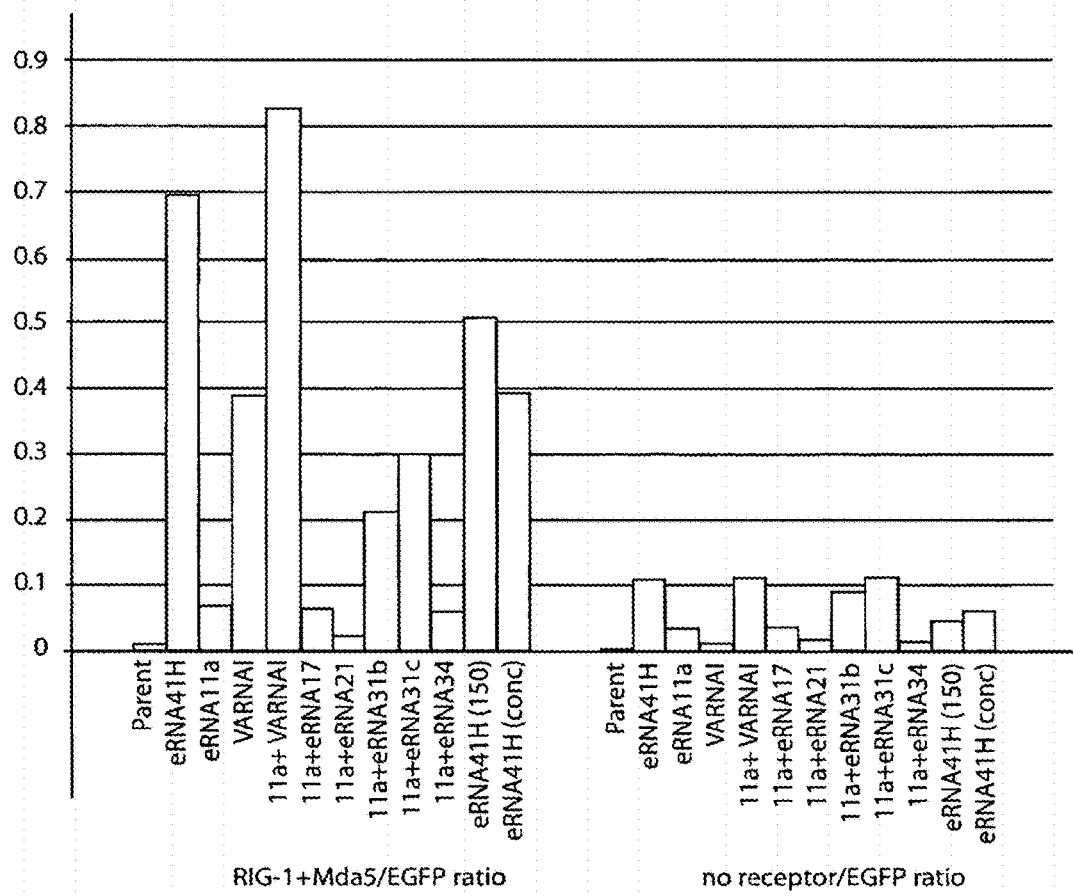

FIG. 12. Synergy of eRNA11a and VARNAI

Figure 13:
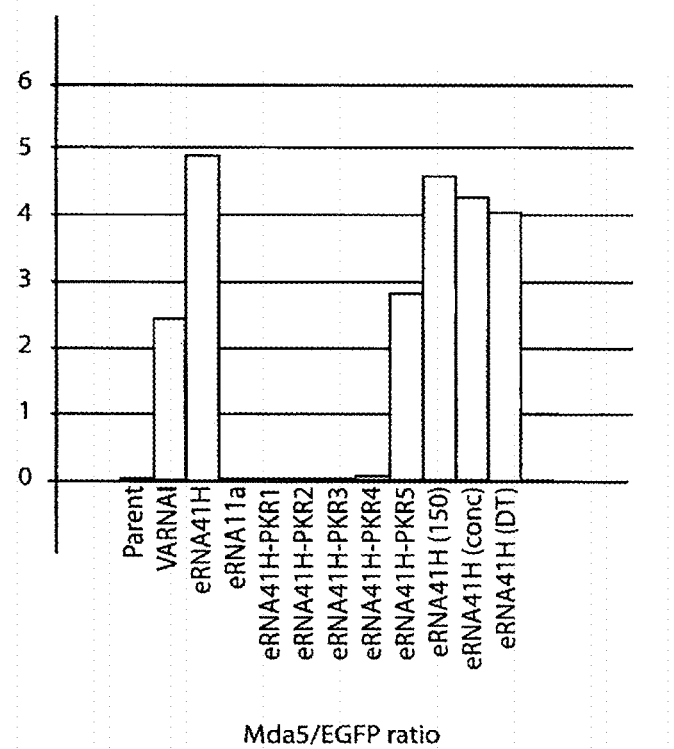

FIG. 13. Synergy of eRNA11a and VARNAI for MDA5 activation is eliminated in PKR1-4

Figure 14:
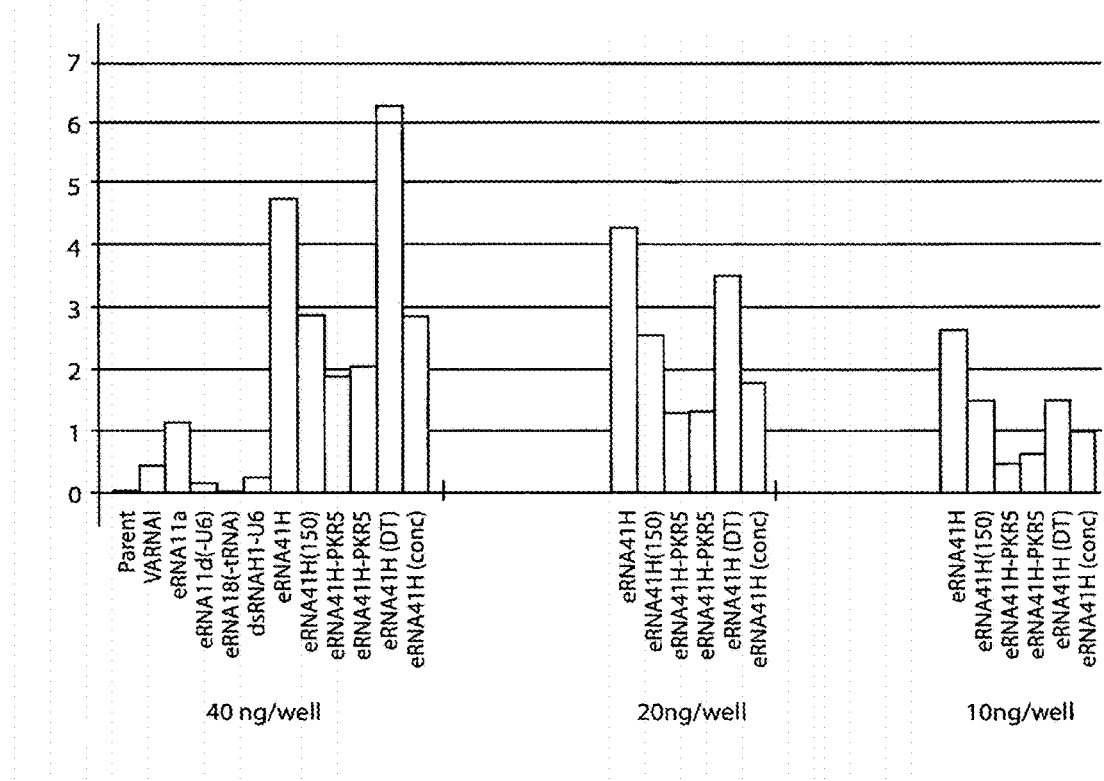

FIG. 14. RIG-I activation requires specific RNA structures

Figure 15:
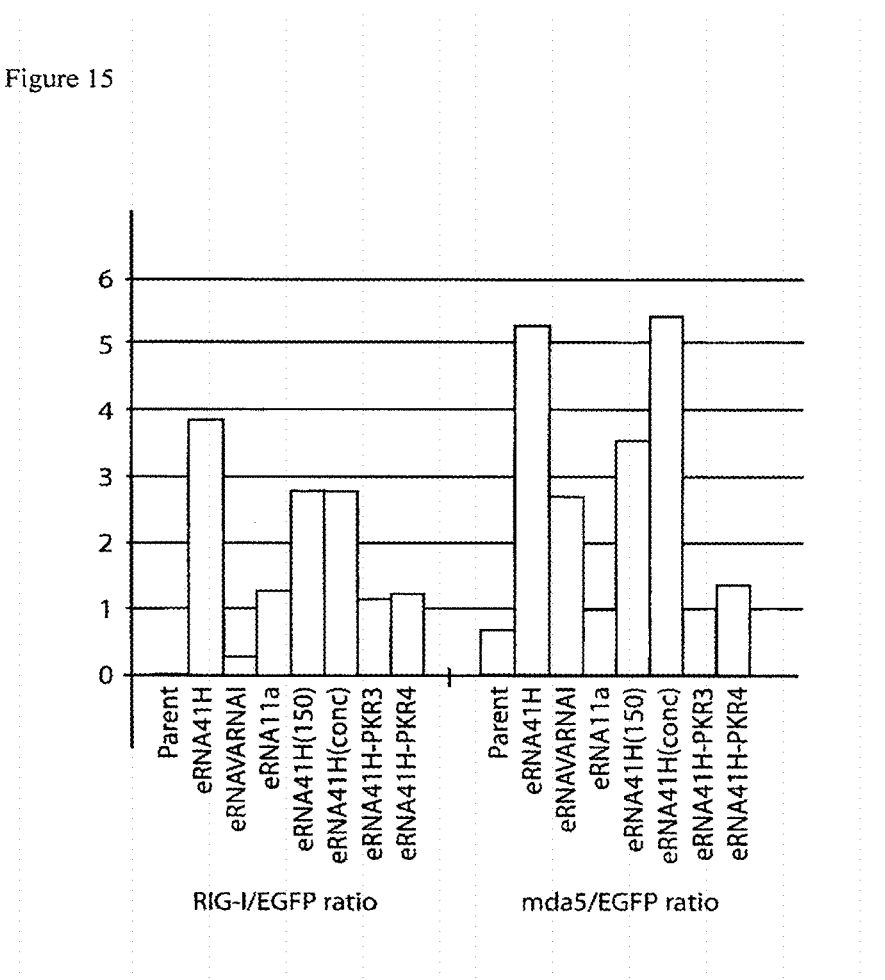

FIG. 15. eRNA41H-PKR3 and eRNA41H-PKR4 vectors eliminate MDA5 activation

Figure 16:
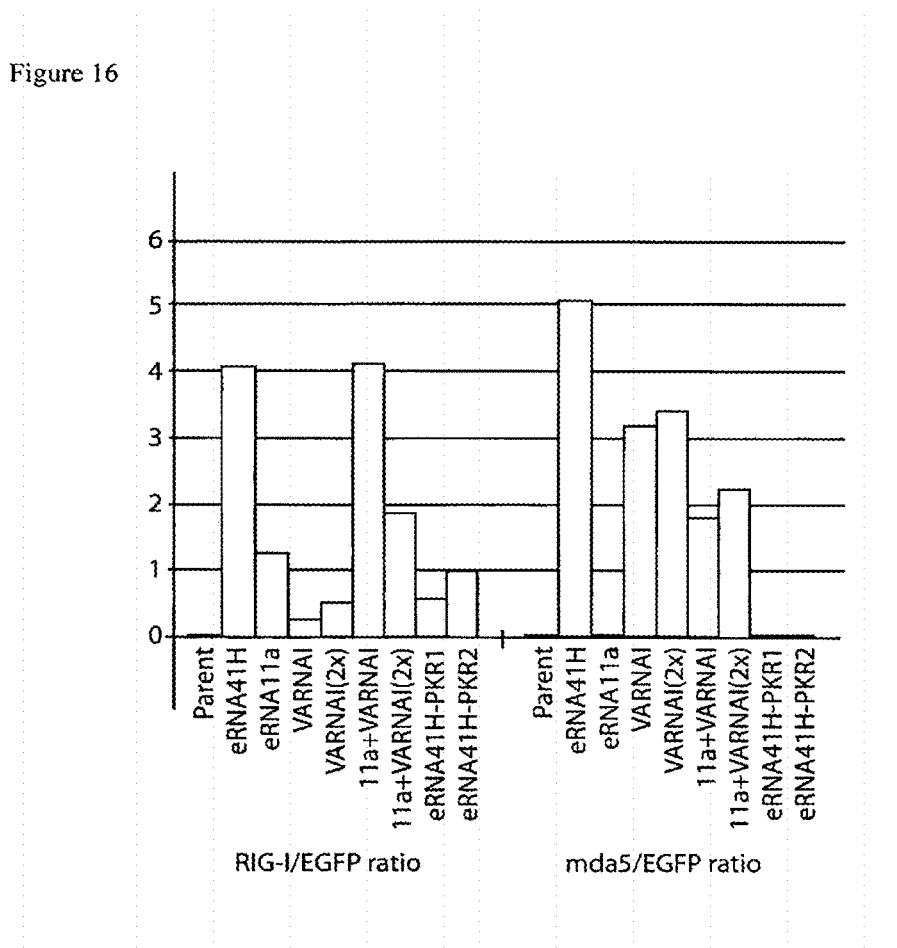

FIG. 16. eRNA41H-PKR1 and eRNA41H-PKR2 vectors eliminate MDA5 activation

Figure 17:
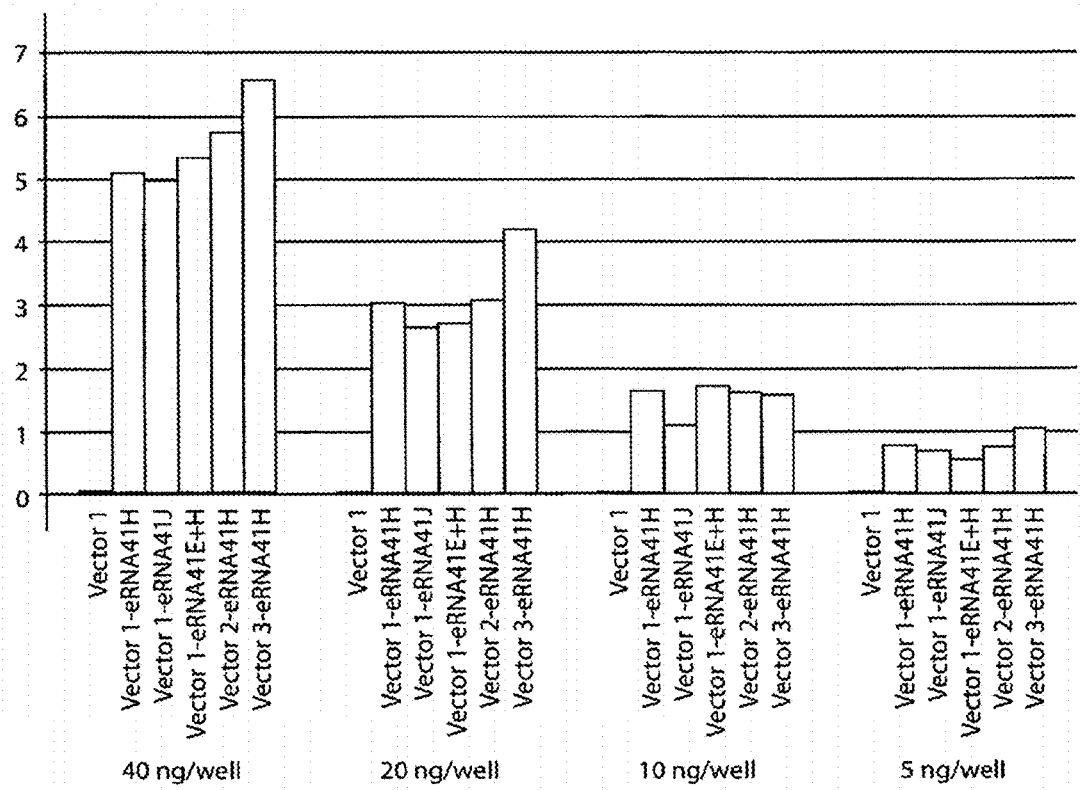

FIG. 17. RIG-I activation by composite eRNA vectors is independent of vector backbone and eRNA orientation FIG. 18. NTC7382 promoter FIG. 19. IS10 functional map, with locations of RNA IN and RNA-OUT regulatory RNAs FIG. 20. Integration plasmid pCAH63-Cat, containing RNA-IN controlled SacB counterselectable marker FIG. 21. RNA-OUT sequence as adapted for cloning into DNA vaccine plasmid FIG. 22. RNA-OUT DNA vaccine plasmid fermentation production FIG. 23. NTC7382 41H-HA and NTC7382-41H-M-HA Table 1: eRNA constructs Table 2: Composite eRNA constructs Table 3: Anti-HA response to eRNA plasmids Table 4: Expression levels (EGFP Fluorescence units) from plasmids incorporating the NTC7382, SV40-NTC7382, or CMV based promoter Table 5: NTC7382 41H-HA, NTC7382-41H-M-HA and NTC8382-41H-HA in vivo expression and immunogenicity

DETAILED DESCRIPTION OF THE INVENTION

Turning now to the drawings, in FIG. 1, an immunostimulatory influenza H5 HA 'bird flu' pDNAVACCultra plasmid (NTC8382-41H-HA) is shown. The RNA-OUT selectable marker is cloned as a 140 bp DraIII-KpnI fragment, replacing the kanR gene in the otherwise equivalent NTC7382 vector. The immunostimulatory RNA element (41H) is cloned between the Eukaryotic terminator and the prokaryotic replication origin in this case. However, the RNA element could be cloned at other permissive sites in the plasmid, for example at either end of the selectable marker. As well, the RNA element could be cloned at permissive sites in other gene delivery vehicles, including viral (e.g. alphavirus, poxvirus, lentivirus, retrovirus, adenovirus, adenovirus related virus, etc) and nonviral (e.g. plasmid, midge, transcriptionally active PCR fragment, minicircles, bacteriophage, etc) vectors. Permissive sites for cloning an RNA element into a different vector can be determined by one skilled in the art.

In FIG. 2, the application of immunostimulatory RNA element containing DNA vaccines to improve DNA vaccination is illustrated. Immunostimulatory RNA may improve innate or adaptive immune responses to the vector encoded antigen through activation of cytokine or chemokine signals, upregulation of MHC molecules or proteosome peptide processing in response to type I interferon signaling, etc. Immunostimulatory RNA may also increase antigen expression through increasing transcription from the plasmid promoter, decreasing translation shutdown or mRNA degradation or editing (e.g. through repression of: PKR mediated translation arrest; ADAR mediated RNA editing; OAS triggered RNA degradation through activation of RNase L; dicer mediated RNA silencing), or increasing plasmid nuclear import (e.g. through NFκβ activation).

In FIG. 3, immunostimulatory RNA mediated activation of multiple signaling pathways to produce type 1 interferon and/or inflammatory cytokines is shown. Plasmid-produced immunostimulatory RNA may induce IPS-1 (also called MAVS, VISA or Cardiff) through RIG-I and/or mda-5 (RIG-I-like receptors, RLRs) activation, which leads to type 1 interferon production and activation of proinflammatory cytokines (Kawai T, Takahashi K, Sato S, Boban C, Kumar H, Kato H, Ishii K H, Takeuchi O, Akira S. 2005 *Nature Immunol.* 6: 981-988). Immunostimulatory RNA could also activate endosomally localized TLR3 or TLR7/8 (TLRs) after autophagy or (in non-transfected cells) through phagocytosis, pinocytosis, or receptor mediated uptake after cell death. Immunostimulatory RNA may also potentially activate interferon production through PKR or OAS signaling through undefined pathways (? in Figure). As well, immunostimulatory RNA could induce interferon production through activation of NALP3 or other inflammasome receptors. Up-regulation of MHCI receptors on cells responding to type 1 interferon may increase antigen presentation and improve adaptive immune responses.

In FIG. 4, the sequences of predicted dsRNA from eRNA11 and eRNA11A, eRNA11B, and eRNA41i derivatives, with blunt, recessed, or protruding U6 transcript 5' ends are shown. For the purpose of the figure the 5' U6 promoter end is denoted by PPP, other structures are possible.

In FIG. 5, RIG-I mediated activation of the Interferon β promoter (luminescence) by eRNA vectors in a two step assay is shown. 'Vector' denotes the pDNAVACCUltra EGFP backbone. hRIG-I mediated interferon induction (Y axis, luminescence from 3 interferon-luciferase reporter), versus negative control dominant negative (deNy) hRIG-I, is shown for each construct (X axis).

In FIG. 6, optimization of eRNA11 is shown, as determined by hRIG-I mediated activation of the Interferon β promoter in a one step assay. Blunt 5' end (11a) is optimal. hRIG-I interferon induction (Y axis, luminescence from β interferon-luciferase reporter) and EGFP expression (Y axis, fluorescence from EGFP DNA vaccine plasmid) for each construct (X axis) is shown.

In FIG. 7, synergistic activation of hRIG-I with composite eRNA41 (eRNA11+VARNAI) compared to VARNAI (VA) or eRNA11 components, is demonstrated as determined by hRIG-I mediated activation of the Interferon β promoter in a one step assay. hRIG-I interferon induction (Y axis, luminescence from β interferon-luciferase reporter) and EGFP expression (Y axis, fluorescence from EGFP DNA vaccine plasmid) for each construct (X axis) is shown.

In FIG. 8, synergistic activation of hRIG-I with composite eRNA41H (eRNA11a+VARNAI) compared to additive activation with composite 2×VARNAI (VA2×) as determined by RIG-I mediated activation of the Interferon β promoter in a one step assay. hRIG-I interferon induction (Y axis, luminescence from β interferon-luciferase reporter) and EGFP expression (Y axis, fluorescence from EGFP DNA vaccine plasmid) for each construct (X axis) is shown. pITR does not contain EGFP.

In FIG. 9, a blunt 5' end is demonstrated as optimal for human or murine RIG-I activation in composite eRNA in a one step assay. Blunt 5' end (41H)>than recessed (41) or extended (41i). Luminescence, as determined by RIG-I or MDA5 mediated activation of the Interferon 13 promoter (Y axis) and EGFP expression (Y axis, fluorescence from EGFP DNA vaccine plasmid) versus constructs (x axis).

In FIG. 10, synergistic activation of human and murine RIG-I by VARNAI and eRNA11 in composite eRNAs is demonstrated to be orientation independent in a one step assay. Luminescence as determined by receptor (RIG-I or MDA5) mediated activation of the Interferon β promoter (Y axis) and EGFP expression (Y axis, fluorescence from EGFP DNA vaccine plasmid) versus constructs (x axis).

In FIG. 11, RIG-I and MDA5 activation by VARNAI component of eRNA41H is shown in a one step assay. (left) Synergy of eRNA11a and VARNAI (eRNAVA) for RIG-I activation observed in cis (eRNA41H) or trans (11a+V A). 40 ng of each test plasmid was utilized per transfection well along with 150 ng of an internal control EGFP plasmid to standardize for transfection efficiency. (right) VARNAI is a potent MDA5 activator and VAI component accounts for bulk of strong MDA5 activation observed with eRNA41H. 100 ng of each test plasmid was utilized per transfection well along with 150 ng of an internal control EGFP plasmid to standardize for transfection efficiency. Ratio of Luminescence (RIG-I or MDA5 activation) to fluorescence (EGFP from internal control) (Y axis) versus constructs (x axis) is shown.

In FIG. 12, the synergy of eRNA11a and VARNAI is shown. 40 ng of each test plasmid was utilized per transfection well along with 150 ng of an internal control EGFP plasmid to standardize for transfection efficiency and 20 ng each of RIG-I and MDA5 receptors (left) or no receptors (right) in a one step assay. Synergy is observed in cis (eRNA41H) or trans (11a+V A) with or without receptors. Ratio of Luminescence (β interferon promoter activation) to fluorescence (EGFP internal control) (Y axis) versus constructs (x axis) is shown.

In FIG. 13, specific VARNAI secondary structures required for MDA5 activation is demonstrated to be eliminated in PKR1-4 but not PKR5 in a one step assay. 100 ng of each test plasmid was utilized per transfection well along with 150 ng of an internal control EGFP plasmid to standardize for transfection efficiency. Ratio of Luminescence (MDA5 activation) to fluorescence (EGFP) (Y axis) versus constructs (x axis) is shown.

In FIG. 14, RIG-I activation is shown to require specific RNA structures. The results of a one step RIG-I activation assay with the indicated plasmids and hRIG-I receptor. 40 ng (all test plasmids), 20 ng or 10 ng (last 6 test plasmids only) of each test plasmid was utilized per transfection well as indicated along with 150 ng of an internal control EGFP plasmid to standardize for transfection efficiency. Luminescence (RIG-I activation) to fluorescence (EGFP) ratio (Y axis) versus constructs (x axis) is shown. dsRNAHI-U6 construct is construct H1-mU6 (StuI) INF dsRNA repaired.

In FIG. 15, the eRNA41H-PKR3 and eRNA41H-PKR4 vectors are shown to have eliminated both MDA5 activation and synergistic RIG-I activation in a one step assay (left) Synergy of eRNA41H (eRNA11a and VARNAI) for RIG-I activation is eliminated in eRNA41H-PKR3 and eRNA41H-PKR4. 40 ng of each test plasmid was utilized per transfection well along with 150 ng of an internal control EGFP plasmid to standardize for transfection efficiency. (right) eRNA41H-PKR3 and eRNA41H-PKR4 VARNAI central domain substitutions eliminate MDA5 activation observed with eRNA41H. 100 ng of each test plasmid was utilized per transfection well along with 150 ng of an internal control EGFP plasmid to standardize for transfection efficiency. Ratio of Luminescence (RIG-I or MDA5 activation) to fluorescence (EGFP) (Y axis) versus constructs (x axis) is shown.

In FIG. 16, the eRNA41H-PKR1 and eRNA41H-PKR2 vectors are shown to have eliminated both MDA5 activation and synergistic RIG-I activation in a one step assay (left) Synergy of eRNA41H (eRNA11a and VARNAI) for RIG-I activation is eliminated in eRNA41H-PKR1 and eRNA41H-PKR2. 40 ng of each test plasmid was utilized per transfection well along with 150 ng of an internal control EGFP plasmid to standardize for transfection efficiency. (right) eRNA41H-PKR1 and eRNA41H-PKR2 VARNAI variants eliminate MDA5 activation observed with eRNA41H. 100 ng of each test plasmid was utilized per transfection well along with 150 ng of an internal control EGFP plasmid to standardize for transfection efficiency. Ratio of Luminescence (RIG-I or MDA5 activation) to fluorescence (EGFP) (Y axis) versus constructs (x axis) is shown. VARNAI (2×) is a double insert of VARNAI.

In FIG. 17, RIG-I activation by composite eRNA vectors is demonstrated to be independent of vector backbone and eRNA orientation. The results of a one step RIG-I activation assay with 40, 20 10 or 5 ng per well of the indicated plasmids along with 150 ng of an internal control EGFP plasmid to standardize for transfection efficiency. Luminescence (RIG-I activation) to fluorescence (EGFP) ratio (Y axis) versus constructs (x axis) is shown. Vector 1=pDNA-VACCUltra SV40 CMV HLTV-1 R-U5 Rabbit β globin intron NTC-HA, Vector 2=RNA-OUT antibiotic free version of Vector 1, Vector 3=pDNAVACCUltra SV40 CMV NTC-HA.

Figure 18:
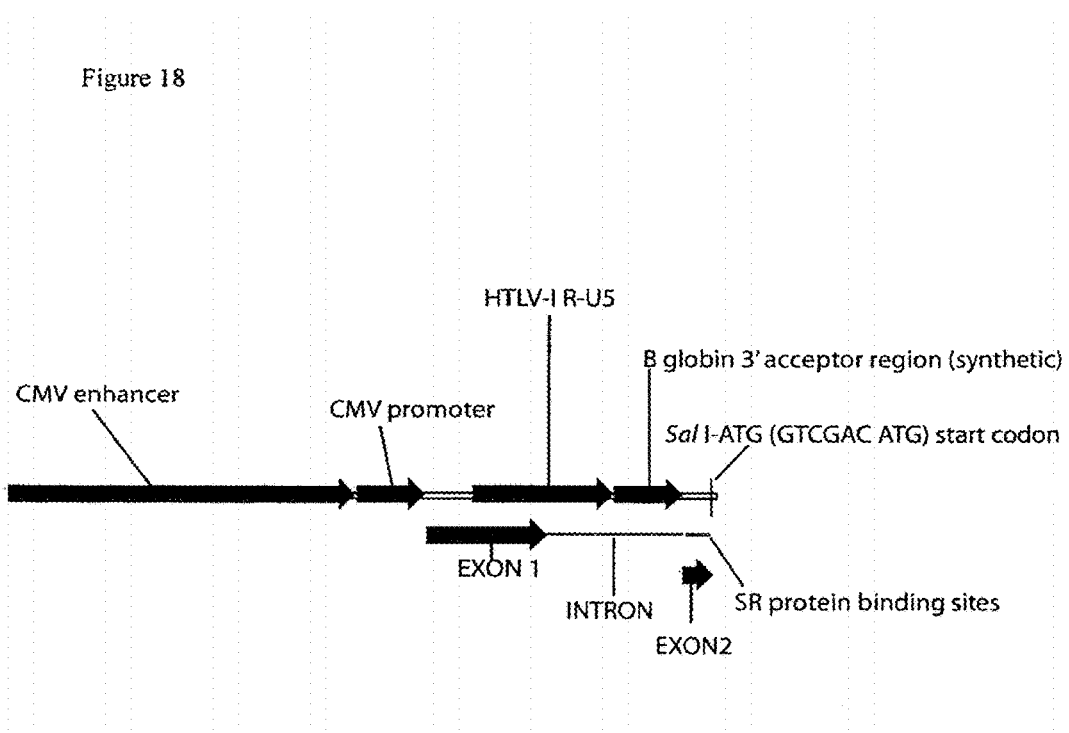

In FIG. 18, an annotated map of the NTC7382 promoter is shown.

Figure 19:
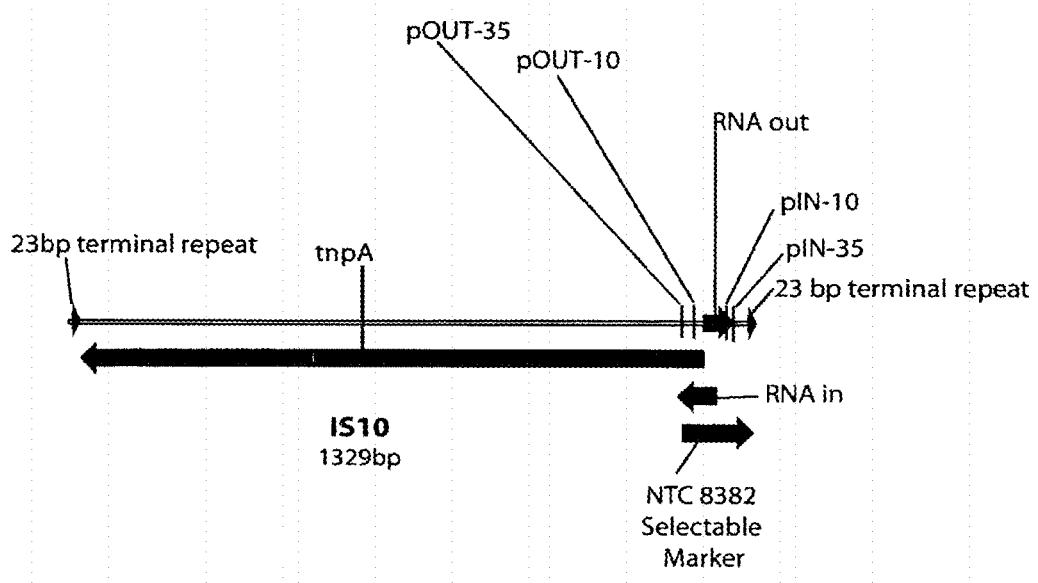

In FIG. 19, the IS10 functional map, with locations of RNA IN and RNA-OUT regulatory RNAs is shown.

Figure 20:
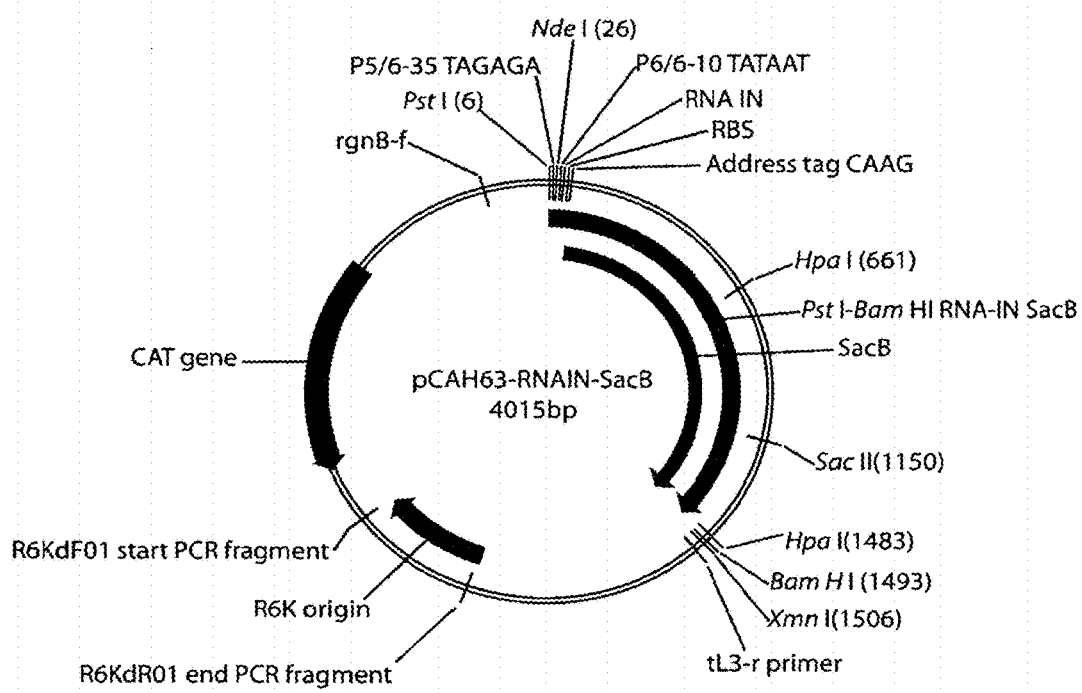

In FIG. 20, the integration plasmid pCAH63-Cat, containing P5/6 6/6 RNA-IN controlled SacB counterselectable marker is shown (pCAH63-RNA-IN-SacB=pCAH63-CAT RNA-1N-SacB (P5/6 6/6)).

In FIG. 21, the RNA-OUT sequence as adapted for cloning into DNA vaccine plasmid is shown. Flanking DraIII (cacgttgtg) and KpnI (ggtacc) sites are underlined.

Figure 22:
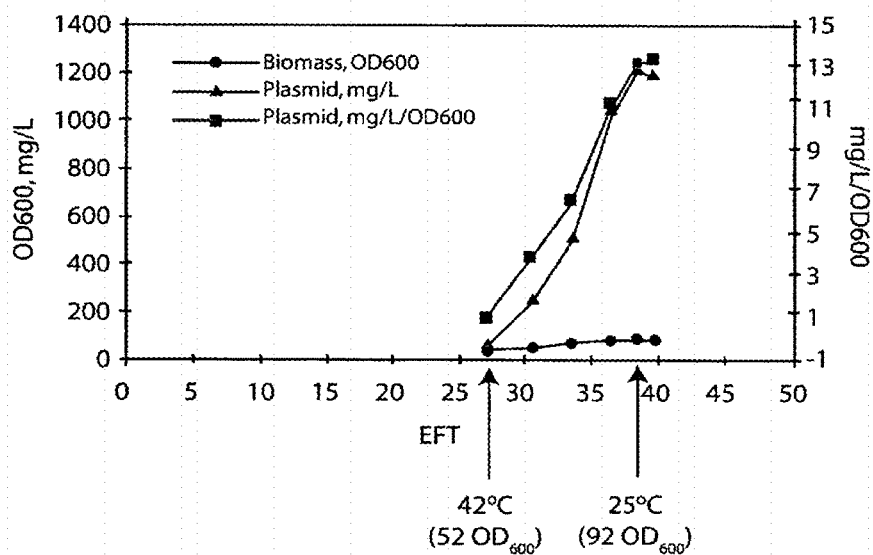

In FIG. 22, analytical data including production yield from an RNA-OUT influenza DNA vaccine plasmid fermentation (RNA-OUT-41H-HA) is shown.

Figure 23:
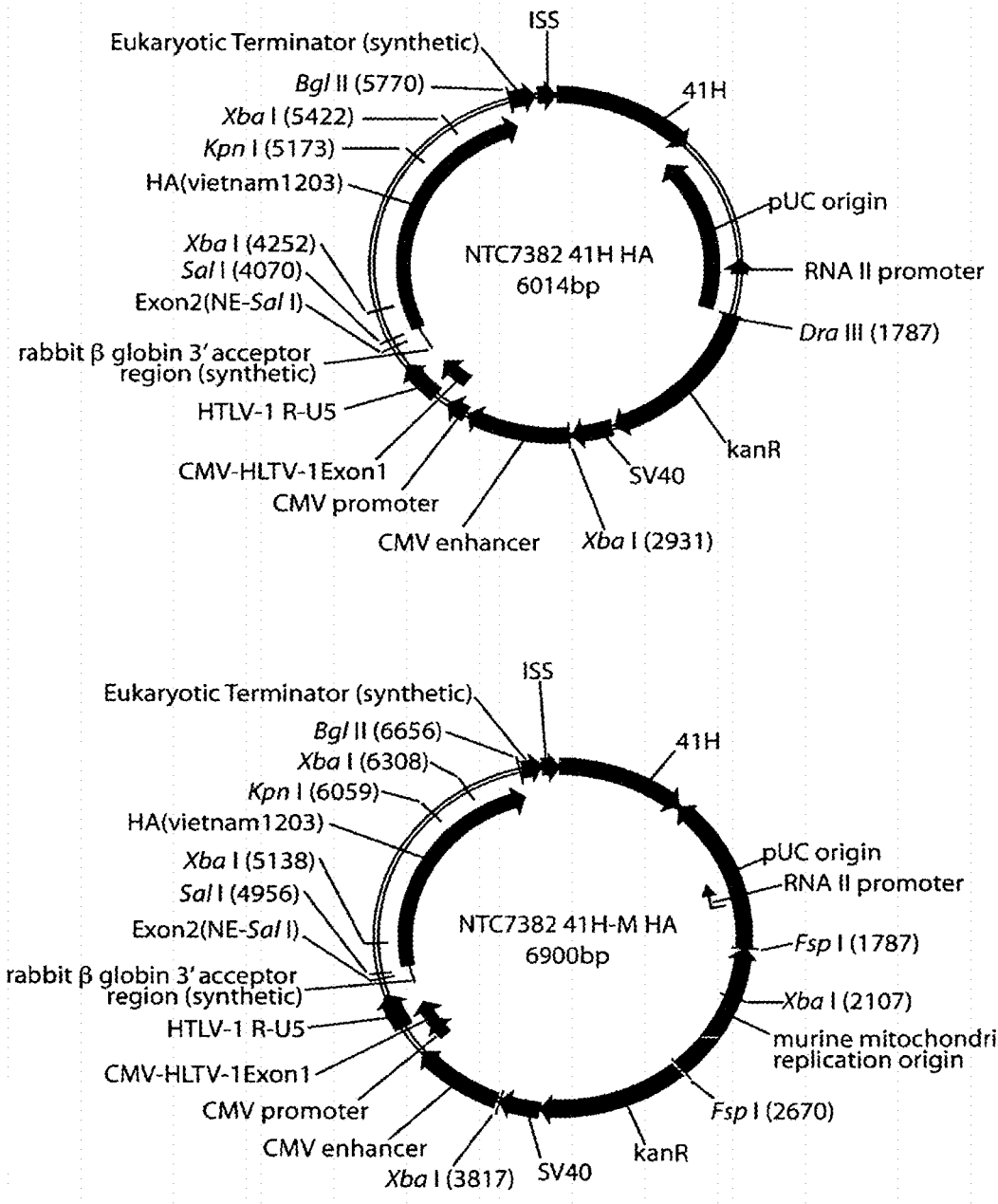

In FIG. 23, annotated maps of the NTC7382 41H-HA and NTC7382-41H-M-HA plasmids are shown.

Definitions

ADAR: Adenosine deaminase acting on RNA (RNA binding protein which edits RNA content from A to I).

Ad5: Adenovirus serotype 5.

adjuvant: Includes nucleic acid adjuvants (e.g. immunostimulatory eRNA, immunostimulatory CpG DNA, expression vectors producing cytokines, chemokines, etc) or other molecules such as cell death promoters (e.g. herpes thymidine kinase) and chemical adjuvants which are compounds that can enhance, prolong or otherwise modulate antigen-specific immune responses when administered with a vaccine antigen.

APC: Antigen Processing Cell, for example, langerhans cells, plasmacytoid or conventional dendritic cells.

BAC: Bacterial artificial chromosome.

ccc: Covalently Closed Circular.

costimulatory molecules: Costimulatory plasmids (e.g. IL12) or molecules, cell death inhibitors (e.g. antiapoptotic proteins) or enhancers as know in the art and included herein by reference.

cmv: Cytomegalovirus.

CTL: Cytotoxic T lymphocyte.

delivery methods: Methods to deliver gene vectors [e.g. poly(lactide-co-glycolide) (PLGA), ISCOMs, liposomes, niosomes, virosomes, chitosan, and other biodegradable polymers, electroporation, sonoporation, ultrasound, gene gun, microneedles, naked DNA injection, hydrodynamic delivery, high pressure tail vein injection, needle free biojector, liposomes, microparticles, microspheres, nanoparticles, virosomes, bacterial ghosts, bacteria, attenuated bacteria, etc] as know in the art and included herein by reference.

DNA replicon: Plasmids, cosmids, bacterial artificial chromosomes (BACs), bacteriophages, viral vectors and hybrids thereof.

dsRNA: Double stranded RNA.

E. coli: Escherichia coli, a gram negative bacteria.

ECFP: Enhanced green fluorescent protein.

eRNA: RNA element. A DNA sequence containing an expressed RNA. The eRNA promoter may be a Pol I, Pol II or Pol III promoter, and the expressed RNA may be a single stranded RNA, double stranded RNA, hairpin RNA, microRNA, RNA aptamer or a ribozyme.

HA: Hemagglutinin.

hdsRNA: Hairpin double stranded RNA.

Hr(s): Hour(s).

Kd: Kilodalton.

immune response: Antigen reactive cellular (e.g. antigen reactive T cells) or antibody (e.g. antigen reactive IgG) responses.

immunostimulatory RNA element: immunostimulatory eRNA. A DNA sequence encoding an expressed RNA that stimulates innate (e.g. type 1 interferon) or adaptive (e.g. antigen specific T- or B-cell response) immune responses through activation of cellular receptors including RIG-I, MDA5, PKR, OAS, TLR3, TLR7, TLR8, NALP3, etc. For example, RIG-I/MDA5 activating eRNA41H, eRNA41J, eRNA11a, VARNAI, VARNAI/II etc.

intracellular targeting: Directing a target antigen to either an inter or intracellular destination, or the antigen presentation pathway, using a targeting sequence.

IRF-3: Interferon Regulatory Factor 3.

IS10: Insertion sequence 10

MDA5: MDA-5, Melanoma differentiation-associated gene 5, a helicase containing cytoplasmic dsRNA receptor.

min: Minute.

NTC7382 promoter: A chimeric promoter comprising the CMV enhancer-CMV promoter-HTLV R-U5-synthetic rabbit β globin 3' intron acceptor-exon 2-SRF protein binding site-kozak sequence, with or without an upstream SV40 enhancer.

NTC7382-41H-M: or NTC7382-41H-M-HA. This is the NTC7382 backbone, containing the eRNA41H RNA element (41H), with (HA) or without the H5 HA antigen. M refers to insertion of a 1 kb noncoding region (the mitochondrial R-region) which contains the mitochondrial bidirectional promoter for the synthesis of polycistronic RNA for the heavy and light strands as well as the replication origin for the heavy chain.

NTC-HA: NTC7382-HA, NTC8382-HA, NTC1-HA, NTC2-HA RNA-out-HA vectors, with or without eRNA. Collectively, these are DNA vaccine vectors encoding the influenza H5 HA 'bird flu' DNA vaccine vectors that contain a synthetic HA gene maintaining the influenza H5N1 'bird flu' A/Vietnam/1203/04 amino acid sequence. For safety (i.e. gene transfer during immunization to infecting non pathogenic virus) the HA gene was human codon-optimized to reduce genome homology. As well, the multiple basic amino acid motifs at the HA cleavage site correlative with pathogenicity was replaced with the corresponding region from several nonpathogenic influenza strains.

OAS: 2'5' oligoadenylate synthetase (RNA binding protein that activates RNase L).

PCR: Polymerase Chain Reaction.

pDNA: Plasmid DNA.

PKR: Interferon-induced double-stranded RNA-dependent protein kinase, a cytoplasmic dsRNA receptor.

pm91: A VARNAI derivative (PKR5), in which VARNAI has a 1 bp change (pm91) in the central domain (Rahman A, Malhotra P, Shar R, Kewalramani T, Thimmapaya B 1995 *J Virology* 69: 4299-4307) that is inactive for PKR inhibition, but (as disclosed herein) retains MDA5 activation.

plasmid: Plasmids, cosmids, bacterial artificial chromosomes (BACs), bacteriophages, viral vectors and hybrids thereof.

pol III: RNA polymerase III

5'-PPP: 5'-triphosphate that is present on viral transcripts and some DNA polymerase III transcripts. 5'-PPP RNA is a known activator of RIG-I.

pUC origin: pBR322-derived origin, with G to A transition that increases copy number at elevated temperature.

RIG-I: Retinoic acid inducible gene I, a cytoplasmic helicase containing RNA receptor. hRIG-I=human and mRIG-I=murine. DeNy=Dominant Negative hRIG-I.

RNA element: eRNA, an expression cassette containing an expressed RNA sequence. The promoter may be a Pol I, Pol II or Pol III promoter, and the expressed RNA may be a single stranded RNA, double stranded RNA, hairpin RNA, microRNA, RNA aptamer or a ribozyme.

RNA-OUT: Insertion sequence 10 (IS10) encoded RNA-OUT, an antisense RNA that hybridizes to, and reduces translation of, the transposon gene expressed downstream of RNA-IN. An RNA-OUT vector selectable marker DNA fragment that is compatible with DraIII and KpnI is disclosed herein.

R T-PCR: Real time PCR.

sacB: Structural gene encoding *Bacillus subtilis* levansucrase. Expression of sacB in gram negative bacteria is toxic in the presence of sucrose SEAP: Secreted alkaline phosphatase.

shRNA: Short hairpin RNA.

siRNA: Short inhibitory RNA.

ssRNA: Single stranded RNA:

target antigen: Immunogenic protein or peptide epitope, or combination of proteins and epitopes, against which a immune response can be mounted. Target antigens may by derived from a pathogen for infectious disease applications, or derived from a host organism for applications such as cancer, allergy, or autoimmune diseases. Target antigens are well defined in the art. Some examples are disclosed in Williams, Supra, 2006 and are included herein by reference.

T E buffer: A solution containing approximately 10 mM Tris pH 8 and 1 mM EDTA.

$T_H1$: T helper 1.

$T_H2$: T helper 2.

TLR: Toll-Like Receptor.

VARNA: Adenoviral virus associated RNA, including VARNAI (VAI or VA1) and or VARNAII (VAII or VA2) from any Adenovirus serotype, for example, serotype 2, serotype 5 or hybrids thereof.

VARNAI: Adenoviral virus associated RNAI, also referred to as VAI, or VA1, from any Adenovirus serotype, for example, serotype 2, serotype 5 or hybrids thereof.

vector: A gene delivery vehicle, including viral (e.g. alphavirus, poxvirus, lentivirus, retrovirus, adenovirus, adenovirus related virus, etc) and nonviral (e.g. plasmid, midge, transcriptionally active PCR fragment, minicircles, bacteriophage, etc) vectors. These are well known in the art and are included herein by reference.

The invention relates to compositions and methods for gene therapy, genetic immunization or interferon therapy. The invention is practiced in the expression of gene products in eukaryotic cells, for the purpose of gene therapy, genetic immunization or interferon therapy. The invention applies to such use of ccc recombinant DNA molecules such as plasmids, cosmids, BACs, bacteriophages, viral vectors and hybrids thereof (herein collectively referred to as plasmids).

Gene therapy or DNA vaccine plasmids described in the art are not optimal with suboptimal expression, antibiotic selection, additional nonessential DNA, nor do they strongly activate innate immune responses. These deficiencies are critical, since several incremental improvements in the vectors could result in large differences in expression levels, quality of immune responses and ultimately protective immunity.

Expression Vector Preferred Embodiments

In a preferred embodiment, a pDNAVACCUltra vector is used to express a gene product in an organism for therapy or vaccination. By way of example, an influenza H5 hemagglutinin (HA) pDNAVACCUltra vector (NTC8382) with an immunostimulatory RNA element (41H) is shown in FIG. 1. Kanamycin resistance marker-containing pDNAVACCUltra vectors have been disclosed in Williams, Supra, 2006 and are included herein by reference. The prokaryotic replication origin is protected by a downstream prokaryotic transcriptional terminator to improve stability and yield with a broad range of target genes. Unique restriction sites flank the prokaryotic modules, to allow easy modifications. All plasmid elements have been optimized and minimized to comply with current WHO and FDA guidelines regarding content and elimination of extraneous materials. The resulting vector backbone is much smaller than existing vectors such as VR1012 (5 kb, versus 3-3.5 kb for the pDNAVACC vectors, or 2.8 kb for the NTC8382 backbone (disclosed herein), consisting of replication origin-RNA selectable marker-SV40 enhancer-NTC7382 chimeric CMV promoter), and yet it drives higher levels of expression.

In another preferred embodiment, the pDNAVACCUltra vector used to express a gene product for therapy or vaccination contains a selectable RNA marker (FIG. 1) rather than an antibiotic gene. This further reduces the vector size and complies with regulatory agencies guidance to eliminate antibiotic resistance markers from therapeutic and vaccine vectors. In another preferred embodiment for therapy or vaccination, the RNA based selectable marker of the invention is incorporated into other DNA vaccine or therapeutic plasmid backbones, a non limiting list includes VR1012, pVAX1, pVC0396, pCMVkm2, pITR, pCOR, pPJV7563, pWG4303 and derivatives.

In another preferred embodiment for therapy or vaccination, a pDNAVACCUltra vector incorporating a chimeric promoter is utilized. Preferred chimeric promoters are CMV or SV40-CMV promoters wherein the SV40 enhancer is fused upstream of the CMV promoter as disclosed in Williams, Supra, 2006. The CMV or SV40-CMV promoter may be linked downstream to a leader sequence and the antigen gene, or preferably, a leader sequence containing an intron, and then the antigen gene. Preferably, the leader sequence containing an intron is the native CMV exon1-intron 1, or a synthetic intron such as is disclosed in Williams, Supra, 2006, or the HTLV-I R-U5 sequence (CMV/R) as disclosed by Barouch et al, Supra, 2005, or the HTLV R-U5-synthetic rabbit β globin 3' intron acceptor-SR protein binding site (NTC7382 promoter) disclosed herein. In a preferred embodiment, the pDNAVACCUltra vector used to express a gene product for therapy or vaccination contains the NTC7382 promoter (FIG. 1) rather than a standard CMV promoter, to increase expression of the gene product. Optionally, the NTC7382 promoter further comprises an upstream SV40 enhancer. In another preferred embodiment for therapy or vaccination, the NTC7382 promoter of the invention is incorporated into other DNA vaccine or therapeutic plasmid backbones. A non-limiting list includes: VR1012, pVAX1, pVC0396, pCMVkm2, pITR, pCOR, pPJV7563, pWG4303 and derivatives. In another preferred embodiment for therapy or vaccination, the NTC7382 promoter of the invention is incorporated into viral (e.g. alphavirus, poxvirus, lentivirus, retrovirus, adenovirus, adenovirus related virus, etc) or nonviral (e.g. plasmid, midge, transcriptionally active PCR fragment, minicircles, bacteriophage, etc) vectors.

Immunostimulatory RNA Element Preferred Embodiments

In a preferred embodiment, immunization is performed using a viral vector containing one or more immunostimulatory RNA elements of the invention. In a preferred embodiment, the viral vector is an alphavirus, poxvirus, lentivirus, retrovirus, adenovirus or adenovirus related virus. In another preferred embodiment, immunization is performed using a nonviral vector or DNA fragment containing one or more immunostimulatory RNA elements of the invention. In yet another preferred embodiment, immunization is performed using a pDNAVACCUltra vector containing one or more immunostimulatory RNA elements of the invention. The immunostimulatory RNA element embodiments of the invention are incorporated into the backbone of the vector or DNA fragment. In another preferred embodiment, the immunostimulatory RNA sequences activate innate immune responses (FIG. 2). In another preferred embodiment, the immunostimulatory RNA sequences activate innate immune responses through cytoplasmic RNA receptors RIG-I and/or MDA5 (FIG. 3) or the inflammasome. In another preferred embodiment, the immunostimulatory RNA sequences activate innate immune responses through endosomal RNA receptors TLR3, TLR7 or TLR8 in the transfected cells. In another preferred embodiment, the immunostimulatory RNA sequences activate innate immune responses through endosomal RNA receptors TLR3, TLR7 or TLR8 in non transfected cells after apoptosis, necropsy, or phagocytosis of the transfected cell. In yet another preferred embodiment, the immunostimulatory RNA sequences activate adaptive immune responses against the vector-expressed target antigen. In yet another preferred embodiment, the target antigen is targeted to either an inter- or intra-cellular destination, or the antigen presentation pathway, using a targeting sequence. A non-limiting list of targeting sequences is disclosed in Williams, Supra, 2006, and included herein by reference. In another preferred embodiment, the immunostimulatory RNA sequences act to improve expression of the gene of interest from the plasmid. The RNA element containing nonviral vector or DNA fragments will not induce adaptive immune responses against the vector backbone (i.e. reusable vectors unaffected by prior immune exposure). This is a significant advantage over alternative vectors such as alphaviral replicon or adenoviral vectors.

In yet another preferred embodiment, non-viral or viral vectors or DNA fragments containing immunostimulatory RNA sequences are used to increase anti-viral, anti-tumor and or antibacterial activity in a vertebrate, or cells of a vertebrate. In yet another preferred embodiment, the immunostimulatory RNA sequences increase anti-viral, anti-tumor and or antibacterial activity in a vertebrate, or cells of a vertebrate through induction of type 1 interferon production. In yet another preferred embodiment, vectors or DNA fragments containing immunostimulatory RNA sequences are used in treatment to induce production of natural type 1 interferon's in the cells of an individual to whom the administration of type 1 interferon's would be beneficial. The immunostimulatory RNA may be delivered to a cell in a DNA fragment or vector with or without a co-delivered antigen gene. The immunostimulatory RNA may be delivered to cells via a plurality of vectors, a non limiting list including a PCR fragment, a Midge vector, a non-viral vector, or a viral vector.

Vector Delivery Preferred Embodiments

The vector embodiments of the invention may be delivered to a cell either in vivo, in vitro or ex vivo, utilizing one or more of the plurality of delivery methods known in the art. A non limiting list of delivery methods includes: naked DNA or formulated DNA, needle or needle free delivery, delivery enhancement by electroporation, sonoporation, ultrasound, hydrodynamic, lipofection, cationic polymers, gene gun, nanoparticles, microparticles, cationic lipids, or microneedles. For delivery to an organism, delivery may be by oral, buccal, nasal, inhalation, topical, vaginal, rectal, intravenous, intramuscular, intradermal, epidermal, systemic, or by other routes of administration known in the art.

EXAMPLES

The methods and compositions of the invention are further illustrated in the following examples. These are provided by way of illustration and are not intended in any way to limit the scope of the invention.

Example 1: Development of Immunostimulatory RNA Element Plasmids

Cytoplasmic dsRNA can directly induce dsRNA receptors ADAR, PKR, 2'-5' oligoadenylate synthetase (OAS), retinoic acid inducible gene I (RIG-I) and melanoma differentiation-associated gene 5 (MDA5). Activation of RIG-I and MDA5 (herein referred to as RIG-I pathway) leads to interferon and inflammatory cytokine (e.g. TNFα) production while PKR activation inhibits protein synthesis thus reducing antigen production (reviewed in Wang and Carmichael, Supra, 2004).

PKR contains two dsRNA binding domains (both of which must be occupied for activation) and recognizes primarily long (>30 bp) dsRNAs. PKR activation is inhibited by a variety of structured viral RNAs, such as adenovirus virus-associated RNAI (herein referred to as VARNAI, VAI or VA1).

RIG-I and MDA5 each contain a single dsRNA binding domain. MDA5 recognizes RNA from positive sense ssRNA Picornavirus (EMCV) and poly(I:C) (Kato, H, Takeuchi O, Sato S, Yoneyama M, Yamamoto M, Matsui K, et al. 2006. *Nature* 441: 101-105; Gitlin L, Barchet W, Gilfillan S, Cella M, Beutler B, Flavell R A, Diamond M S, Colonna M. 2006. *Proc. Natl. Acad. Sci.* 103: 8459-8464), while RIG-I recognizes RNA from positive sense ssRNA flavivirus (Japanese encephalitis virus, dengue, hepatitis) and negative sense RNA virus Orthomyxoviridae (Influenza) Rhabdovirus (Vesicular stomatitis virus) and paramyxoviruses (Sendai virus, Newcastle disease) (Chang T H, Liao C L, Lin Y L. 2006. *Microb Infect* 8: 157-171; Melchjorsen J, Jensen S B, Malmgaard L, Rasmussen S B, Weber F, Bowie A G, Matikainen S, Paludan S R. 2005. *J. Virol.* 79: 12944-12951; Sumpter R Jr, Loo Y M, Foy E, Li K, Yoneyama M, Fujita T, Lemon S M, Gale M Jr. 2005. *J. Virol.* 79: 2689-2699) and siRNA (Marques J T, Devosse T, Wang D, Zamanian-Daryoush M, Serbinowski P, Hartmann R, Fujita T, Behlke M A, Williams B R. 2006. *Nature Biotechnol.* 24: 559-565). The structural basis for MDA5 recognition is unknown, but dsRNA (short siRNA, and long dsRNA that arise during viral replication) and specific structured RNAs such as the hepatitis C virus (HCV) internal ribosome entry site (IRES) have been identified as RIG-I activators (Sumpter et al, Supra, 2005; Marques et al, Supra, 2006). The optimal ligands are unknown. For example, Marques et al, Supra, 2006 teach that siRNAs ranging from 21 to 27 nucleotides in length activated the interferon system when they lacked 2-nucleotide 3' overhangs, a characteristic of Dicer products. The recognition of these blunt siRNAs was mediated by RIG-I and they speculated that the presence of 3' overhangs impaired RIG-I ability to unwind the dsRNA substrate and activate downstream signaling to the transcription factor IRF-3. They speculated that the requirement for blunt ends may prevent recognition of endogenous self RNAs, such as dicer cleavage products. However, this result is contradicted by Hornung V. Ellegast J, Kim S, Brzozka K, Jung A, Kato H et al, 2006 *Science* 314: 994-997, who demonstrated that blunt ends are not required for RIG-I activation. One basis for discriminating endogenous self RNA is that a 5'-triphosphate (5'-PPP) group increases RIG-I activation (Pichlmair A, Schulz O, Tan C P, Naslund T I, Liljestrom P, Weber F, Sousa C. 2006. *Science* 314:997-1001; Hornung et al, Supra, 2006). Such 5'-triphosphates are generally removed from, or masked on, self RNA species; this is a structural basis for the distinction between self and non-self RNA (Reviewed in Bowie A G, Fitzgerald K A, 2007 *Trends Immunol* 28: 147-150). Indeed, one identified RIG-I ligand is the cytosolic 5'-PPP containing viral leader transcript of measles virus; the 5'-PPP is required for activation but not RIG-I binding (Plumet S, Herschke F, Bourhis J M, Valentin H, Longhi S, Gerlier D. 2007. *PLoS* 2:e279).

In summary, the prior art teaches that to activate RIG-I an RNA must be localized in the cytoplasm. The RNA may be double stranded RNA or may be structured single stranded RNA and activation is stronger if the RNA contains a 5'-triphosphate. The optimal length, degree of secondary structure, and end structure is unknown.

Production of RIG-I or MDA5 activating RNA's from a plasmid vector presents some special problems. The viral RNAs that RIG-I detects are generally produced in the cytoplasm using viral RNA polymerases that do not remove the 5' triphosphate. As well, proteins bound to the 5'-PPP may mask the RNA from RIG-I detection (such as with endogenous 5S ribosomal RNA which is ribosome associated after nucleosome assembly). Careful design is needed to obtain 5'-PPP cytoplasmic RNAs using the endogenous nuclear transcription and nuclear export capacities of a cell needed for expression from a DNA vaccine plasmid. First, to obtain a 5'-PPP on a nuclear produced RNA, an appropriate promoter must be utilized such that the 5'-PPP is not removed by capping (mRNA) or processing (e.g. tRNA, rRNA). The RNA must then be exported from the nucleus to the cytoplasm since plasmid transcription will occur in the nucleus while the RIG-I receptor is in the cytoplasm. As well, the 5'-PPP containing cytoplasmic RNA must then act as a ligand and activator of RIG-I. Plumet et al, Supra, 2007 failed to activate RIG-I using a plasmid vector in which the pol III H1 promoter was used to express a known RIG-I activator, measles viral leader. RIG-I activation was obtained using plasmid driven expression of 10 copies of a native Epstein Barr virus small RNA (EBER1), another known RIG-I ligand (Samanta M, lwakira D, Kanda T, Imaizumi T, Takada K. 2006. *EMBO J.* 25: 2407). However, 10 copies of a repetitive sequence is not acceptable for plasmid propagation in *E. coli*.

Promoters:

Preferable, immunostimulatory RNA is expressed from RNA polymerase III (pol III) promoters. These promoters are small, express to levels up to 10 fold higher than pol II promoters, do not interfere with pol II directed antigen expression (See Williams, Supra, 2006) and have the potential to retain 5'-triphosphates. The murine U6, human H1, and adenoviral VAI pol III promoters all have been used to express short RNAs. Adenoviral VAI has been experimentally verified to retain the 5' triphosphate. The U6 small nuclear RNA (snRNA) expressed from the U6 promoter contains a gamma-monomethyl phosphate which is distinct from other RNA caps (Singh R, Reddy R 1989 *Proc. Nat. Acad. Sci. USA* 86:8280-8283). Capping of this RNA is dependent on downstream RNA sequences (Singh R, Gupta S, Reddy R. 1990 *Mol. Cell Biol.* 10: 939-946). The art teaches that tRNA promoters, such as tRNAVal promoters will generally produce cytoplasmic RNAs lacking 5'-PPP, since normal processing of tRNAs in the nucleus removes the 5' triphosphate. DNA polymerase II promoters will also generally produce cytoplasmic RNAs lacking 5'-PPP, since 5'-PPP on mRNA is removed during capping prior to nuclear export. DNA polymerase I promoters will, likewise, not produce unmodified cytoplasmic RNA, since rRNA is heavily processed and modified in the nucleolus prior to nuclear export.

Use of DNA polymerase III promoters restricts the ligands that can be expressed, since transcription is terminated at runs of 4 or more T residues in the gene, and only short RNAs (generally <300 bp) can be made.

Nuclear Export:

To be immunostimulatory, the RNA must be exported from the nucleus to the cytoplasm (RIG-I and MDA5 proteins are cytoplasmic). Export of Pol III transcripts can be mediated by exportin-t (tRNAs) or exportin-5 (mini helix containing RNAs such as shRNA and VA1) (reviewed in Rodriguez M S, Dargemont C, Stutz F. 2004. *Biol Cell* 96: 639-655). In the case of minihelix, RNA, such as the HCV IRES RIG-I ligand could be inserted within the VAI transcript, in a manner that preserves the minihelix configuration. Fusions to the C terminus of tRNAVal (maintaining tRNA folding, and using the linker defined in Kuwabara T, Warashina M, Koseki S, Sano M, Ohkawa J, Nakayama K, Taira K. 2001. *Nuc. Acids Res.* 29: 2780-2788) have been utilized extensively to export tRNAVa1-Ribozyme fusions to the cytoplasm. The art teaches that tRNAs are 5' processed, and that this processing is required for nuclear export. Thus the art teaches that tRNAs are not suitable for export of a RIG-I activating 5'-PPP immunostimulatory RNA. In contrast, a tRNA-ribozyme fusion of Kuwabara et al, Supra, 2001 was reported to have been exported to the cytoplasm without 5'-end removal, contrary to the prevailing view of tRNA export. However, since the 5'-end modifications were not characterized, it is unknown if these constructs have a 5'-PPP. Thus, it is possible, but not taught in the art, that a tRNA-Val-linker or tRNA-Val-linker-RNA may be utilized as a RIG-I ligand.

Nuclear Export of Long dsRNA:

Long annealed dsRNA is not exported from the nucleus. Mammalian genomes contain many natural sense-antisense transcripts that have the potential to produce dsRNA Long nuclear dsRNA is a substrate for ADAR. Export of the resultant extensively Adenosine to Inosine edited RNA from the nucleus is inhibited (e.g. by binding to p54nrb; reviewed in Wang and Carmichael, Supra, 2004). Thus, the art teaches that long dsRNA (>30 bp) expressed in the nucleus will be edited by ADAR, and subsequently will not be exported to the cytoplasm. Consistent with this, a plasmid vector containing a long dsRNA (250 bp) expressed by convergent transcription of U6 and H1 promoters did not activate PKR or the interferon response after transfection and expression of the dsRNA (Strat A, Gao L, Utsuki T, Cheng B, Nuthalapaty S, Mathis J M, Odaka Y, Giordano T. 2006. *Nucl. Acid Res.* 34:3803-3810).

RIG-I Ligands:

Several RIG-I ligands have been described in the art and several DNA vaccine RNA element compositions containing them are disclosed and tested herein. These include:

1) and 2) Two Hepatitis C Virus RIG-I ligands: the structured HCV 5'-IRES and 3'-non translated regions Both of these RNAs have been demonstrated to activate RIG-I (Sumpter et al, Supra, 2005; Saito T, Hirai R, Loo Y M, Owen D, Johnson C L, Sinha S C, Akira S, Fujita T, Gale, M. 2007. *Proc. Natl. Acad. Sci.* 104: 582-587). The HCV IRES is also an inhibitor of PKR (Vyas J, Elia A, Clemens M J. 2003 *RNA* 9: 858-870).

3) a 100 bp dsRNA region of the influenza genome. The influenza virus dsRNA is based on A/P R/8/34-H1N1 (PR8) and is a modification (to remove potential Pol III termination sequences) of the first 100 bp fragment of gene segment 3 (Lamb R A, Choppin P W. 1983. *Annu Rev Biochem* 52: 467-506); this sequence was selected since this segment has potent in vivo stimulatory activity similar to natural influenza virus infection (Fang J, Bredow S, Taishi P, Majde J A, Krueger J M. 1999. *J Med Virol* 57: 198-203). While not taught in the art, the inventor speculated that this RNA might be a ligand of RIG-I, since RIG-I activates interferon is production in influenza A virus infected cells (Opitz B, Rejaibi A, Dauber B, Eckhard J, Vinzing M, Schmeck B, Hippenstiel S, Suttorp N, Wolff T. 2007. *Cell Microbiol.* 9: 930-938) and this RNA may normally be made with a 5'-PPP since it is at the 5'-end of the genome.

DNA vaccine vectors containing expressed hairpin double stranded (hdsRNA) sequences similar to those described in Marques et al, Supra, 2006 have been disclosed (Williams, Supra, 2006) and are included herein by reference. In brief, the pDNAVACCUltra vaccine vectors were modified to encode pol III promoter cassettes that can be used to clone a target RNA (eRNA cassette) to produce RNA upon cell transfection. DNA vaccines containing U6 promoter-driven hdsRNAs were tested in vitro (lipofectamine 2000 transfection into RAW 264.3 mouse macrophage cell line) for induction of TNFα secretion. Several inducers that dramatically improved the immunostimulatory activity of the vector, without activating PKR mediated translation inhibition, were identified (Williams, Supra, 2006). These DNA vaccine plasmids containing RNA elements that produce immunostimulatory RNA (Williams, Supra, 2006) can potentially signal through TLR3 (dsRNA), TLR8/9 (ssRNA) or activate cytoplasmic RNA receptors RIG-I or MDA5, PKR, ADAR, or OAS induced RNaseL pathway, or nuclear ADAR.

Multiple classes of immunostimulatory RNA elements exist, depending on the subset of RNA receptors that are activated. Consider, by way of example, the case of RNA elements that either activate, or don't activate, PKR. PKR activation, such as occurs with long dsRNA produced by alphaviral amplicon vectors, leads to shutdown of protein translation and reduced antigen expression. Therefore, one novel class of composite RNA elements would not activate PKR. One composition to accomplish this would be to include a PKR inhibitor RNA along with an immunostimulatory RNA, to maximize immunostimulation without loss of antigen expression (Williams, Supra, 2006).

RNA-based inhibitors of PKR are described in the art. One well characterized example is the adenoviral encoded RNAI (called VAI, VA1, or VARNAI) or RNAII. VARNAI is a potent inhibitor of PKR, a weak inhibitor of ADAR, and a weak activator of OAS ($\frac{1}{10}$ as strong as dsRNA; Desai S Y, Patel R C, Sen G C, Malhotra P, Ghadge G D, Thimmapaya B. 1995. *J Biol. Chem* 270: 3454-3461).

With the goal of ultimately developing combination RNA elements that activate RIG-I and MDA5 but not PKR, a series of RNA element vectors were constructed, incorporating the design considerations outlined above. The Mfold program of Zuker, M. 2003. *Nucleic Acids Res.* 31:3406-15 was utilized to verify all constructs retained required folding structures (e.g. all tRNA fusions did not interfere with the tRNA structure, or all VARNAI or other minihelix constructs were predicted to retain the terminal minihelix).

All cloning was initially into the pDNAVACCUltra5 EGFP or pDNAVACCUltra5 EGFP MU6 (StuI) DNA vaccine vectors using either standard restriction enzyme cloning, or AarI based type IIS cloning. These vectors and cloning methodologies are disclosed in Williams, Supra, 2006 and are included herein by reference. All clones were sequence verified. All primers were purchased from MWG Biotech (Huntsville Ala.) or Integrated DNA Technologies (Coralville, Iowa). Vector construction details are as follows:

VARNA Based Clones:

pDNAVACCUltra5 EGFP vectors that contained the VARNAI gene, or both the VARNAI and VARNAII genes, in either orientation, were constructed. The VARNA genes (including the pol III terminator and upstream sequences) were PCR amplified from Adenovirus serotype 5 genomic DNA, and cloned into the blunt StuI site of the parent vector (a permissive site between the prokaryotic replication origin and the eukaryotic pol II terminator). The resultant constructs (single or double inserts, in both orientations) were sequence verified. VARNAIA is transcribed clockwise relative to the pDNAVACCUltra vector (FIG. 1) and comprises sequences 10,597-10,790 of the Ad5 genome (Genbank accession number X02996). The VAI+VAII clone comprises sequences 10,589-11,049 of the Ad5 genome.

eRNA7: VARNAI-S35

V A RNAI is a internally Pol III driven highly structured RNA that inhibits the translation blocking activity of PKR. The VARNAIA clone was modified to a stable hairpin structure replacing the central domain (critical for PKR inhibition) with an acceptor hairpin structure. As well the 3' end was modified to be blunt. The final clone was the same sequence as the VA1-S35 chimera disclosed in Thompson J D 2005 U.S. Pat. No. 6,852,535.

eRNA10: eRNA7, with HCV IRES Inserted (VARNAI-S35+HCV IRES)

The cellular RIG-I dsRNA sensor is activated by structured viral RNAs, such as the HCV IRES. This 200 bp IRES does not contain runs of four or more T's so it can be made by RNA polymerase III. The HCV IRES (Sumpter et al, Supra, 2005) was PCR amplified (from plasmid pLCSR2HCV), and cloned into the VARNAI S35 AcII site (as an internal fusion with the ERNA7 VARNAI-S35 RNA).

eRNA23: eRNA7: (VAI Minihelix)

eRNA24: eRNA10, (VAI Minihelix)

The S35 constructs (eRNAs 7 and 10) do not have an extended 3' end on the terminal stem, due to deletion of a CTCC sequence from VA1. This may affect nuclear export. The CTCC sequence was reintroduced into the S35-based constructs eRNA7 and eRNA10, As well, the terminator was extended from the minimal 4T to 6T. The 3' end of VA1 is shown below, with the 6 bp insert in eRNA23 and 24 double underlined. The 4 TTTT terminator in eRNA7 and 10 is after the 6 bp insert.

(SEQ ID NO: 1)
eRNAs 23 and 24: GACAACGGGGAGTG<u>CTCCTT</u>TTTTGGCTTCCT eRNA31B-C: VARNAIA-shRNA Constructs pDNAVACCUltra VARNAI was modified to express shRNA structures from the 3' end. Such constructs were made to contain a Lamin shRNA (31C) exactly as described in Pebernard S, Iggo R D. 2004. *Differentiation* 72: 103-111, or the RNA9.2 shRNAs (31C; Williams, Supra, 2006).

eRNA42: VARNAIAext

Here, 50 bp of additional upstream 5' sequences from adenovirus serotype 5 (bases 10,544-10,596 of the Ad5 genome added to existing 10,597-10,790 to create 10,544-17,790 in final clone) were added to the VARNAI gene, to determine if additional 5' flanking sequences improves activity.

eRNA43: VARNAIAext HCV 3' NTR

Here the HCV 3' NTR (a known RIG-I ligand; Saito et al, Supra, 2007) was cloned into the BstEII site of VARNAIA in eRNA42.

eRNA44: VARNAIAext-Minihelix

This is eRNA42 with an internal deletion (from after the promoter B box, to the beginning of the terminal minihelix within the VARNAI gene; Ad5 sequences by 10,696-10,740 deleted) that was predicted by Mfold to form a smaller stable minihelix, with less stable secondary structure than the native VARNAI gene.

U6 and H1 Promoter Based Clones:

A clone (INF dsRNA) containing a modified 100 bp fragment DNA of influenza (defined above; Lamb and Choppin, Supra, 1983) as a 100 bp hairpin was designed using synthetic oligonucleotides and cloned into HpaI/NheI digested pDNAVACCUltra5 MU6 (StuI) DNA vaccine vector (Williams, Supra, 2006). The presence of a 100 bp hairpin was toxic to *E. coli* and the fragment was uncloneable. The clone was redesigned to eliminate the hairpin, and to instead have a single insert transcribed by H1 and U6 from opposite sides. This creates a dsRNA, without need for a large, detrimental hairpin or repeat structure in the vector. H1-mU6 (StuI) INF dsRNA: Contained a 60 bp Fragment of Influenza DNA.

H1-mU6 (StuI) INF dsRNA Repaired: This was repaired using oligonucleotides to contain the full 108 bp influenza fragment (FIG. 4). Pol III terminators (TTTTTT) are inserted before and after the 100 bp dsRNA such that transcription ends after the dsRNA insert.

U6 and tRNAVal Promoter Based Clones:

eRNA11: tRNAVal MU6 INF dsRNA (dsRNA Contains Recessed U6 Start 5' End, U6 A Start) The pDNAVACCUltra5 EGFP H1 INF dsRNA U6 (repaired) construct was modified using PCR to remove the H1 promoter, and replace it with the human tRNAVal and linker (using synthetic nucleotides). The human tRNAVal and linker sequence is as described (Kuwabara et al, Supra, 2001). The configurations of the insert and the sequences of the predicted annealed dsRNA for eRNA11 ((SEQ ID NO: 2), eRNA11A (SEQ ID NO: 3) and eRNA11B (SEQ ID NO: 4) are shown in FIG. 4.

eRNA11A: tRNAVal MU6 INF dsRNA (dsRNA contains blunt U6 start 5' end, U6 A start). The 3 bp insert in eRNA11 used to create eRNA11a is bolded and underlined in FIG. 4.

eRNA11B: tRNAVal MU6 INF dsRNA (dsRNA contains recessed 5' end, U6 G start) The 6 bp insert modification from eRNA11 is bolded and underlined in FIG. 4.

eRNA11C: eRNA11B tRNA-HCV 3' NTR-U6

The 100 bp influenza sequence in eRNA11B was replaced with a 90 bp fragment of the highly structured HCV 3' NTR sequence (a known RIG-I ligand).

eRNA11D: eRNA11 tRNA-INF ssDNA

Here the base eRNA11 vector was modified to produce an ssRNA from the tRNA promoter only (by deletion of the downstream U6 promoter), to determine the contribution of dsRNA, if any, to interferon β induction.

eRNA12: tRNAVal-HCV IRES

The dsRNA and U6 region were deleted and replaced with the HCV IRES.

eRNA18: U6 INF ssRNA

The tRNA gene from pDNAVACCUltra EGFP eRNA11 (tRNAVal MU6 INF dsRNA) was deleted to determine the contribution of dsRNA, and tRNA mediated nuclear export, if any, to interferon β induction.

H1 Promoter Based Clones:

eRNA17: H1 INF ssRNA CTE

Here the MU6 promoter was deleted from H1 INF dsRNA U6 repair, and replaced with the constitutive transport element (CTE) sequence. This will make a single strand, and in combination with eRNA18, a double stranded RNA, with a CTE sequence on a single strand. CTE is a TAP/NXF1 binding export hairpin structure that exports unspliced RNAs derived from simian type D retroviruses. (Smulevitch S, Bear J, Alicea C, Rosati M, Jalah R, Zolotukhin A S, et al, 2006 *Retrovirology* 3:6).

eRNA19: H1 EMCV polyC CTE eRNA20: H1 ECMV-polyC Antisense

EMCV and EMC-like viruses share structural characteristics in their dsRNA, such as the presence of a homopolymeric polyC acid tract within the 5'-untranslated sequence. These polyC tracts are retained during viral replication in vitro and in vivo and are associated with virulence. This region may account for activation of MDA5 observed with EMCV viruses.

Here the INF dsRNA was deleted from eRNA17 (H1-dsRNA-CTE), and replaced with the EMCV polyC sequence in either orientation (eRNA19=forward, eRNA20=reverse, with CTE deleted). Each vector will make a single strand. eRNA19 in combination with eRNA20 will make a double stranded RNA, with a CTE sequence on a single strand.

eRNA34: H1 RTE CTE.

This clone replaces the INF ssRNA in eRNA17 H1 INF ssRNA CTE with a RTE CTE. These are two RNA export elements, combining RTEM26 (mutation of a RNA Transport Element from a rodent intracisternal A particle retroelement, mechanism of action is unknown) and CTE (a TAP/NXF1 binding export hairpin structure, that exports unspliced RNAs derived from simian type D retroviruses). The combination of the two is synergistic for nuclear export (Smulevitch et al, Supra, 2006).

Combination RNA Elements:

Combination of pDNAVACCUltra VAI (orientation 1=VARNAIA) and eRNA18 U6 INF ssRNA eRNA35: VARNAIA-U6 INF ssRNA O1 (convergent)

eRNA36: VARNAIA-U6 INF ssRNA O2 (divergent)

35: VARNAI► _________U6 ◄

36: _________U6◄ VARNAI ►

Combination of eRNA23 [eRNA7 (Repaired S35 Export Sequence)] and eRNA18 U6 INF ssRNA eRNA38: eRNA23-U6 INF ssRNA O1 (convergent)

eRNA39: eRNA23-U6 INF ssRNA O2 (divergent)

38: VARNAI S35► _________U6◄

39: _________U6◄ VARNAI S35►

The following composite RNA elements combine VARNAIA and the U6 INFdsDNA tRNA (eRNA11) in different orientations:

eRNA41 Series: VARNAIA U6 INFdsDNA tRNA

These composite RNA elements combine VARNAIA and the U6 INFdsDNA tRNA (eRNA11) in different orientations:

41: ► tRNA_________U6◄ VARNAI►

41e: VARNAI► ► tRNA_________U6◄

41f: VARNAI► ► U6_________tRNA◄

41g: ► U6_________tRNA◄ VARNAI►

Or with Different eRNA11 Components eRNA41: eRNA41 orientation (eRNA11=dsRNA contains recessed U6 start 5' end)

eRNA41H: eRNA41 orientation (eRNA11a=dsRNA contains blunt U6 start 5' end)

eRNA41i: eRNA41 orientation (eRNA11=dsRNA to contain protruding U6 start 5' end; SEQ ID NO: 5); the single T base insert in eRNA41 used to create the forward tRNA strand terminator is underlined in FIG. 4.

eRNA41E+H: eRNA41E orientation (eRNA11a=dsRNA contains blunt U6 start 5' end)

Or with Different VARNAI Components eRNA41d: eRNA11=dsRNA contains recessed U6 start 5' end in combination with Adenoviral serotype 2 promoter box B in VARNAI (G to A change in box B resulting in Ad2 ttcgaaccc from Ad5 ttcgagccc).

eRNA41J: eRNA11a=dsRNA contains blunt U6 start 5' end, in combination with Adenoviral serotype 2 promoter box B in VARNAI (above).

Example 2: Identification of RNA Element Plasmids that Activate RIG-I

The vectors from Example 1 were tested for RIG-I activation using either a one or a two step assay. EGFP target gene expression was also monitored in the same experiments as a surrogate assay for PKR activation (PKR inhibits translation, leading to loss of antigen expression). All assays were performed using 24 well cell culture plates. In the two step assay, pI25luc (a reporter plasmid, with the luciferase gene driven by the interferon β promoter) and the cytoplasmic RNA receptor [either human RIG-I (hRIG-I), marine RIG-I (mRIG-I), human MDA5 (MDA5) or dominant negative hRIG-I control (DeNy); pUNO-hRIG-I, pUNO-mRIG-I, pUNO1-hMDA5 or pDeNy-hRIG-I respectively, Invivogen, San Diego Calif.] were cotransformed into human embryonic kidney cell line HEK293 (American Type Culture Collection, Manassas, Va.) using lipofectamine 2000 as described by the manufacturer (Invitrogen, Carlsbad, Calif.). Cells were grown in DMEM:F12+10% FBS at 37° C. with 5% $CO_2$. The transfection media was removed after 4 hrs incubation, and the test pDNAVACCUltra EGFP RNA element (eRNA) plasmids transfected the next day. Expression (EGFP) and interferon β activation (luciferase) were determined 1 day after the second transfection using the FLX800 microplate fluorescence reader, directly for EGFP in black plates, and after activation with the Promega (Madison, Wis.) luciferase assay system in opaque plates for luciferase. In the one step assay, for each well of the 24 well plate, 0.1 ug pI25luc (a reporter plasmid, with the luciferase gene driven by the interferon β promoter), 0.1 ug of the cytoplasmic RNA receptor [either human RIG-I (hRIG-I), murine RIG-I (mRIG-I), human MDA5 (MDA5) or dominant negative RIG-I control (DeNy); pUNO-hRIG-I, pUNO-mRIG-I, pUNO1-hMDA5 or pDeNy-hRIG-I respectively] and 0.2 ug of the test plasmid were mixed in 50 uL DMEM (no serum) and cotransformed into human cell line HEK293 using lipofectamine 2000 (1.5 uL/50 uL DMEM) as described by the manufacturer (Invitrogen, Carlsbad, Calif., USA). Cells were grown in DMEM:F12+10% FBS at 37° C. with 5% $CO_2$. The transfection media was removed after 4 hrs incubation. Expression (EGFP) and interferon β activation (luciferase) were determined 24-35 hrs post transfection using the FLX800 microplate fluorescence reader, directly for EGFP in black plates, and after activation with the Promega luciferase assay system in opaque plates for luciferase.

The potency of single RNA element DNA vaccines on RIG-I activation of these constructs was determined. The results are summarized in Table 1. The results from a two step assay are shown in FIG. 5.

RIG-I activation was observed with the C26 and Bgal728 constructs. These constructs were disclosed in Williams, Supra, 2006 as inducers that dramatically improved the immunostimulatory activity of the pDNAVACCUltra vector (TNFα production), without activating PKR mediated translation inhibition, after lipofectamine 2000 transfection into RAW 264.3 mouse macrophage cell line. The results disclosed herein demonstrate that these constructs are RIG-I activators.

VARNAI containing DNA vaccines activated RIG-I, and were more potent activators than the C26 or Bgal728 constructs. While the related EBER1 RNA is a RIG-I activator (Samanta et al, Supra, 2006) the activation observed with VARNAI was surprising, in light of the Weber et al, Supra, 2006 finding that while the pAdVantage VARNAI/II containing plasmid activate the interferon response in transfected cell lines, they do not activate the RIG-I/MDA5 pathway, or other known pathways (i.e. no activation of IRF-3, which is a mediator of RIG-I signaling; Weber F, Wagner V, Kessler N, Haller O. 2006. *J Interferon Cytokine Res* 26: 1-7). This may be due to differences in cell lines or assay conditions. For human vaccination, VARNAI is preferable to EBER1, since EBER1 binds multiple cellular proteins, and has documented growth stimulating properties. V A RNAI has not been attributed with these adverse properties, and is considered safe for vaccine use. As a natural adenovirus gene, it is currently included in multiple adenovirus vaccines in clinical development. The increased level of EGFP expression may be due to the PKR inhibitory action of VARNAI. Indeed, VARNAI is included in the pAdVAntage™ Vector (Promega, Madison Wis.) plasmid backbone to increase target gene expression of cotransfected plasmids by this mechanism (Groskreutz, D. Schenborn, E. 1994 *Promega Notes* 48, 8.12) as well as PKR independent stimulation of gene expression potentially through inhibition of RNA interference (Andersson M G, Haasnoot P C J, Xu N, Berenjian S, Berkhout B, Akusjarvi G. 2005. *J. Virol.* 79:9556-9565; Lu S. Cullen B R. 2004. *J. Virol.* 78: 12868-12876). VARNAI-including backbones have not been used to increase immunostimulation, or suggested for such an application, as is disclosed herein. Indeed, Weber et al, Supra, 2006 do not suggest this application, and instead speculated that the interferon inducing capacity of V A RNAs observed in cell lines is most likely negligible under natural conditions and hypothesize that V A RNAs may stabilize spurious levels of interferon β mRNA induced by DNA transfection.

various VARNAI modifications, including various flanking sequence modifications or serotype swaps can be made to the VARNAI, since these do not reduce RIG-I activation.

The strongest RIG-I activator was eRNA11a (Table 1). This is a two component activator. It produces a single stranded RNA with a 5' tRNA from the tRNAVal promoter. The art teaches that the 5'-PPP will be removed from this RNA during tRNA processing, and the resulting RNA will be exported to the cytoplasm. Conversely, it is possible that this specific tRNAVa1 fusion may have the novel property of export without processing, since a tRNA-ribozyme fusion of Kuwabara et al, Supra, 2001 with the same linker was reported to have been exported to the cytoplasm without extensive 5' end removal. The observation of RIG-I activation with eRNA11D (tRNA-100 bp ssRNA, no U6 RNA) would be consistent with the tRNA retaining the 5'-PPP. The second component is the complementary strand of the

TABLE 1

RNAe constructs

| Name+ | Pol III Promoter | RNA Export | Structure and orientation | RNA | EGFP | RIG-I Activation |
|---|---|---|---|---|---|---|
| Control | None | None | None | None | | – |
| mU6++ | U6 | None | U6▶ short RNA | Unstructured | | – |
| Bga728++ | U6 | minihelix | U6▶ Hairpin with microRNA loop | dsRNA hairpin | | + |
| C26++ | U6 | none | U6▶ PKR aptamer | structured RNA | | + |
| H1- mU6 INF dsRNA | H1 and U6 | None | H1▶ 60 bp RNA◀ U6 | dsRNA | ↓ | NA |
| H1- mU6 INF dsRNA repaired | H1 and U6 | None | H1▶ 100 bp RNA◀ U6 | dsRNA | ↓↓ | + |
| VARNAIA | VAI | minihelix | VAI▶ | structured RNA | ↑ | ++ |
| VAI 2x | VAI | minihelix | ◀ VAI◀ VAI | structured RNA | | ++ |
| VAI/VA2 | VAI | minihelix | VAI▶ VAII▶ | structured RNA | | ++ |
| eRNA7 | VAI | minihelix | VAI▶ (S35) | structured RNA | | + |
| eRNA10 | VAI | minihelix | VAI-HCV IRES▶ S35) | structured RNA | | + |
| eRNA23 | VAI | minihelix | VAI▶ (S35) | structured RNA | | + |
| eRNA24 | VAI | minihelix | VAI-HCV IRES▶ S35) | structured RNA | | + |
| eRNA31 | VAI | none | VAI-▶ shRNA | structured RNA | | + |
| eRNA42 | VAI | minihelix | Extended 5' VAI▶ | structured RNA | | ++ |
| eRNA44 | VAI | minihelix | VAI▶ internal deletion | structured RNA | | – |
| eRNA11 | tRNAVal and U6 | tRNA | tRNAVal▶ 100 bp dsRNA◀ U6 | dsRNA recessed 5' PPP | | ++ |
| eRNA11A | tRNAVal and U6 | tRNA | tRNAVal▶ 100 bp dsRNA◀ U6 | dsRNA blunt 5' PPP | | +++ |
| eRNA11B | tRNAVal and U6 | tRNA | tRNAVal▶ 100 bp dsRNA◀ U6 | dsRNA recessed 5' PPP | | ++ |
| eRNA11C | tRNAVal and U6 | tRNA | tRNAVal▶ HCV 3' NTR◀ U6 | dsRNA recessed 5' PPP | | + |
| eRNA11D | tRNAVal | tRNA | tRNA▶ 100 bp RNA | No structure | | + |
| eRNA18 | U6 | none | 100 bp dsRNA◀ U6 | No structure | | + |
| eRNA12 | tRNAVal | tRNA | tRNA▶ HCV IRES | structured RNA | | + |
| eRNA17 | HI | CTE | HI▶ 100 bp dsRNA CTE | Structured RNA | | – |
| eRNA19 | HI | CTE | HI▶ EMCV polyC CTE | Structured RNA | | – |
| eRNA34 | HI | RTE-CTE | HI▶ RTE -CTE | Structured RNA | | – |
| | | | | structure | | |

Unexpectedly, all the substitutions of VARNAI with internal insertions (of known RIG-I ligands, internal deletions, or 3' hairpin sequences) reduced the RIG-I activation ability. This may be due to: 1) internal sequences may cause premature termination of pol III transcription even in the absence of TTTT terminators or; 2) some internal sequences such as HCV IRES increase the length beyond 300 bp, which may be too long for effective DNA polymerase III transcription; or 3) some sequences such as the terminal shRNA additions may interfere with nuclear export by preventing minihelix formation. These results teach that production of RIG-I ligands from plasmid vectors requires careful design, as outlined above. Modifications that do not affect the integrity of the VARNAI RNA, such as serotype 5 to 2 swaps in the B box (e.g. eRNA41H to eRNA41J change), or extensions of the 5' flanking sequences (e.g. eRNA42), do not adversely affect RIG-I activation. This teaches that this embodiment of the invention includes dsRNA transcribed convergently using the U6 promoter. This second strand, by itself, shows RIG-I activation (eRNA18, Table 1). While this short RNA may have a 5'-PPP, there is no obvious mechanism of cytoplasmic transport and U6 transcribed RNAs are typically localized to the nucleus. The composite construct, eRNA11, has much more potent RIG-I activation than the single component eRNA11D or eRNA18 (Table 1). While not limiting the application of embodiments of the invention, this may be due to dsRNA forming by hybridization of the two complementary strands, followed by tRNA mediated export of the dsRNA.

While not experimentally verified or necessary of application of embodiments of the invention, a 5'-PPP may be retained on the U6 promoter transcribed strand. In the potential dsRNA configuration (i.e. when annealed to the tRNA-opposite strand) it is unknown what the optimal 5' end is, since the art does not clearly teach the best configuration for presentation of a 5'-PPP in a longer dsRNA to RIG-I. Marques et al, Supra, 2006 teach that blunt siRNAs ranging from 21 to 27 nucleotides in length activated the interferon system and they speculated that the presence of 3'-overhangs impaired RIG-I ability to unwind the dsRNA substrate and activate downstream signaling to the transcription factor IRF-3. This conflicts with the teachings of Hornung et al, Supra, 2006, who demonstrated that blunt ends are not required for RIG-I activation. The optimal 5'-end was herein determined experimentally using blunt, recessed or protruding 5'-PPP (FIG. 4). These results, summarized in Table 2 and FIG. 6, clearly demonstrate a blunt end is preferred for RIG-I activation with this RNA expressed from a plasmid vector.

RIG-I activation than 100 bp RNA (Kato et al, Supra, 2006), while 30 bp RNA will not be extensively edited by ADAR) and the base composition or degree of secondary structure, and then testing using the 1 step and/or 2 step RIG-I activation assays disclosed herein, or other RIG-I activation assays known in the art.

Activation was not observed when RIG-I ligands were expressed from the human H1 promoter (eRNA17, eRNA19, eRNA34; Table 1). Additional H1 constructs tested that did not activate RIG-I included HI HCV IRES CTE (eRNA21) alone or in combination with eRNA35 (as eRNA37, which showed no improvement compared to eRNA35 parent plasmid); eRNA32: HI EMCV-polyC RTE CTE (690 bp transcript); eRNA33: H1 HCV IRES RTE CTE

TABLE 2

Composite RNAe constructs (Bold)

| Name | Pol III Promoter | RNA Export | Structure and orientation | RNA | EGFP | Activation RIG-I | Mda5 |
|---|---|---|---|---|---|---|---|
| Control | None | None | None | None | | − | − |
| VARNAIA | VAI | minihelix | VAI▶ | structured RNA | ↑ | ++ | +++ |
| VAI 2x | VAI | minihelix | ◀ VAI◀ VAI | structured RNA | | ++ | +++ |
| eRNA11 | tRNAVal and U6 | tRNA | tRNAVal▶ 100 bp dsRNA◀ U6 | dsRNA recessed 5' PPP | | ++ | +/− |
| eRNA11A | tRNAVal and U6 | tRNA | tRNAVal▶ 100 bp dsRNA◀ U6 | dsRNA blunt 5' PPP | | +++ | +/− |
| eRNA18 | U6 | none | 100 bp dsRNA◀ U6 | No structure | | + | + |
| eRNA35 | VAI and U6 | Minihelix | VARNAI▶ 100 bp dsRNA U6◀ | structured RNA and ssRNA | | ++++ | +++ |
| eRNA36 | VAI and U6 | Minihelix | 100 bp dsRNA U6◀ VARNAI▶ | structured RNA and ssRNA | | ++++ | +++ |
| eRNA41 | VAI, tRNA and U6 | Minihelix and tRNA | ▶ tRNA 100 bp dsRNA U6◀ VARNAI▶ | structured RNA and dsRNA (recessed 5' PPP) | | +++++ | +++ |
| eRNA41H | VAI, tRNA and U6 | Minihelix and tRNA | ▶ tRNA 100 bp dsRNA U6◀ VARNAI▶ | structured RNA and dsRNA (blunt 5' PPP) | ↑ | ++++++ | ++++ |
| eRNA41i | VAI, tRNA and U6 | Minihelix and tRNA | ▶ tRNA 100 bp dsRNA U6◀ VARNAI▶ | structured RNA dsRNA (extended 5' PPP) | | +++++ | ++++ |
| eRNA41j | VAI(box2 sero 2), tRNA and U6 | Minihelix and tRNA | ▶ tRNA 100 bp dsRNA U6◀ VARNAI▶ | structured RNA and dsRNA (blunt 5' PPP) | ↑ | ++++++ | |
| eRNA41e | VAI, tRNA and U6 | Minihelix and tRNA | VARNAI▶ ▶ tRNA 100 bp dsRNA U6◀ | structured RNA and dsRNA (recessed 5' PPP) | | +++++ | ++++ |
| cRNA41e + h | VAI, tRNA and U6 | Minihelix and tRNA | VARNAI▶ ▶ tRNA 100 bp dsRNA U6◀ | structured RNA and dsRNA (blunt 5' PPP) | ↑ | ++++++ | |
| eRNA41f | VAI, tRNA and U6 | Minihelix and tRNA | VARNAI▶ ▶ U6 100 bp dsRNA tRNA◀ | structured RNA and dsRNA (recessed 5' PPP) | | ++++ | ++++ |
| eRNA41g | VAI, tRNA and U6 | Minihelix and tRNA | ▶ U6 100 bp dsRNA tRNA◀ VARNAI▶ structure | structured RNA, dsRNA (recessed 5' PPP) + | | ++++ | ++++ |

Interestingly, substitution of a structured RNA (the HCV 3' NTR) for the influenza 100 bp RNA resulted in lower RIG-I activation (eRNA11C, Table 1). The HCV 3' NTR is a known RIG-I ligand, and in vitro transcribed RNA is a strong RIG-I activator. Critically, the results disclosed herein demonstrate that the RIG-I ligands taught in the art (HCV 3' NTR and HCV IRES identified from in vitro transcribed RNA or native viral RNA isolated from cells) do not function as such when cloned into plasmid backbones. This further teaches that ligands expressed from a plasmid need to be optimized for RIG-I activation, and that ligands defined in the art are not predictive of optimal ligands for inclusion in DNA vaccine plasmids. While not limiting the application of embodiments of the invention, the failure of the HCV 3' NTR to be a strong activator may be due to the high level of secondary structure; each strand may form stable secondary structures, which reduces annealing between strands, and subsequent tRNA mediated nuclear export.

One skilled in the art can further optimize the existing RIG-I activating constructs reported herein, by varying the length of the RNA (e.g. from 20 to 1000 bp, preferably 30 to 200 bp; 200 bp RNA has been reported to show stronger (840 bp transcript); eRNA27 H1 EMCV polyC helix and eRNA28 H1 HCV IRES helix (the 3' end of the EMCV or HCV IRES was modified to form a minihelix to allow nuclear export); eRNA21 H1 HCV IRES CTE and eRNA22 H1 HCV IRES antisense CTE, alone or in combination with each other; eRNA20 H1 ECMV-polyC antisense. Several of these plasmids, including those expressing the putative MDA5 ligand EMCV polyC region also did not activate human MDA5. It is unknown what the basis is for the general failure to activate RIG-I or MDA5 with human H1 promoter driven constructs. One possibility is that sufficient RNA is not made, since this promoter is not as strong as the murine U6 promoter. Alternatively, in the case of RIG-I activation, the 5'-PPP may be removed from H1 transcriptions. Interesting, Plumet et al, Supra, 2007, also failed to activate RIG-I using a plasmid vector (pSuper-H1) in which the pol III H1 promoter was used to express a known RIG-I activator, measles viral leader. Collectively, the results disclosed herein teach: 1) pol III promoters for plasmid expressed RIG-I or MDA5 ligands are not equivalent, and that U6, tRNA and VARNAI promoters are superior to the H1 promoter and; 2) RIG-I and MDA5 ligands taught in the art (identified from in vitro transcribed RNA or native viral RNA isolated from cells) do not function as such when cloned into plasmid backbones.

Example 3: Synergistic Immune-Stimulation with Combinations of RNA Elements

The optimal RNA elements (VARNAI, eRNA11, eRNA11a), defined in Example 2, were then combined into a composite RNA element containing both individual components as described in Example 1. The surprising, unexpected result of synergistic activation of RIG-I in the composite RNA elements is shown in Table 2, and FIGS. 7-10. In FIG. 7, the composite structure eRNA41 (eRNA11 and VARNAI) demonstrate synergistic activation of RIG-I. In FIG. 8, a composite RNA element with two copies of VARNAI (VA2×) shows additive activation of RIG-I, while a composite of eRNA11a and VARNAI, 41H, is unexpectedly synergistic. As with the single eRNA containing vector, eRNA11, a blunt 5' end (41H) in the eRNA11 component of the composite element is superior to recessed (eRNA41) or protruding (eRNA41i) (FIG. 9). Importantly, this is true for both human and murine RIG-I. This demonstrates that the eRNA41H RIG-I activator is not species specific, and should function in mice and humans. As well, strong activation of MDA5 bp composite eRNA was also observed (FIG. 9 and FIG. 10). In the case of MDA5, activation was not as dependent on blunt 5' end in the eRNA11 component; 5'-triphosphate is not a known ligand for MDA5, and MDA5 activation may be stronger with ssRNA than dsRNA (Kato et al, Supra, 2006), so these differences may reflect differences in RIG-I versus MDA5 ligand requirements. Regardless, the eRNA41H (and eRNA41J, a version with the adenoviral VARNAI modified in a single base in the box B RNA polymerase III recognition site to that of Ad2, rather than Ad5) composite eRNA vectors are strong MDA5 activators, and strong cross species RIG-I activators. The synergistic activation of RIG-I is not orientation dependent (FIG. 10) although some orientations are stronger than others, with the parent 41 and 41e vectors strongest for RIG-I activation and the 41g strongest for MDA5 activation. This again may reflect differences in preferred ligands for RIG-I and MDA5. The strongest RIG-I activating composite eRNAs in the 41 and 41e orientations (containing eRNA11) contain the eRNA11a blunt 5' end; these are eRNA41H, eRNA41J (in the 41 orientation) and eRNA41e+h (in the 41e orientation). Fold induction of interferon β promoter by RIG-I is much higher for eRNA41H than eRNA41. These activations are specific, since activation is not observed when a dominant negative RIG-I receptor (DeNy) is substituted for RIG-I or MDA5 receptors (FIGS. 9-10). Synergy is also observed with eRNA35 and eRNA36, which are two different orientations of eRNA18 (U6 only) and VARNAI. Thus, RIG-I activation synergy is observed with two different eRNA combinations: eRNA18 and VARNAI, and eRNA11 and VARNAI. eRNA35 and eRNA36 are also strong MDA5 activators; this may be due to the observation that MDA5 activation is better with ssRNA (such as produced by eRNA18) than dsRNA (as produced by eRNA11) (Kato et al, Supra, 2006).

The eRNA41H vector was tested in a one step assay for induction of interferon α. The interferon α reporter pNIFTY2-IFA-SEAP (Invivogen, San Diego, Calif.) was substituted for pI25luc in the one step assay of Example 2. 40 ng eRNA41H plasmid (or control plasmid without eRNA41H) was transfected per well with mRIGI and pNIFTY2-IFA-SEAP. SEAP expression was detected after transfection of the eRNA41H vector, but not vector without eRNA41H. Collectively, these results demonstrate eRNA41H induces both interferon α and β, through activation of the RIG-I pathway.

The composite eRNA vectors also surprisingly enhances target gene expression (FIGS. 8, 9 and 10). While the composite elements are designed to not activate PKR through inclusion of the VARNAI component, the enhanced target gene expression beyond the effect of VARNAI alone was unexpected. While not limiting the application of embodiments of the invention, enhanced target gene expression may be mediated by unexpected interactions between cofactors required for RNA polymerase II (for CMV transcription) and RNA polymerase III (eRNA transcription). The tRNA and VARNAI RNA polymerase III promoters are gene internal type 2 RNA polymerase III promoters, while U6 (and H1) are type 3 gene external RNA polymerase III promoters. While type II promoters have less or no cofactor requirements in common with RNA polymerase II, the U6 type 3 promoters require several cofactors in common with RNA polymerase II, including SNAPc, Oct1, STAF, YY1 (reviewed in Schramm L, Hernandez N. 2002. *Genes Dev* 16: 2593-2620).

The observation, or mechanism, that explains the surprising synergistic activation of RIG-I by composite eRNA is not taught in the art. For example, while Jarczak D, Korf M, Beger C, Manns M P, Kruger M, 2005 *FEBS J* 272: 5910-5922 teach that two plasmids with different DNA polymerase III promoters (tRNA and U6) improves ribozyme expression over 2 U6 or 2 tRNA plasmids, the effect is not synergistic, and the authors speculated that use of different promoters might avoid limitation of cellular transcription factors. While positive and negative interactions between elements of different classes of RNA polymerase III promoters has been reported (Parry H D, Mattaj I W, *EMBO J.* 9: 1097-1990) these were composite elements rather than composite promoters. While not limiting the application of embodiments of the invention, synergy may be the result of enhanced RNA expression from the composite RNA polymerase III promoters. Since eRNA35 and 36 show synergy, the important components may be combining U6 and VARNAI type promoters. This is not taught in the art. Chang Z, Westaway S, Li S, Zaia J A, Rossi J J, Scherer L J, 2002 *Mol. Ther.* 6: 481-489 disclose a dual U6 tRNA promoter wherein the U6 promoter is positioned upstream of the tRNA promoter to enhance tRNA promoter driven ribozyme expression. Zu Z, Xia X 2005 US Patent Application 20050130184, disclose that close proximity of the CMV enhancer and the U6 promoter lead to increased U6 expression. A hybrid CMV enhancer upstream of the H1 promoter that improves H1 expression was disclosed by Hassani Z, Francois J C, Alfama G, et al, 2007 *Nucl. Acid Res.* 35:e65.

None of these disclosures teach the enhancement observed in the composite RNA element embodiments of the invention; since the CMV enhancer is present in all constructs, the enhancement is due to combination of the two RNA polymerase III promoters.

One skilled in the art can further optimize the synergistic activation of RIG-I in the existing composite RIG-I activating constructs reported herein, by varying the component promoters (e.g. human or rat U6 promoter substitution for murine U6 promoter), and then testing using the 1 step and/or 2 step RIG-I activation assays disclosed herein, or other RIG-I activation assays known in the art.

Example 4: VAI Activation of MDA5

While synthetic activators such as polyI:C have been identified as activators of MDA5, the natural ligand for MDA5 has not been identified despite extensive evaluation of RNA viruses. We have surprisingly determined that adenovirus VA RNAI (VARNAI or VAI) is a potent MDA5 activator, and that MIDAS activation is reduced by subtle central domain modifications that also reduce PKR inhibition. This may indicate MDA5 is adapted to detect conserved structures of the central domain of VARNAI that are necessary for PKR inhibition. PKR inhibition is essential for viral replication, so MDA5 activation by VARNAI may reflect a previously unknown role for MDA5 in control of double stranded DNA virus infections such as adenovirus. The art teaches that VARNAI is not an MDA5 activator. Investigation of innate immune response to adenovirus infection identified several mechanisms of innate immune response activation, none of which included MDA5 activation. The authors conclude that DNA-sensing is the primary activator of IRF-3 (Nociari M, Ocheretina O, Schoggins J W Falck-Pedersen E. 2007 *J. Virol.* 81: 4145-4157). Transfection of cells with a VAI/VAII containing plasmid was found to induce type I interferon production, but not through IRF-3 activation (Weber et al, Supra, 2006). This teaches that interferon production mediated by VAI/VAII is not mediated by MDA5, since IRF-3 is activated by MDA5 signaling.

For the following experiments, the one step RIG-I or MDA5 activation assay (Example 2) was modified as follows. In brief, for each well of the 24 well plate, 0.1 ug pI25luc (a reporter plasmid, with the luciferase gene driven by the interferon β promoter), 0.1 ug of the cytoplasmic RNA receptor [human RIG-I (hRIG-I)=pUNO-hRIG-I, or pUNO1-hMDA5, InvivoGen corporation, San Diego Calif.], 0.15 ug of an internal control EGFP plasmid (EGFP is used to standardize transfections) and <0.1 ug of the test plasmid were mixed in 50 uL DMEM (no serum) and cotransformed into human cell line HEK293 using lipofectamine 2000. In this assay, the control EGFP was utilized as an internal transfection control, and the standardized RIG-I or MDA5 activation expressed as the ratio of luminescence (RIG-I or MDA5 activation) to EGFP.

During investigation of the basis for the strong RIG-I activation observed with eRNA41H, it was determined that the synergy between the two components (eRNA11a and VARNAI) in cis (e.g. eRNA41H or eRNA41E+H) was also observed when the two components are provided to the cell as a mixture of the two plasmids (i.e. in trans-unlinked) (FIG. 11). This is very specific to VARNAI, since addition of other eRNAs do not show synergy with eRNA11a for RIG-I activation. Activation synergy is also seen, but is lower with VARNAI/II. This demonstrates that RIG-I activation synergy is not due to a physical linkage between the components and that activation is strongest with VARNAI.

As well, the strong MDA5 activation with eRNA41H was mostly due to activation by the VARNAI component. In this case, synergy is not observed with eRNA11a, with most MDA5 activation contributed by the VARNAI component (FIG. 11). While VARNAI is a relatively weak RIG-I activator (weaker than eRNA11a), it is surprisingly by far the strongest MDA5 activator of the single component eRNAs tested (FIG. 11).

The one step assay was performed as described above, using either 1) both hRIG-I and hMda5 receptors (20 ng each per well) or 2) neither receptor. The results (FIG. 12) demonstrate that in the presence of both receptors, VARNAI is more potent than eRNA11a. This is possibly due to the ability of VARNAI to activate both RIG-I (weak) and MDA5. In the absence of added receptor, VARNAI was a weak activator. As before, the strongest activation was observed with the combinations of VARNAI and eRNA11a (cis and trans), either with RIG-I/MDA5 or no receptor added. Further, VARNAI was again the strongest activator in trans to eRNA11a; weaker activation was observed with eRNA31b and eRNA31c (intact VARNAI RNA's that additionally contain a 3' hairpin; Example 1). Activation may be weaker due to impaired nuclear export of these RNAs by disruption of the terminal minihelix.

These results demonstrate that native VARNAI is the strongest identified transactivator of eRNA11a induced interferon β activation. This activation is not an artifact of excess RIG-I or MDA5 receptors in the assay, since activation is also seen in native HEK293 cells, in which no additional receptor was added.

The basis for VARNAI activation was then evaluated, by testing the effects of subtle modifications to the central domain of this RNA on RIG-I and MDA5 activation. The central domain was unexpectedly found to be critical for VARNAI activation of MDA5, and VARNAI synergy with eRNA11a for activation of RIG-I.

Construction and analysis of the following constructs demonstrates this point.

eRNA41H-PKR1=pDNAVACCUltra EGFP eRNA41H with the VAI component engineered to contain the eRNA44A deletion (Example 1).

eRNA41H-PKR2=pDNAVACCUltra EGFP eRNA41H with the VAI component engineered to contain the VAI S35 modification (eRNA23; Example 1).

Both constructs eliminated VARNAI activation of MDA5, and VARNAI synergy with eRNA11a for activation of RIG-I: VARNAI is an inhibitor of PKR, and also a weak inhibitor of ADAR adenosine deaminase (which edits RNA content from A to I) and a weak activator of OAS (which activates RNaseL to degrade RNA). Therefore, it is a possibility that the highly modified VARNAI molecules used in PKR 1 and 2 activate these RNA degradation enzymes, leading to RNaseL-mediated degradation, or ADAR mediated loss of immunostimulatory activity (due to A to I editing), or ADAR mediated nuclear retention (due to extensive A to I editing) of the eRNA11a immunostimulatory RNA. The following constructs were made to test this possibility.

eRNA41H-PKR3 (L3) and eRNA41H-PKR4 (L4)=pDNAVACCUltra EGFP eRNA41H with the VAI component modified in the central domain.

These L3 and R1 mutations are described in Ma Y, Mathews, M B *RNA* 1996 2: 937 and are 2 bp changes in the central region that has been shown to be inactive for PKR inhibition, yet they are transcribed at high level in cell culture and maintain a VARNAI-like RNA secondary structure. Both constructs eliminated VARNAI activation of MDA5, and VARNAI synergy with eRNA11a for activation of RIG-I. However, the PKR3 and 4 modifications may not specifically reduce only PKR activation, since the central domain of VARNAI is also needed for inhibition of ADAR activation (Lei M, Liu Y, Samuel C E. 1998 *Virology* 245:188-196). The following construct was made to test this possibility.

eRNA41H-PKR5 (pm91)=pDNAVACCUltra EGFP eRNA41H with the VAI component modified in the central domain.

In PKR5, the VARNAI cassette was slightly modified in the central domain to eliminate only PKR inhibition (and retain ADAR inhibition). This pm91 mutation is described in Rahman et al, Supra 1995 and is a 1 bp change in the central region that has been shown to be inactive for PKR inhibition, but retains ADAR inhibiting activity (Lei et al, Supra, 1998).

The results of testing these alterations on MDA5 (FIG. 13) and RIG-I (FIGS. 14-16) activation were determined. PKR 1-4 retain residual 11a component activity for RIG-I activation but eliminated both the synergistic activation of RIG-I and VARNAI mediated MDA5 activation activity. This demonstrates that the VARNAI central domain is surprisingly required for both MDA5 activation, and synergistic RIG-I activation with eRNA11a. The results are not consistent with synergistic interactions between these pol III promoters, or with VARNAI indirectly increasing interferon β RNA levels through inhibition of Dicer-mediated RNA interference as taught in the art by Weber et al, Supra, 2006, since the inactive PKR3 and PKR4 derivatives are 1 or 2 bp changes in the central domain that retain the Dicer binding terminal helix defined in Andersson et al, Supra, 2005.

PKR5 retains some synergistic activation of RIG-I as well as MDA5 activation activity. This surprisingly demonstrates that subtle modifications of the central domain can be used to create novel hybrid molecules that vary in potency of MDA5 activation and PKR inhibition.

While not limiting the scope of embodiments of the invention to any specific mechanism of action, the results are consistent with several possible mechanisms of action for synergistic increase in RIG-I mediated interferon β activation when VARNAI and eRNA11a are combined. For example, eRNA11a may be a PKR ligand as well as a RIG-I ligand. RIG-I binds RNA with a lower affinity than PKR (Gantier M P, Williams B R G 2007 *Cytokines Growth Factor Review* 18:363-371), so most eRNA11a may be unproductively bound to PKR. VARNAI is a high affinity PKR ligand that may compete with eRNA11a for PKR binding, freeing eRNA11a (which is a stronger RIG-I activator) for RIG-I activation (ligand titration model). Alternatively, eRNA11a may bind and activate ADAR which would initiate Adenosine to Inosine editing, preventing nuclear export and/or reduce immunostimulatory activity. Titration of ADAR by VARNAI, and subsequent inhibition of ADAR may reduce eRNA11a editing (ligand destruction model). In this model, inclusion of an ADAR inhibitor, such as VARNAI, can be used to increase export of dsRNA from the nucleus, through inhibition of ADAR mediated RNA editing. Alternatively, a receptor (e.g. MDA5, PKR, OAS) that responds to VARNAI may synergistically activate with RIG-I activating eRNA11a. In this manner, the presence of ligands for both receptors dramatically increases the overall level of I3 interferon promoter induction (ligand synergy model).

The analysis of the components of eRNA11a (FIG. 14) also surprisingly demonstrate that double stranded RNA per se is not the mediator of RIG-I activation, because the H1-mU6 (StuI) INF dsRNA repaired construct was a weak activator compared to eRNA11a. This construct makes the same dsRNA as eRNA11a but differs in that the tRNA component is not present. These results demonstrate that the tRNA component of eRNA11a is critical to RIG-I activation, and that double stranded RNA is insufficient to account for the interferon activating potential of eRNA11a. In example 2, it was disclosed that the blunt termini of the eRNA11a molecule increases interferon induction compared to recessed or protruding termini. VARNAI activation of MDA5 also requires specific structures—the 41H PKR3 and PKR4 derivatives are similarly double stranded as the parent RNA, yet have completely eliminated interferon induction. Collectively, these results teach that the eRNA element embodiments of the invention activate interferon through specialized RNA structures, and do not activate interferon in cells through formation of dsRNA per se as is taught by Pollo et al, Supra, 2000.

As well, activation is seen with the eRNA41H (150) and eRNA41H (Cone) vectors. These vectors contain one (150) or several (Cone) copies of a 50 bp sequence inserted internally within the eRNA11a component of eRNA41H. This 50 bp sequence contains no Pol III terminators on either strand, and extends the length of the eRNA11a RNA by 50 bp (eRNA41H 150). The observed I3 interferon promoter activation demonstrates that the length of RNA in eRNA11a can be varied while retaining RIG-I/MDA5 activation. The optimal length and composition can be determined by an investigator skilled in the art, by varying the eRNA11a insert and testing immunostimulation using the described assays or equivalent.

The eRNA41H (DT) is a second DNA vaccine plasmid backbone, which contains a different promoter, antigen and eukaryotic terminator. The activation observed with this vector demonstrates that the eRNA41H activator functions in different DNA vaccine plasmid backbones and can therefore be transferred into alternative vectors as needed. An analysis of activation of eRNA41H, eRNA41J and eRNA41E+H at different target plasmid dosages and backbones is summarized in FIG. 17. No difference between eRNA vectors was observed, with activation>2 fold over background observed at the lowest tested target plasmid dose (5 ng/transfection). eRNA41H and eRNA41E+H contain the same component RNAs in different orientations. This demonstrates that different orientations of the component RNAs within the composite eRNA are functional. eRNA41H functioned in the three different vector backbones tested—this is consistent with the eRNA41H(DT) results above, and demonstrates eRNA function is not vector specific and can therefore be incorporated into a variety of alternative vector backbones.

Thus, VAI can be combined, in a DNA vaccine vector, with one or more activating dsRNA elements, to selectively induce RIG-I, MDA5 or OAS responses without PKR mediated antigen expression reduction. Such vaccines could be superior in viva to existing replicon vaccines, by combining high antigen expression with RIG-I mediated dendritic cell maturation and interferon production (Lopez C B, Jount J S, Moran, T M. 2006 *J Virol.* 80: 3128). As well, RIG-I and TLR9 (from unmethylated CpG motifs in the vaccine plasmid backbone) mediated innate immunity activation may be synergistic to each other, based on known synergy between TLR3 (dsRNA ligand) and TLR9 (CpG ligand) activation pathways (Whitmore M M, DeVeer M J, Edling A, Oates R K, Simons B, Linder D, Williams B R G. 2004. *Cancer Research.* 64: 5850-5860). Finally, the substitution of DNA vectors containing these elements for the existing virus-derived replicon vectors would prevent the acquired immunity associated with the use of such virus-derived vectors, and would thus not limit the future use of the DNA vectors to deliver other antigens and eRNA.

Example 5: In Vivo Evaluation of Influenza eRNA Vectors

The WHO Influenza Surveillance Network has characterized H5N1 influenza viruses isolated from humans and animals from several countries affected by the 2004/2005 H5N1 outbreak in Asia and made recommendations on the antigenic and genetic characteristics of H5N1 viruses suitable for vaccine production (strains A/Vietnam/1194/04, A/Vietnam/1203/04 and A/Hongkong/213/03). Influenza A HA has not typically been codon optimized for use in DNA vaccines in chickens, mice and primates. This is consistent with the fact that these proteins must be made in these hosts for the virus to replicate. A native (secreted-membrane associated) version of the A/Vietnam/1203/04 HA gene (AY651334) was synthesized (by DNA2.0, Menlo Park, Calif.). The synthetic gene (herein denoted as HA) was designed to afford simple cloning into the pDNAVACCUltra vectors. For safety (i.e. gene transfer during immunization to infecting non pathogenic virus) the HA gene was human codon optimized with the DNA2.0 codon optimization software to reduce genome homology. As well, the multiple basic amino acid motifs at the HA cleavage site (correlative with pathogenicity) was replaced with the corresponding region from several nonpathogenic influenza strains.

Two HA expressing backbones with or without eRNA41H or eRNA41J were tested for immunogenicity (4 mice per group) in viva. Twenty (20) μg plasmid was injected into 1 muscle (quadriceps) of female BALB/c mice (6-8 weeks old) in three doses (day 0, 14, and 28). Serum samples were taken at day 42 and tested for anti-HA IgG response. Anti-HA specific total IgG, IgG2a, and IgG1 levels were determined by standard ELISA assay using plates coated with Nature Technology Corporation produced recombinant *E. coli* produced A/Vietnam/1203/2004 HA HA2 domain, Sigma (St Louis, Mo.) detection antibodies, and the B D Biosciences OptEIA kit (B D Biosciences Pharmingen, San Diego Calif.) block, wash and detection reagents. Briefly, coated wells were blocked and incubated 2 hrs with diluted serum samples, the wells washed and signal detected by subsequent sequential incubation and washing with; goat anti mouse IgG (Fc)-biotin, then Streptavidin-horse radish peroxidase conjugate (total IgG) or; goat anti-mouse IgG1, then anti-goat IgG-biotin, then Streptavidin-horse radish peroxidase conjugate (IgG1) or; goat anti-mouse IgG2a, then anti-goat IgG-biotin, then Streptavidin-horse radish peroxidase conjugate (IgG1). The results are summarized in Table 3 and demonstrate; presence of eRNA41J increases anti-HA2 antibody response and shifts IgG2a/IgG1a ratio in NTC1 backbone; presence of eRNA41H increases anti-HA2 antibody response and shifts IgG2a/IgG1a ratio in NTC2 backbone. In summary, both vectors containing eRNA demonstrated increased IgG2a/IgG1 ratio, indicating eRNA increases $T_H1$ bias (IgG2a is $T_H1$ indicator, IgG1 subtype is TH2 indicator. $T_H1$ bias is correlative with increased cellular immune responses. As well, since the overall poor immunological response to DNA vaccines in humans has been attributed, in part, to significantly reduced expression of TLR9 in humans compared to mice, the magnitude of the improved response may be higher in organisms with reduced TLR9 expression compared to mice.

TABLE 3

Anti-HA response to eRNA plasmids

| Vaccine† | HA2 ELISA+ | IgG2a/IgG1++++ |
|---|---|---|
| Plasmid alone | 0.09 ± .005 | |
| NTC1 HA | 0.61 ± .48 | 7.7 ± 7.0 |
| NTC1 HA-eRNA41J | 1.08 ± .65 | 16.4 ± 9.5 |
| NTC2 HA | 0.75 ± .53 | 2.4 ± 2.5 |
| NTC2 HA-eRNA41H | 1.02 ± .54 | 8.5 ± 2.2 |

†NTC1 and NTC2 = two different CMV promoter based backbones
+Day 42 total anti-HA2 IgG results, mean $OD_{450}$ at 1:12,500 dilution. Mean ± SD
++++Ratio of $A_{450}$ at 1:500 dilutions, Mean ± SD.

Example 6: NTC7382 Backbone

It is desirable to improve promoter strength of NTC pDNAVACCUltra vectors. The NTC7382 promoter (CMV-HTLV-I-synthetic rabbit β globin intron-exon 2 SRF binding protein) is distinct from the CMV/R promoter described in Nabel G J, Sanchez A, Yang Z Y, Sullivan N. 2003 U.S. Pat. No. 7,094,598 B2 (CMV-HTLV-I-CMV intron) or the base pDNAVACCUltra CMV or SV40-CMV promoter. The NTC7382 promoter is composed of the novel combination of 1) CMV promoter and start of exon 1; 2) the HTLV-I R-U5 sequence which contains the 5' splice acceptor site; 3) a synthetic 3' acceptor site based on the rabbit β globin intron, and; 4) Splicing enhancer comprised of SR protein binding site (3 copies of GAAGAAGAC) to improve RNA export in exon 2, prior to 5) a kozak sequence upstream of the start codon for the gene of interest. The SR protein binding site sequence has been shown to act as a splicing enhancer (Lavigueur A. La Branche H, Kornblihtt A R, Chabot B. 1993. *Genes Develop.* 7: 2405) and has not been utilized as a component in a chimeric promoter. The NTC7382 promoter is shown in FIG. 18. The sequence of the NTC7382 promoter is given in SEQ ID NO: 6. Expression levels (of EGFP) from plasmids incorporating the NTC7382 promoter, or NTC7382 promoter with upstream SV40 enhancer, after transfection of the HEK293 cell line are dramatically increased versus CMV based promoter plasmids (Table 4).

TABLE 4

Expression levels (EGFP Fluorescence units) from plasmids incorporating the NTC7382, SV40-NTC7382, or CMV based promoter

| Vector name† | Promoter | Selection | RNA element | EGFP |
|---|---|---|---|---|
| pDNAVACCUltra-EGFP | CMV | Kan | No | 6,668 |
| NTC7382-EGFP (UP) | NTC7382 | Kan | No | 20,074 |
| NTC7382-EGFP-41H (UP) | NTC7382 | Kan | 41H | 27,095 |
| NTC7382-EGFP | SV40-NTC7382 | Kan | No | 9147 |
| NTC7382-EGFP-41H | SV40-NTC7382 | Kan | 41H | 21,545 |
| NTC8382-EGFP (UP) | NTC7382 | RNA-OUT | No | 31,788 |

†(UP) is a modified backbone wherein the SV40 enhancer and ISS sequences (see FIG. 1) are removed eRNA versions of NTC7382 were made, by simple swapping of the eRNA region into the plasmid backbone using flanking sites common to all the vectors, such as NotI-AflIII, or NheI-AflIII, or NotI-ApaLI, or NheI-ApaLI, or NotI-DraIII, or NheI-DraIII fragment swaps. eRNA function (RIG-I and MDA5 activation in vitro) in the NTC7382 vectors was equivalent to the original CMV based vector (FIG. 17) while antigen expression was enhanced (Table 4).

Example 7: NTC8382 Antibiotic Free Backbone

DNA vaccines are being developed for a variety of human, animal, bird and fish vaccine applications. The presence of an antibiotic resistance gene in the plasmid backbone is considered undesirable by regulatory agencies, due to 1) the potential activation and transcription of the genes from mammalian promoters after cellular incorporation into the genome and 2) the potential transfer of the antibiotic resistance gene to endogenous microbial fauna. As well, the presence of antibiotics in the fermentation culture leads to the potential contamination of the final product with residual antibiotics.

RNA based selectable markers have been developed. Morsey M A, 1999 U.S. Pat. No. 5,922,583 discuss in theoretical terms the use of plasmids expressing the sok or flmB antisense repressor RNAs as selectable markers by selecting and maintaining the plasmids in cells engineered to contain and express the cognate target toxin genes (hok and flmA, respectively). In the presence of the plasmid, toxin expression is repressed and cell viability is maintained. Cells that lose the plasmid will die. Construction and testing results for such vector systems were not disclosed by the inventor so the utility of such systems is unknown. Two groups have developed RNA based selection systems that utilize the endogenous RNAI/RNAII antisense regulators of the pMB1 origin. In both examples, chromosomal genes were engineered to contain an RNAII sequence within the untranslated region of the mRNA. In the presence of a ColE1 type plasmid, the plasmid encoded RNAI repressor binds the RNAII sequence and represses translation of the chromosomal gene. This gene can be an antibiotic resistance marker, transcriptional repressor (controlling expression of a second gene) or a lethal gene (Grabherr R, Pfaffenzeller I. 2006; US patent application US20060063232; Cranenburgh R M. 2005; World Patent Application WO2005052167). These systems are limited to existing ColE1 type origin containing plasmid vectors only.

Counterselectable markers are known in the art and include lacZ, glkA (sensitivity to 2-deoxyglucose) or galK. Knockdown of sugar transport and fermentation genes can be selected by the proton suicide method (Winkelman J W, Clark D P. 1984. *J. Bacteriol.* 160: 687). Other systems that can be counterselected are thymidylate synthase A (thyA), xylB (xylitol media), tetracycline and levansucrase (sucrose media) (reviewed in Reyrat J M, Pelicic V, Gicquel B, Rappuoli R. 1998 *Infection Immun.* 66: 4011-4017).

RNA based inhibition of engineered chromosomal streptavidin expression cassettes can be utilized for selection, by suppressing the toxicity of streptavidin (biotin binding). Such a system has been described (Szafranski P, Mello C M, Sano T, Smith C L, Kaplan D L, Cnator C R. 1997. *Proc. Natl. Acad. Sci.* 94: 1059).

Alternatively, an RNA that hybridizes to, and reduces translation of, a genomic sequence could be used to repress expression of a transcriptional regulator protein, for example the tetR repressor. If an antibiotic resistance marker is cloned under the control of the tetR repressor, the presence of the antisense RNA in the cell will inhibit tetR expression (if it is placed under the control of the antisense RNA), and derepress the antibiotic resistance gene. This would allow antibiotic selection for a plasmid, without inclusion of the antibiotic gene in the plasmid backbone.

Regulatory RNAs are described in the art. For example, a 109 bp RNA, spot 42, has been shown to specifically downregulate galK expression by binding to the Shine-Dalgarno region in the galETKM mRNA, blocking ribosome binding (Moller T, Franch T, Udesen C. Gerdes K, Valentin-Hansen. 2002. *Genes Devel.* 16: 1696). As well, Insertion Sequence 10 (IS10) encodes RNA-OUT, an antisense RNA that hybridizes to, and reduces translation of, the transposon gene expressed downstream of RNA-IN. (Pepe C M, Maslesa-Galic S, Simons R W. 1994. *Mol. Microbiol* 13: 1133).

The ParB locus (Hok and Sok) of plasmid R1 and the Flm locus (FlmA and FlmB) of F plasmid encode antisense regulators, Sok and flmB, that repress Hok and flmA production, respectively (Morsey, M A Supra, 1999).

While it is possible that the antibiotic resistance marker may be replaced with a natural or engineered regulatory RNA, application of such a system to plasmid maintenance has not been reported in the art. While the Hok Sok and flmA flmB systems are actual plasmid maintenance systems, they are not ideal for incorporation into a therapeutic plasmid due to the required presence of a toxin gene on the plasmid.

Morsey; M A, Supra, 1999 discussed in theoretical terms the separation of toxin and antitoxin through construction and selection of plasmids containing only the hok or flmB antisense regulators to repress chromosomally expressed sok or flmA toxin respectively, but the construction of such plasmids was not disclosed. pLac-expressed RNA-OUT from a plasmid only weakly repressed expression of a single copy integrated pR-RNA-IN-lacZ construct. Repression was not observed with increased gene dosage of the pR RNA-IN-lacZ fusion (Jaenecke S, de Lorenzo V, Timmis K N, Diaz E. 1996. *Molec. Microbiol.* 21: 293-300). While this demonstrates that the RNA-IN, RNA-OUT system can be used to obtain some level of regulation of a heterologous chromosomal gene, it does not demonstrate sufficient repression for use of this system for plasmid selection and maintenance. We disclose herein novel compositions and methods to use the RNA-IN RNA-OUT system for plasmid selection, maintenance, and production.

The kanamycin resistance marker in NTC7382 was replaced with a regulatory RNA based selectable marker (the IS10 RNA-OUT antisense RNA). This RNA hybridizes to the RNA-IN RNA, and reduces translation of the downstream IS10 transposase gene (FIG. 19).

As disclosed herein, a counterselectable marker (sacB; *Bacillus subtilis* levansucrase) was expressed under the control of the RNA-IN promoter and leader (FIG. 20) and was integrated into the chromosome of DH5α. Expression of sacB was determined to be constitutive since cells containing sacB encoded levansucrase were killed in presence of sucrose. Translation of SacB from this RNA was designed to be repressed in the presence of the antisense regulator RNA-OUT (FIG. 21). RNA-OUT was cloned into the pDNAVACC Ultra vector, in place of the kanR gene by replacement of the DraIII KpnI cassette (FIG. 21). RNA-OUT was expressed from the plasmid, and repressed expression of the chromosomally integrated counterselectable marker SacB controlled by RNA-IN. This allowed antibiotic free selection in the presence of sucrose on solid and liquid media.

1) Phage λ Attachment Site Integration Vectors:

Replication incompetent plasmids can be site specifically integrated into the genome at bacteriophage attachment sites utilizing bacteriophage recombinase expressing plasmids. Such systems, to allow integration at various bacteriophage attachment sites have been developed (Haldimann A, Wanner B L, 2001, *J. Bacteriol.* 183: 6384-6393) and are generally available (*E. coli* stock center, Yale N H). These plasmids and methods are included herein by reference. For example, integration of a gene at the Phage lambda attachment site requires cloning a gene to be expressed into a modified integration plasmid such as pCAH63-CAT. The pCAH63-CAT vector was constructed by ligating the bacteriophage lambda attachment site-ori-R-chlorR-rgnB containing DNA fragment of pCAH63 (2.2 kb NheI/PstI DNA fragment) with a 350 bp NheI/PstI tL3 containing DNA fragment from pAH81 (both vectors are described in Haldiman and Wanner, Supra, 2001 and were obtained from the *E. coli* stock center, Yale N H). The resultant pCAH63-CAT plasmid contains the R6K conditional replication origin (which requires engineered pir+ host cells such as BW23474 for propagation; the origin is non functional in DH5α) a multiple cloning site, a chloramphenicol resistance marker (chlorR) and the lambda attachment site. The plasmid is integrated into the phage lambda attachment site using the pINT-ts helper plasmid (ampicillin resistant, temperature sensitive R plasmid replicon; this plasmid is lost at 42° C.) that encodes a heat inducible phage lambda integrase. Transformation of DH5a containing the pINT helper with the pCAH63-CAT derivative plasmid to be integrated results in integration of the pCAH63-CAT plasmid into the genome at the phage lambda attachment site; recombinants are selected with chlorR and integration verified using PCR as described in Haldimann and Wanner Supra, 2001.

2) pCAH63-CAT RNA-IN-SacB (p5/6 5/6)

All cloning was performed in BW23474 cell line with selection on chloramphenicol. All clones were sequence verified. pCAH63-CAT vector was digested with PstI/BamHI and the linear fragment purified (F1). The sacB gene was PCR amplified from the pSIREN-DNR vector using following primers (SEQ ID NO: 7)
SacBF01: ctccag<u>cacctgc</u>ctatCAAGatgaacatcaaaaagtttgc aaaacaagc - 5' end of gene (SEQ ID NO: 8)
SacBR01: cgtgag<u>cacctgc</u>aacgGATCatatttgttaactgttaatt gtccttg - 3' end of gene The 1.4 kb PCR product was digested with AarI (underlined, with sticky ends bolded in primer sequences above) and the linear fragment purified (F2).

A constitutive promoter P5/6 5/6-RNA-IN leader sequence was made using synthetic primers as follows.

The following primer pairs were annealed to generate F3 (P5/6 5/6 promoter=5/6 identity to consensus for both −35 and −10 promoter boxes):

(SEQ ID NO: 9)
RNA-INF02: ggt<u>agcacat</u>cttgtcatatgatagaatggtttcgccaa aaatcaataatcagacaa (SEQ ID NO: 10)
RNA-INR02: cttgttgtctgattattgattttggcgaaaccattcta tcatatgacaagatgtgtgtctacctgca The P5/6 5/6 promoter −35 (double underlined) and −10 (double underlined, bold) regions are indicated in the RNA-INF02 primer. The 3 fragments (F1, F2 and F3) were ligated, and transformed into the BW23474 cell line. Recombinants [pCAH63-CAT RNA-1N-SacB (p5/6 5/6)] were selected on choramphenicol, correct clones identified by restriction digestion, and verified by sequencing with tL3-r and rgnB-f sequencing primers (Haldimann and Wanner Supra, 2001).

3) pCAH63-CAT RNA-IN-SacB (P5/6 6/6)

To increase expression of RNA-IN from the above P5/6 5/6 construct, a promoter mutation was introduced that increased promoter activity (P5/6 6/6 has a single base change from P5/6 5/6 that increases promoter strength to 6/6 match with −10 Pribnow box, by changing the TAGAAT sequence to TATAAT). The pCAH63-CAT RNA-1N-SacB (p5/6 5/6) plasmid from above was PCR amplified using the following primers:

(SEQ ID NO: 11)
6/6-10F01: ctccag<u>cacctgc</u>ctatTGGTttcgccaaaaatcaataa tcagacaac (SEQ ID NO: 12)
6/6-10R01: cgtgag<u>cacctgc</u>aacgACCATT<u>A</u>TATCATATGACAAGA

TGTGTGTCTAC

The single base change from C to A is double underlined in the 6/6-10R01 primer (will make G to T change in −10 forward sequence). The 4 kb PCR product was digested with AarI (underlined in primers, bold bases are complementary sticky ends) and the linear fragment purified and ligated to itself. The BW23474 cell line was transformed and choramphenicol resistant colonies selected and correct clones [pCAH63-CAT RNA-IN-SacB (p5/6 6/6)] identified by restriction digestion. The recombinant plasmid (FIG. 20) was sequenced with rgnB-f to confirm the promoter change.

The plasmid was integrated into DH5a and the cell line (RNA-IN-SacB) confirmed by PCR using P1-P4 primers (Haldimann and Wanner Supra, 2001). RNA-IN-SacB did not grow on LB (no NaCl) +6% sucrose plates. This demonstrates that the novel combination of a constitutive promoter expressing RNAI-IN and SacB can be utilized to create a strain constitutively producing sacB, which prevents growth of the cell line on sucrose containing plates.

4) pDNAVACCUltra-P5/6,4/6$_{RBS}$-EGFP (RNA-OUT)

A fluorescent RNA-OUT plasmid was created. The pDNAVACCUltra-P5/6,5/6$_{RBS}$-EGFP plasmid (expresses EGFP constitutively) was digested with DraIII/KpnI and the linear vector (2029, 1015) purified. The following 2 RNA-OUT primers were annealed. These produce an annealed RNA-OUT fragment that is compatible with DraIII and KpnI (FIG. 21).

(SEQ ID NO: 13)
RNA-OUTF01:
gtggtagaattggtaaagagagtcgtgtaaaatatcgagttcgcacatct tgttgtctgattattgattttggcgaaaccatttgatcatatgacaaga tgtgtatctacctttaacttaatgattttgataaaaatcattaggtac (SEQ ID NO: 14)
RNA-OUTR01:
ctaatgatttttatcaaaatcattaagttaaggtagatacacatcttgtc atatgatcaaatggtttcgccaaaaatcaataatcagacaacaagatgtg cgaactcgatattttacacgactctctttaccaattctaccacaac These produce an annealed RNA-OUT fragment that is compatible with DraIII and KpnI (FIG. 21; SEQ ID NO: 15).

The annealed primers were ligated into the vector, and transformed into the RNA-IN-sacB integrated cell line from step 3 above. Colonies were selected on LB (no NaCl) +6% sucrose and plasmid from two fluorescent colonies were sequence verified as correct. Transformation of sequence-verified pDNAVACCUltra-P5/6,4/6$_{RBS}$-EGFP (RNA-OUT) plasmid into RNA-IN-SacB competent cells was performed; all recovered colonies after sucrose selection were fluorescent (i.e. 100% of recovered cells contained the plasmid).

5) RNA-OUT DNA Vaccine Plasmid Construction

The RNA-OUT selectable marker was substituted for the kanamycin resistance gene in a DNA vaccine plasmid as follows. The RNA-OUT cassette was excised from pDNAVACCUltra-P5/6,4/6$_{RBS}$-EGFP (RNA-OUT) using DraIII/XbaI (154 bp) and cloned in a 3 fragment ligation with DraIII-SalI and SalI/XbaI fragments from a target DNA vaccine plasmid. Correct recombinants will have the three fragments ligated together. The ligation was transformed into serial diluted Z-competent cells (Zymo Research, Orange, C A) of the RNA-IN-SacB cell line and the transformations plated on LB (no NaCl) +6% sucrose plates. Colonies from each transformation were screened for insert. 8/10 recovered colonies from the undiluted Z competent cells were correct, as were 719 from the 1:10 diluted competent cells, and 2/2 from the 1:100 diluted competent cells. Similar results were obtained with a second independent ligation reaction for a different construct. Collectively, these results demonstrate that RNA-IN containing plasmids can be surprisingly easily selected from ligation reactions on LB Sucrose plates, and that the selection is robust.

A construct was made with the RNA-OUT cassette in the opposite orientation (RNA-OUT-REV) in the vector. Correct colonies were recovered as described above. This demonstrates that the RNA-OUT cassette can function for sucrose selection in either orientation in the vector.

Vectors were constructed with either the influenza H5 hemagglutinin gene (HA), SEAP or EGFP reporter genes in the RNA-OUT vector. As well, versions containing various pol III transcribed immunostimulatory RNAs (eRNAs) that activate the RIG-I and MDA5 receptor were constructed. Over 20 different DNA vaccine vectors were constructed with the RNA-OUT sucrose selection method. This demonstrates the surprising robustness and general utility of the RNA-OUT sucrose selection methodology. The sequence of the NTC8382-41H-HA vector (FIG. 1; RNA-OUT equivalent of kanR NTC7382 41H-HA) is given in (SEQ ID NO: 16).

6) RNA-OUT DNA Vaccine Expression

Antigen expression, and RIG-I activation, after lipofectamine 2000 transfection of HEK293 cells (human) was determined for RNA-OUT plasmids, compared to control kanR plasmids as follows.

The vectors were tested for RIG-I activation in HEK293 cells using the one step assay as described in Example 4. For EGFP and HA (Section 7 below) protein expression analysis, the EGFP or HA RNA-OUT or KanR plasmids (0.4 ug each well) were transfected as described in Example 4 (without RIG-I or pl25luc and control EGFP plasmid), and total cellular protein 48 hrs post transfection assayed by FLX800 microplate fluorescence reader (EGFP) or Western blot analysis (HA).

No difference was observed between RNA-OUT plasmids and the corresponding kanR plasmid (otherwise same backbones) for EGFP (Table 4) or HA (Section 7 below) expression or RIG-I activation (FIG. 17).

This demonstrates that the presence of RNA-OUT in the vector backbone does not adversely affect eukaryotic functions of the plasmid, for example, NTC7382 promoter-driven antigen expression or Pol III driven immunostimulatory RNA expression.

7) RNA-OUT Influenza DNA Vaccine Vectors

Influenza H5 HA 'bird flu' eRNA RNA-OUT vector were made, by simple swapping of the eRNA region into the plasmid backbone using flanking sites common to all the vectors, such as NotI-AflIII, NheI-AflIII, NotI-ApaLI, NheI-ApaLI, NotI-DraIII, or NheI-DraIII fragment swaps and the influenza gene using SalI-BglII fragment swaps.

eRNA bird flu vectors (H5 HA vectors) were tested for immunostimulation as described in Example 4. Potent activation of murine and human RIG-I, and human MDA5 was observed. This demonstrates that eRNA activation is not antigen dependent or vector dependent. Western blot analysis was performed on protein extracts (as described for EGFP in Section 6 above) using rabbit anti-HA H5N1 rabbit IgG (eEnzyme, Gaithersburg, Md.) primary antibody, and the amplified alkaline phosphatase immuno-blot assay kit and A P conjugate substrate kit (Biorad, Hercules, Calif.). As expected, the HA protein was expressed in transformed cell lysates as mostly uncleaved protein, while an alternative 1203 HA, with the basic cleavage site intact, was mostly cleaved protein. Expression levels of HA from NTC7382 promoter containing vectors (Kanamycin resistance or RNA-OUT) were similar, and higher than CMV or SV40-CMV vectors.

8) RNA-OUT DNA Vaccine Production

The RNA-OUT sequence has no repetitive sequences that may be toxic or unstable in *E. coli*, so effects on quality in fermentation production were not expected. To verify this, an RNA-OUT-HA vector was tested for fermentation productivity. An exponential, inducible fed-batch fermentation was performed using the high yield plasmid production process disclosed in Carnes A E, Williams M. 2006. World Patent Application WO2006023546. This fermentation, RF117, was carried out in a 7.5 L fermentor with an RNA-OUT-41H-HA plasmid in *E. coli* strain DH5α. The fermentation media contained 0.5% sucrose for plasmid selection since it was determined that >0.5% sucrose in fermentation media is growth inhibitory to the parent plasmid-less strain. The temperature was initially controlled at 30° C. The temperature set point was increased to 42° C. after 27 hours to increase plasmid yield. The culture was harvested after 39 hours of total fermentation time (11 hr plasmid induction at 42° C.). The culture had a final cell density of 90 $OD_{600}$. The plasmid yield from this fermentation was 1213 mg/L (FIG. 22) and the plasmid was of a high quality (supercoiled monomer) with no detected replication intermediates or aberrant bands. This yield is typical for kanR based pDNAVACCUltra derived vectors. This demonstrates that inclusion of RNA-OUT in the vector backbone has no detrimental effect on plasmid production yield or quality.

8) RNA-OUT Autolytic Production Cell Line (NTC3016)

For general application to production of a variety of plasmids, it is preferable for the production cell line to not have plasmid replication origins (e.g. R6K replication origin) in the chromosome. The pCAH-63 CAT RNA-IN-SacB (P5/6 6/6) backbone was amplified by PCR to delete this replication origin, ligated to form a circle, and integrated using the pINT-ts plasmid as described below.

The pCAH63-CAT RNA-IN-SacB (P5/6 6/6) plasmid was PCR amplified to delete the R6K replication origin using the following primers (FIG. 20).

```
                                          (SEQ ID NO: 17)
R6KdR01:
ctccagcacctgcttttACACaggaacacttaacggctgacatg
```

```
                                          (SEQ ID NO: 18)
R6KdF01:
cgtgagcacctgcaactGTGTtgaactgctgatcttcagatcctctac
```

The 3.5 kb linear product was DpnI digested (to eliminate parent plasmid), AarI digested (underlined in primers) to create compatible sticky ends (bolded in primer), Qiaquick purified, and ligated (to make exonuclease resistant circles for integration). The ligation was electroporated into pINTts lambda integration plasmid containing NTC3012 cell line (autolytic production host described in copending application Carnes and Williams, U.S. patent application U.S. 60/931,465) and colonies were selected with chloramphenicol. The cell line (NTC3016) was confirmed with PCR using normal P1-P4 primers (Haldimann and Wanner Supra, 2001); these primer sites are retained in the amplified minicircle vector.

Several RNA-OUT plasmids have been successfully transformed and propagated in the NTC3016 cell line, without toxicity or interference with autolysis. A fermentation yield of 1.1 gm plasmid/liter culture after 10.5 hr induction was obtained with the RNA-OUT NTC8382-41H-HA plasmid (FIG. 1) in the NTC3016 cell line (RF137). This demonstrates that the RNA-OUT plasmid is compatible with autolytic host strains and NTC fermentation process.

Example 8: eRNA-M

The 16.5 kb human mitochondrial genome encodes 13 polypeptides, 22 tRNAs and 2 rRNAs. The mitochondrial genetic code is different than the nuclear code, so nuclear genes are not correctly translated in the mitochondria. A 1 kb noncoding region (the mitochondrial R-region) acts as a bidirectional promoter for the synthesis of polycistronic RNA for the heavy and light strands as well as the replication origin for the heavy chain. Transcription requires negative supercoiling (Buzan J M, Low R L. 1988 *Biochem. Biophys. Res. Commun.* 152: 22), as is the case for *E. coli*-produced plasmid DNA. The mitochondrial promoter does not function in the nucleus nor does it inhibit the activity of weak or strong pol II promoters (Sewards R, Wiseman B, Jacobs H T. 1994. *Mol. Gen. Genet.* 245: 760).

Rat mitochondria have been shown to be naturally competent for DNA transfection; internalized DNA is functionally expressed (Koulintchenko M, Temperley R J Mason P A, Dietrich A, and Lightowlers, R N 2006. *Human Molec Genet* 15: 143). Studies of plasmid fate during gene transfer have not reported plasmid transit to the mitochondria. However, electroporation is used to introduce plasmid DNA into isolated mitochondria (Collombet J M, Wheeler V C, Vogel F, Coutelle C. 1997. *J Biol Chem.* 272: 5342) wherein the plasmid is expressed (Yoon Y G, Koob, M D. 2003. *Nucl. Acids Res.* 31: 1407-1415.). The mitochondrial genome is also underrepresented for CpG (Cardon, L R, Burge C, Clayton D A, Karlin S. 1994 *Proc Natl. Acad. Sci USA* 91: 3799-3803) which the inventor speculates may indicate that unmethylated mitochondrial DNA is accessible to TLR9 (which recognizes unmethylated CpG DNA and induces innate immune responses).

To test this hypothesis, a NTC7382-41H-M plasmid was constructed. M refers to insertion of the mitochondrial R region. To evaluate in mice, the murine mitochondrial R-region was used. The murine mouse mitochondrial R-region was PCR amplified using murine DNA and the following primers:

```
                                      (SEQ ID NO: 19)
10110701: TGCGCAagtacataaatttacatagtacaacagtac (SEQ ID NO: 20)
10110702: TGCGCAttgttaatgtttattgcgtaatagagtatga
```

The TGCGCA bolded sites are FspI restriction sites added adjacent to the R region to allow transfer to alternative vectors. The 883 bp PCR product was kinased using T4 kinase and cloned into the DraIII site of NTC7382-41H HA vector [the vector was cleaved with DraIII, the sticky ends removed by T4 DNA polymerase exonuclease, and the fragment treated with calf intestinal phosphatase (CIP)] to create the NTC7382-41H-M HA vector (FIG. 23). The clone was sequence verified. The R region in this clone is in orientation 2 (10110702 primer immediately adjacent to pUC origin). No effect on plasmid propagation, stability or yield was detected. SEAP and EGFP expressing derivatives were made by swapping out the HA gene (SalI-BglII fragment swaps). No effect on EGFP expression in HEK293 cells was observed.

Example 9: eRNA-M In Vivo Analysis

NTC7382 41H-HA and NTC7382-41H-M-HA FIG. 23) and NTC8382-41H-HA (FIG. 21) vaccines were tested for immunogenicity (8 mice per group) in vivo versus control NTC7382-SEAP vector. Immunogenicity was compared to expression level (3 mice per group, using corresponding vectors containing SEAP rather than HA). In both studies, 3 µg HA plasmid was injected intra-muscular (I M, quadriceps) of female BALB/c mice (6-8 weeks old) in a single dose (day 0) prior to electroporation (E P) using the Med-Pulser® system (Innovio Biomedical, San Diego Calif.) using a 2 needle array (27 G), 4 mm apart, 2×60 ms pulses at 50 mA. Serum samples were taken and tested for SEAP or anti-HA IgG response. SEAP levels were determined using the Phospha-light SEAP Reporter Gene Assay System from Applied Biosystems (Foster City, Calif.) according to the manufacturer's instructions. Anti-HA specific total IgG, IgG2a, and IgG1 levels were determined by standard ELISA assay using plates coated with Nature Technology Corporation produced recombinant *E. coli* produced A/Vietnam/1203/2004 HA2 domain as described in Example 5. The results are summarized in Table 5 and demonstrate 1) the antibiotic free NTC8382 backbone is equivalent or superior to the NTC7382 backbone for expression and immunogenicity and; 2) the NTC7382-41H-M backbone improved immune response to HA when compared with parent NTC7382-41H backbone. Given that the improved immune response to HA with the NTC7382-41H-M backbone compared to the parent backbone did not correlate with improved expression of SEAP, this demonstrates that inclusion of the murine mitochondrial R-region (M) in the backbone improved vector immunostimulation. While not limiting the application of embodiments of the invention, and not taught in the art, it is speculated that the improved immunostimulation observed with a plasmid incorporating the murine mitochondrial R-region was due to one or more of the possible mechanisms. When delivered by electroporation (and other modalities) a mitochondrial R-region plasmid may:

1) Transfect both the mitochondria and nucleus. While antigen expression in the mitochondria would not be expected to occur, the plasmid may be transcribed (both strands) in the mitochondria and be replicated (one strand) in the mitochondria due to the R-region.

2) Transcription would result in formation of immunostimulatory ssRNA (e.g. highly structured bacterial origin, optionally engineered immunostimulatory RNA) and dsRNA (annealed bidirectional transcripts). Significantly, since zero or limited numbers of tRNA structures are present in the transcribed strands of the plasmids, the two strands should not be extensively cleaved, and would anneal into a very large immunostimulatory dsRNA.

3) Replication would result in immunostimulatory (CpG rich) ssDNA.

4) Immunostimulatory RNA and DNA may improve immunostimulation of the vaccine through cytoplasmic DNA receptors (e.g. DAI) or cytoplasmic RNA receptors RIG-I, MDA5, PKR, or OAS, or endosomal receptors TLRs 3 (dsRNA) 7, 8 (ssRNA) or 9 (CpG dsDNA).

5) Transcription, replication, and/or translation (aberrant) may also lead to activation of mitochondrial apoptotic pathways. Apoptosis may improve vaccine performance.

Mitochondrial promoters show some species specificity, since human and mouse mitochondrial transcription machineries do not recognize the heterologous species (Gaspari, M, Falkenberg M, Larsson N G, Gustafs son C M. 2004. *EMBO J* 23: 4606-4614) so for human or animal vaccination it may be critical to determine appropriate mitochondrial promoter for use. Such modifications to the vector and determination of appropriate promoters can be accomplished by investigators skilled in the art of cloning (i.e. selecting homologous fragments corresponding to the mitochondrial R region amplified with the primers disclosed in Example 8) and immunological testing.

TABLE 5

NTC7382 41H-HA and NTC7382-41H-M-HA and NTC8382-41H-HA in vivo expression and immunogenicity++

| Backbone | 4 day SEAP (ng/mL) | 7 day SEAP (ng/mL) | 14 Day SEAP (ng/mL) | 21 day anti-HA2 IgG (total) (Abs 1/12,500) | 21 day anti-HA2 IgG2a (Abs 1/500) | 21 day anti-HA2 IgG1 (Abs 1/500) | % sero-converted (1/2500) |
|---|---|---|---|---|---|---|---|
| NTC7382-41H | 216 ± 147 | 300 ± 121 | 158 ± 43 | 0.173 ± 0.101 | 0.318 ± 0.229 | 0.140 ± 0.069 | 6/8 |
| NTC7382-41H-M | 109 ± 61 | 375 ± 376 | 215 ± 147 | 0.335 ± 0.264 | 0.706 ± 0.475 | 0.517 ± 0.439 | 8/8 |
| NTC8382-41H | 241 ± 71 | 305 ± 83 | 243 ± 43 | 0.302 ± 0.134 | 0.483 ± 0.236 | 0.377 ± 0.384 | 7/8 |
| Control† | | | | 0.066 ± 0.010 | 0.079 ± 0.023 | 0.086 ± 0.020 | 1/8 |

†All day 0 SEAP undetected. For HA, NTC7382-SEAP was the negative control plasmid
++Results presented as average ± standard deviation

CONCLUSIONS, RAMIFICATIONS AND SCOPE OF THE INVENTION

Thus, the reader will see that the vector embodiments of the invention provide for a rationale approach to optimization of genetic immunization or gene therapy, through use of the improved NTC7382 promoter, RNA based selectable marker, and/or vector encoded interferon inducing eRNA compositions.

While the above description contains many specifications, these should not be construed as limitations on the scope of the invention, but rather should be viewed as an exemplification of preferred embodiments thereof. Many other variations are possible. For example, MDA5, RIG-I and PKR inhibiting immunostimulatory RNA elements may be combined with repressor RNA elements that encode shRNAs to inhibit LGP2 (a repressor of RIG-I and MDA5 immunostimulation) ADAR and/or inhibitors of RIG-I or downstream IPS-1 signaling pathway. This would maximize immunostimulation while preventing PKR mediated inhibition of antigen expression. Other inhibitor RNA elements could be included to induce apoptosis selectively in non-immune cells, to increase antigen cross presentation, or influence $T_H1$ versus $T_H2$ bias. As well, the eRNA element embodiments of the invention could be incorporated into alternative gene delivery vehicles, including viral (e.g. alphavirus, poxvirus, lentivirus, retrovirus, adenovirus, adenovirus related virus, etc) and nonviral (e.g. plasmid, midge, transcriptionally active PCR fragment, minicircles, bacteriophage, etc) vectors. As well, vectors or DNA fragments containing immunostimulatory eRNA sequences (with or without a codelivered antigen gene) may be used to increase anti-viral, anti-tumor and or antibacterial activity in a patient, through induction of type 1 interferon production. In this manner, immunostimulatory RNA sequences may be used in treatment therapies to induce production of natural type 1 interferon's.

Accordingly, the scope of the invention should be determined not by the embodiments illustrated, but by the appended claims and their legal equivalents.

I claim:

1. A method for inducing an adaptive immune response in a mammal comprising the steps of:
   a. providing a vector comprising a first RNA element comprising a VARNAI RNA component, and a second RNA element comprising an RIG-I activating immunostimulatory RNA element of 30-200 basepairs operably linked to a U6 RNA polymerase III promoter, and at least one gene encoding a protein or peptide antigen; and
   b. delivering said vector to said mammal under conditions such that said antigen is expressed and said first RNA element and said second RNA element are expressed and induce an adaptive immune response to said antigen.

2. The method of claim 1, wherein said vector is a non-viral vector.

3. The method of claim 1, wherein said imunostimulatory RNA element of 30-200 basepairs is an U6 RNA Polymerase III promoter-expressed hairpin, double-stranded immunostimulatory RNA element.

4. The method of claim 1, wherein said immunostimulatory RNA element of 30-200 base pairs operably linked to a U6 RNA polymerase III promoter further comprises a tRNA RNA polymerase promoter arranged in opposite orientation to said U6 RNA polymerase III promoter, such that transcription of said RNA element is convergent.

5. The method of claim 1, whereby said adaptive immune response is increased, as compared to a vector lacking the combination of VARNAI and at least one additional immunostimulatory RNA element, without reducing antigen expression.

6. A method for inducing an adaptive immune response in a mammal comprising the steps of:
   a. providing first and second vectors, said first vector comprising i) a first RNA element comprising a VARNAI RNA component, and ii) a gene encoding a protein or peptide antigen, said second vector comprising a second RNA element comprising an RIG-I activating immunostimulatory RNA element of 30-200 basepairs operably linked to a U6 RNA polymerase III promoter, and
   b. delivering said first and second vectors to said mammal under conditions such that said antigen is expressed, and said first RNA element and said second RNA element are expressed and induce an adaptive immune response to said antigen.

7. The method of claim 6, whereby said adaptive immune response is increased, as compared to vector (s) lacking the combination of VARNAI and at least one additional immunostimulatory RNA element, without reducing antigen expression.

8. A method for inducing type 1 interferon production in a mammal comprising the steps of:
   a. obtaining a vector comprising a first RNA element comprising a VARNAI RNA component, and a second RNA element comprising an RIG-I activating immunostimulatory RNA element of 30-200 base pairs operably linked to a 136 RNA polymerase III promoter, wherein said immunostimulatory RNA element of 30-200 base pairs operably linked to a U6 RNA polymerase III promoter further comprises a tRNA RNA polymerase III promoter arranged in opposite orientation to said U6 RNA polymerase III promoter, such that transcription of said RNA element is convergent; and
   b. delivering said vector to said mammal under conditions such that type 1 interferon production is induced.

9. The method of claim 8, whereby said type 1 interferon production increases anti-viral, anti-tumor or antibacterial activity in said mammal.

10. The method of claim 8, whereby said type 1 interferon production is increased, as compared to a vector lacking the combination of VARNAI and at least one additional immunostimulatory RNA element.

11. The method of claim 8, wherein said imunostimulatory RNA element of 30-200 basepairs is an U6 RNA Polymerase III promoter-expressed hairpin, double-stranded immunostimulatory RNA element.

12. The method of claim 2, wherein said non-viral vector is a plasmid vector.

* * * * *

SEQUENCE LISTING

```
<160> NUMBER OF SEQ ID NOS: 20

<210> SEQ ID NO 1
<211> LENGTH: 33
<212> TYPE: DNA
<213> ORGANISM: Artificial Sequence
<220> FEATURE:
<223> OTHER INFORMATION: DNA expression cassette containing an expressed
      RNA sequence - eRNAs 23 and 24

<400> SEQUENCE: 1
gacaacgggg gagtgctcct ttttggctt cct                                  33

<210> SEQ ID NO 2
<211> LENGTH: 132
<212> TYPE: DNA
<213> ORGANISM: Artificial Sequence
<220> FEATURE:
<223> OTHER INFORMATION: DNA expression cassette containing an expressed
      RNA sequence - eRNA11

<400> SEQUENCE: 2
aacgttaaaa aacaggtcct ccccatactc tttcattgta cacaccgcaa gctcgacaat      60
catcggattg aagcattgtc gcacacatct tccacacagg atcagtacct gctttcgcta    120
accaaggctt tt                                                        132

<210> SEQ ID NO 3
<211> LENGTH: 122
```

```
<212> TYPE: DNA
<213> ORGANISM: Artificial Sequence
<220> FEATURE:
<223> OTHER INFORMATION: DNA expression cassette containing an expressed
      RNA sequence - eRNA11A

<400> SEQUENCE: 3
aacgttaaaa aacaggtcct ccccatactc tttcattgta cacaccgcaa gctcgacaat      60
catcggattg aagcattgtc gcacacatct tccacacagg atcagtacct gctttcgctt    120
tt                                                                   122

<210> SEQ ID NO 4
<211> LENGTH: 136
<212> TYPE: DNA
<213> ORGANISM: Artificial Sequence
<220> FEATURE:
<223> OTHER INFORMATION: DNA expression cassette containing an expressed
      RNA sequence - eRNA11B

<400> SEQUENCE: 4
aacgttaaaa aacaggtcct ccccatactc tttcattgta cacaccgcaa gctcgacaat      60
catcggattg aagcattgtc gcacacatct tccacacagg atcagtacct gctttcggaa    120
ttcaaccaag gctttt                                                    136

<210> SEQ ID NO 5
<211> LENGTH: 116
<212> TYPE: DNA
<213> ORGANISM: Artificial Sequence
<220> FEATURE:
<223> OTHER INFORMATION: DNA expression cassette containing an expressed
      RNA sequence - eRNA4li

<400> SEQUENCE: 5
aacgttaaaa aacaggtcct ccccatactc tttcattgta cacaccgcaa gctcgacaat      60
catcggattg aagcattgtc gcacacatct tccacacagg atcagtacct gctttt        116

<210> SEQ ID NO 6
<211> LENGTH: 1136
<212> TYPE: DNA
<213> ORGANISM: Artificial Sequence
<220> FEATURE:
<223> OTHER INFORMATION: chimeric promoter comprising the CMV enhancer-
      CMV promoter-HTLV R-U5-synthetic rabbit beta globin 3' intron
      acceptor -exon 2-SRF protein binding site-kozak sequence, with or
      without an upstream SV40 enhancer (NTC7382 promoter)

<400> SEQUENCE: 6
ccattgcata cgttgtatcc atatcataat atgtacattt atattggctc atgtccaaca      60
ttaccgccat gttgacattg attattgact agttattaat agtaatcaat tacgggtca    120 ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca gtacgccccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccaccccat tgacgtcaat    540
gggagtttgt tttggcacca aaatcaacgg gactttccaa aatgtcgtaa caactccgcc    600
```

```
ccattgacgc aaatgggcgg taggcgtgta cggtgggagg tctatataag cagagctcgt      660
ttagtgaacc gtcagatcgc ctggagacgc catccacgct gttttgacct ccatagaaga      720
caccgggacc gatccagcct ccgcggctcg catctctcct tcacgcgccc gccgccctac      780
ctgaggccgc catccacgcc ggttgagtcg cgttctgccg cctcccgcct gtggtgcctc      840
ctgaactgcg tccgccgtct aggtaagttt aaagctcagg tcgagaccgg gcctttgtcc      900
ggcgctccct tggagcctac ctagactcag ccggctctcc acgctttgcc tgaccctgct      960
tgctcaactc tagttctctc gttaacttaa tgagacagat agaaactggt cttgtagaaa     1020
cagagtagtc gcctgctttt ctgccaggtg ctgacttctc tcccctgggc ttttttcttt     1080
ttctcaggtt gaaagaaga agacgaagaa gacgaagaag acaaaccgtc gtcgac          1136

<210> SEQ ID NO 7
<211> LENGTH: 50
<212> TYPE: DNA
<213> ORGANISM: Artificial Sequence
<220> FEATURE:
<223> OTHER INFORMATION: Primer for amplifying the sacB gene (SACBF01)

<400> SEQUENCE: 7
ctccagcacc tgcctatcaa gatgaacatc aaaaagtttg caaaacaagc                  50

<210> SEQ ID NO 8
<211> LENGTH: 49
<212> TYPE: DNA
<213> ORGANISM: Artificial Sequence
<220> FEATURE:
<223> OTHER INFORMATION: Primer for amplifying the sacB gene (SACBR01)

<400> SEQUENCE: 8
cgtgagcacc tgcaacggat ccttatttgt taactgttaa ttgtccttg                   49

<210> SEQ ID NO 9
<211> LENGTH: 60
<212> TYPE: DNA
<213> ORGANISM: Artificial Sequence
<220> FEATURE:
<223> OTHER INFORMATION: Primer for making P5/6 5/6 -RNA-IN leader
      sequence (RNA-INF02)

<400> SEQUENCE: 9
ggtagacaca catcttgtca tatgatagaa tggtttcgcc aaaaatcaat aatcagacaa       60

<210> SEQ ID NO 10
<211> LENGTH: 68
<212> TYPE: DNA
<213> ORGANISM: Artificial Sequence
<220> FEATURE:
<223> OTHER INFORMATION: Primer for making P5/6 5/6 -RNA-IN leader
      sequence (RNA-INR02)

<400> SEQUENCE: 10
cttgttgtct gattattgat ttttggcgaa accattctat catatgacaa gatgtgtgtc       60
tacctgca                                                               68

<210> SEQ ID NO 11
<211> LENGTH: 48
<212> TYPE: DNA
<213> ORGANISM: Artificial Sequence
<220> FEATURE:
<223> OTHER INFORMATION: Primer for amplifying the pCAH63-CAT RNA-IN-
      SacB (p5/6 5/6) plasmid (6/6-10F01)
```

<400> SEQUENCE: 11
ctccagcacc tgcctattgg tttcgccaaa aatcaataat cagacaac                48

<210> SEQ ID NO 12
<211> LENGTH: 50
<212> TYPE: DNA
<213> ORGANISM: Artificial Sequence
<220> FEATURE:
<223> OTHER INFORMATION: Primer for amplifying the pCAH63-CAT RNA-IN-
      SacB (p5/6 5/6) plasmid (6/6-10R01)

<400> SEQUENCE: 12
cgtgagcacc tgcaacgacc attatatcat atgacaagat gtgtgtctac               50

<210> SEQ ID NO 13
<211> LENGTH: 147
<212> TYPE: DNA
<213> ORGANISM: Artificial Sequence
<220> FEATURE:
<223> OTHER INFORMATION: RNA-OUT primer for producing an annealed RNA-
      OUTfragment that is compatible with DraIII and KpnI (RNAOUTF01)

<400> SEQUENCE: 13
gtggtagaat tggtaaagag agtcgtgtaa aatatcgagt tcgcacatct tgttgtctga    60
ttattgattt ttggcgaaac catttgatca tatgacaaga tgtgtatcta ccttaactta   120 atgatttga taaaaatcat taggtac                                        147

<210> SEQ ID NO 14
<211> LENGTH: 146
<212> TYPE: DNA
<213> ORGANISM: Artificial Sequence
<220> FEATURE:
<223> OTHER INFORMATION: RNA-OUT primer for producing an annealed RNA-
      OUT fragment that is compatible with DraIII and KpnI (RNAOUTR01)

<400> SEQUENCE: 14
ctaatgattt ttatcaaaat cattaagtta aggtagatac acatcttgtc atatgatcaa    60
atggtttcgc caaaaatcaa taatcagaca acaagatgtg cgaactcgat attttacacg   120
actctcttta ccaattctac cacaac                                        146

<210> SEQ ID NO 15
<211> LENGTH: 139
<212> TYPE: DNA
<213> ORGANISM: Artificial Sequence
<220> FEATURE:
<223> OTHER INFORMATION: RNAOUT DraIII to KpnI selectable marker

<400> SEQUENCE: 15
gtagaattgg taaagagagt cgtgtaaaat atcgagttcg cacatcttgt tgtctgatta    60 ttgattttg gcgaaaccat ttgatcatat gacaagatgt gtatctacct taacttaatg   120
attttgataa aaatcatta                                                139

<210> SEQ ID NO 16
<211> LENGTH: 5246
<212> TYPE: DNA
<213> ORGANISM: Artificial Sequence
<220> FEATURE:
<223> OTHER INFORMATION: sequence ofthe NTC8382-4I H-HA vector (RNA-OUT
      equivalent of kanR NTC7382 41H-HA)

<400> SEQUENCE: 16
accgttggtt tccgtagtgt agtggttatc acgttcgcct aacacgcgaa aggtccccgg    60

```
ttcgaaaccg ggcactacaa accaacaacg ttaaaaaaca ggtcctcccc atactctttc    120
attgtacaca ccgcaagctc gacaatcatc ggattgaagc attgtcgcac acatcttcca    180
cacaggatca gtacctgctt tcgcttttaa ccaaggcttt tctccaaggg atatttatag    240
tctcaaaaca cacaattact ttacagttag ggtgagtttc cttttgtgct gtttttttaaa    300
ataataattt agtatttgta tctcttatag aaatccaagc ctatcatgta aaatgtagct    360
agtattaaaa agaacagatt atctgtcttt tatcgcacat taagcctcta tagttactag    420
gaaatattat atgcaaatta accggggcag gggagtagcc gagcttctcc cacaagtctg    480
tgcgaggggg ccggcgcggg cctagagatg gcggcgtcgg atcggccagc ccgcctaatg    540
agcgggcttt tttttcttag ggtgcaaaag gagagcctgt aagcgggcac tcttccgtgg    600
tctggtggat aaattcgcaa gggtatcatg gcggacgacc ggggttcgag ccccgtatcc    660
ggccgtccgc cgtgatccat gcggttaccg cccgcgtgtc gaacccaggt gtgcgacgtc    720
agacaacggg ggagtgctcc ttttggcttc cttccccttc ttccgcttcc tcgctcactg    780
actcgctgcg ctcggtcgtt cggctgcggc gagcggtatc agctcactca aaggcggtaa    840
tacggttatc cacagaatca ggggataacg caggaaagaa catgtgagca aaaggccagc    900
aaaaggccag gaaccgtaaa aaggccgcgt tgctggcgtt tttccatagg ctccgccccc    960
ctgacgagca tcacaaaaat cgacgctcaa gtcagaggtg gcgaaacccg acaggactat   1020
aaagatacca ggcgtttccc cctggaagct ccctcgtgcg ctctcctgtt ccgaccctgc   1080
cgcttaccgg atacctgtcc gcctttctcc cttcgggaag cgtggcgctt tctcatagct   1140
cacgctgtag gtatctcagt tcggtgtagg tcgttcgctc caagctgggc tgtgtgcacg   1200
aaccccccgt tcagcccgac cgctgcgcct tatccggtaa ctatcgtctt gagtccaacc   1260
cggtaagaca cgacttatcg ccactggcag cagccactgg taacaggatt agcagagcga   1320
ggtatgtagg cggtgctaca gagttcttga agtggtggcc taactacggc tacactagaa   1380
gaacagtatt tggtatctgc gctctgctga agccagttac cttcggaaaa agagttggta   1440
gctcttgatc cggcaaacaa accaccgctg gtagcggtgg tttttttgtt tgcaagcagc   1500
agattacgcg cagaaaaaaa ggatctcaag aagatccttt gatcttttct acggggtctg   1560
acgctcagtg gaacgaaaac tcacgttaag ggattttggt catgagatta tcaaaaagga   1620
tcttcaccta gatcctttta aattaaaaat gaagttttaa atcaatctaa agtatatatg   1680
agtaaacttg gtctgacagt taccaatgct taatcagtga ggcacctatc tcagcgatct   1740
gtctatttcg ttcatccata gttgcctgac tcctgcaaac cacgttgtgg tagaattggt   1800
aaagagagtc gtgtaaaata tcgagttcgc acatcttgtt gtctgattat tgatttttgg   1860
cgaaaccatt tgatcatatg acaagatgtg tatctacctt aacttaatga ttttgataaa   1920
aatcattagg taccctgat cactgtggaa tgtgtgtcag ttagggtgtg gaaagtcccc    1980
aggctcccca gcaggcagaa gtatgcaaag catgcatctc aattagtcag caaccaggtg   2040
tggaaagtcc ccaggctccc cagcaggcag aagtatgcaa agcatgcatc tcaattagtc   2100
agcaaccata gtcccgcccc taactccgcc catcccgccc ctaactccgc ccaggatccg   2160
ctctagatgg ccattgcata cgttgtatcc atatcataat atgtacattt atattggctc   2220
atgtccaaca ttaccgccat gttgacattg attattgact agttattaat agtaatcaat   2280
tacggggtca ttagttcata gcccatatat ggagttccgc gttacataac ttacggtaaa   2340
tggcccgcct ggctgaccgc ccaacgaccc ccgcccattg acgtcaataa tgacgtatgt   2400
```

| | |
|---|---|
| tcccatagta acgccaatag ggactttcca ttgacgtcaa tgggtggagt atttacggta | 2460 |
| aactgcccac ttggcagtac atcaagtgta tcatatgcca agtacgcccc ctattgacgt | 2520 |
| caatgacggt aaatggcccg cctggcatta tgcccagtac atgaccttat gggactttcc | 2580 |
| tacttggcag tacatctacg tattagtcat cgctattacc atggtgatgc ggttttggca | 2640 |
| gtacatcaat gggcgtggat agcggtttga ctcacgggga tttccaagtc tccacccc at | 2700 |
| tgacgtcaat gggagtttgt tttggcacca aaatcaacgg gactttccaa aatgtcgtaa | 2760 |
| caactccgcc ccattgacgc aaatgggcgg taggcgtgta cggtgggagg tctatataag | 2820 |
| cagagctcgt ttagtgaacc gtcagatcgc ctggagacgc catccacgct gttttgacct | 2880 |
| ccatagaaga caccgggacc gatccagcct ccgcggctcg catctctcct tcacgcgccc | 2940 |
| gccgccctac ctgaggccgc catccacgcc ggttgagtcg cgttctgccg cctcccgcct | 3000 |
| gtggtgcctc ctgaactgcg tccgccgtct aggtaagttt aaagctcagg tcgagaccgg | 3060 |
| gcctttgtcc ggcgctccct ggagcctac ctagactcag ccggctctcc acgctttgcc | 3120 |
| tgaccctgct tgctcaactc tagttctctc gttaacttaa tgagacagat agaaactggt | 3180 |
| cttgtagaaa cagagtagtc gcctgctttt ctgccaggtg ctgacttctc tcccctgggc | 3240 |
| ttttttcttt ttctcaggtt gaaaagaaga agacgaagaa gacgaagaag acaaaccgtc | 3300 |
| gtcgacatgg agaaaatagt gcttcttttt gcaatagtca gtcttgttaa aagtgatcag | 3360 |
| atttgcattg gttaccatgc aaacaacagt accgagcaag ttgacacaat catggagaag | 3420 |
| aacgtaacag ttactcacgc ccaagacatc ttggagaaga agcacaacgg caagctgtgc | 3480 |
| gatctagacg gcgtcaaacc cctgatcctg agggactgca gtgtagccgg ctggctgctg | 3540 |
| ggtaacccaa tgtgcgacga attcatcaac gtcccagagt ggagctacat cgtggaaaag | 3600 |
| gctaaccctg tgaacgacct ctgctaccct ggtgacttca acgattacga ggagctgaag | 3660 |
| cacttgctct cccgaattaa tcacttcgag aagattcaaa tcatcccaaa atcttcatgg | 3720 |
| agctcacacg aagccagcct gggcgttagc tctgcctgcc cctaccaggg taagagttcc | 3780 |
| ttcttccgaa atgtcgtgtg gctgataaag aagaacagca cttacccgac aatcaaacga | 3840 |
| agttacaaca ataccaacca ggaggatttg ctggttctct ggggcatcca ccaccctaac | 3900 |
| gacgctgccg agcaaacgaa gctctaccag aacccaacta catacatctc cgtcggaact | 3960 |
| tctacactta atcaaagact cgtccctagg atagcaacgc gcagcaaggt aaacgggcaa | 4020 |
| agtggaagga tggagttctt ctggactatc ctgaagccaa acgacgctat caacttcgaa | 4080 |
| tcaaacggca ctttatcgc cccggagtat gcctataaaa tcgtcaagaa agggg attct | 4140 |
| accatcatga atcagagct tgagtacggc aactgcaata ctaagtgcca gacacctatg | 4200 |
| ggcgcgatca atagcagcat gcccttttcac aatattcatc ctctgactat aggcgaatgc | 4260 |
| ccaaagtacg ttaagtcaaa ccgactcgta ctcgccactg ggctcagaaa tagccctcaa | 4320 |
| agagagtcca gaggattatt tggagctata gcaggtttta tagagggagg atggcaggga | 4380 |
| atggtagatg gttggtatgg gtaccaccat agcaatgagc aggggagtgg gtacgctgca | 4440 |
| gacaaagagt ctacgcagaa ggccatagac ggggttacca acaaggttaa ttctatcatc | 4500 |
| gataagatga acacccaatt tgaggctgtg gccgagagt tcaataacct ggaaagaagg | 4560 |
| atagagaatc tcaacaagaa aatggaggac ggtttcctcg acgtgtggac atacaacgcc | 4620 |
| gagcttctcg tgctgatgga gaacgaacgc actctagact ccacgactc caatgtcaag | 4680 |
| aatctttatg acaaggtgcg gttgcaactt agagacaatg ctaaggagtt ggggaacggt | 4740 |
| tgttttgagt tctaccatag gtgtgataat gagtgcatgg agtctgttcg aaacgggacg | 4800 |

-continued

```
tacgattatc cccagtactc tgaagaggcc cgattgaaaa gagaagaaat aagtggagta    4860
aaattggaat caataggaat ttaccaaata ctgtcaattt attctacagt ggcgagttcc    4920
ctagcactgg caatcatggt agctggtcta tccttatgga tgtgctccaa tggatcgtta    4980
caatgcagaa tttgcattta agatcttttt ccctctgcca aaaattatgg ggacatcatg    5040
aagccccttg agcatctgac ttctggctaa taaaggaaat ttattttcat tgcaatagtg    5100
tgttggaatt ttttgtgtct ctcactcgga aggacataag ggcggccgca acgacgagaa    5160
cgaacgaaga acgctcgaga gtcgatttaa atccccctg tatcgatgca ctgcctcgat     5220
gctgcatcga tgcacaaaat gctagc                                        5246
```

<210> SEQ ID NO 17
<211> LENGTH: 44
<212> TYPE: DNA
<213> ORGANISM: Artificial Sequence
<220> FEATURE:
<223> OTHER INFORMATION: primer for amplifying the pCAH63-CAT RNA-IN-
      SacB (P5/6 6/6) plasmid deleting the R6K replication origin
      (R6KDR01)

<400> SEQUENCE: 17

```
ctccagcacc tgcttttaca caggaacact taacggctga catg                      44
```

<210> SEQ ID NO 18
<211> LENGTH: 48
<212> TYPE: DNA
<213> ORGANISM: Artificial Sequence
<220> FEATURE:
<223> OTHER INFORMATION: primer for amplifying the pCAH63-CAT RNA-IN-
      SacB (P5/6 6/6) plasmid deleting the R6K replication origin
      (R6KDF01)

<400> SEQUENCE: 18

```
cgtgagcacc tgcaactgtg ttgaactgct gatcttcaga tcctctac                  48
```

<210> SEQ ID NO 19
<211> LENGTH: 36
<212> TYPE: DNA
<213> ORGANISM: Artificial Sequence
<220> FEATURE:
<223> OTHER INFORMATION: primer for amplifying murine mouse
      mitochondrial R-region (10110701)

<400> SEQUENCE: 19

```
tgcgcaagta cataaattta catagtacaa cagtac                               36
```

<210> SEQ ID NO 20
<211> LENGTH: 37
<212> TYPE: DNA
<213> ORGANISM: Artificial Sequence
<220> FEATURE:
<223> OTHER INFORMATION: primer for amplifying murine mouse
      mitochondrial R-region (10110702)

<400> SEQUENCE: 20

```
tgcgcattgt taatgtttat tgcgtaatag agtatga                              37
```